(12) United States Patent
Yasuma et al.

(10) Patent No.: US 7,067,527 B2
(45) Date of Patent: *Jun. 27, 2006

(54) THIENOPYRIDINE DERIVATIVES, THEIR PRODUCTION AND USE

(75) Inventors: Tsuneo Yasuma, Ibaraki (JP); Atsuo Baba, Ashiya (JP); Haruhiko Makino, Hyogo (JP); Isao Aoki, Kawanishi (JP); Toshiaki Nagata, Ibaraki (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/662,165

(22) Filed: Sep. 3, 2003

(65) Prior Publication Data

US 2004/0054183 A1    Mar. 18, 2004

Related U.S. Application Data

(62) Division of application No. 10/204,593, filed on Aug. 22, 2002.

(60) Provisional application No. PCT/JP01/01483, filed on Feb. 28, 2001, now Pat. No. 6,653,476.

(30) Foreign Application Priority Data

Feb. 29, 2000   (JP)   ............................. 2000-105770

(51) Int. Cl.
C07D 495/14   (2006.01)
A61K 31/38    (2006.01)

(52) U.S. Cl. ........................................ 514/291; 546/80
(58) Field of Classification Search ................ 514/290, 514/291; 546/80
See application file for complete search history.

(56) References Cited

U.S. PATENT DOCUMENTS

| | | | |
|---|---|---|---|
| 5,747,486 A | 5/1998 | Sohda et al. | 514/211 |
| 6,046,189 A | 4/2000 | Sohda et al. | 514/212 |
| 6,214,838 B1 | 4/2001 | Sohda et al. | 514/293 |
| 6,653,476 B1 * | 11/2003 | Yasuma et al. | 546/15 |

* cited by examiner

Primary Examiner—Zinna Northington Davis
(74) Attorney, Agent, or Firm—Elaine M. Ramesh; Mark Chao

(57) ABSTRACT

The present invention provides thienopyridine derivatives, which are useful as anti-inflammatory drugs, particularly as remedies for arthritis; processes for producing them, and pharmaceutical compositions containing them. The thienopyridine derivatives are represented by the formula (I):

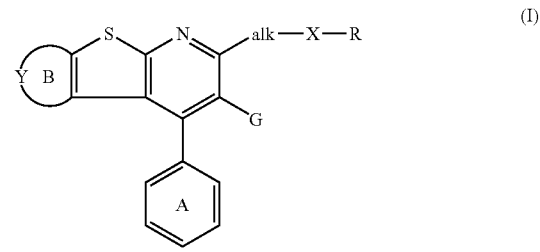

wherein G is a halogen atom, hydroxyl group, an optionally substituted amino group, etc.; alk is an optionally substituted lower alkylene group; X is O, S, $-(CH_2)_q-$, etc.; R is an optionally substituted amino group, etc.; ring B is an optionally substituted Y-containing 5- to 8-membered ring whose ring constituent atoms contain no nitrogen atom; Y is O, S, a group of

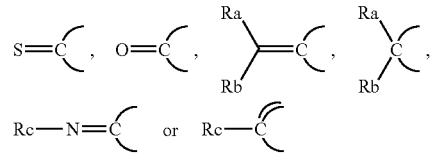

(wherein Ra, Rb and Rc are the same or different, and each is H, a halogen atom, an optionally substituted hydrocarbon group, etc.), etc.; and ring A may be substituted.

25 Claims, No Drawings

THIENOPYRIDINE DERIVATIVES, THEIR PRODUCTION AND USE

This application is a divisional of U.S. patent application Ser. No. 10/204,593, filed Aug. 22, 2002, now U.S. Pat. No. 6,653,476, which was the National Phase filing of International Patent Application No. PCT/JP01/01483, filed Feb. 28, 2001.

THECHNICAL FIELD OF THE INVENTION

The present invention relates to novel thienopyridine derivatives or salts thereof, which have anti-inflammatory activity, bone resorption suppressive activity, immune cytokine production suppressive activity, etc., and are useful as medicaments such as anti-arthritis drugs, etc., and to their production and use.

PRIOR ART

Arthritis is an inflammatory disease of joints, which includes, as major diseases, rheumatoid arthritis and related diseases with inflammation observed in joints.

Among them, rheumatoid arthritis, also called chronic rheumatoid arthritis, is a chronic polyarthritis that is characterized by inflammatory changes in the synovia in the internal capsules of joints as the major lesion. Arthritis such as rheumatoid arthritis is a progressive disease, which brings about joint dysfunctions such as joint deformity, arthrokleisis, and the like, and often leads to serious disability if it is exacerbated without being treated effectively.

Heretofore, drugs available for treating these arthritides have been steroids such as corticosteroids (e.g., cortisone, etc.), non-steroidal anti-inflammatory drugs (e.g., aspirin, piroxicam, indomethacin, etc.), gold compounds (e.g., aurothiomalate, etc.), antirheumatic drugs (e.g., chloroquine preparation, D-penicillamine, etc.), gout suppressants (e.g., colchicines, etc.), immunosuppressants (e.g., cyclophosphamide, azathioprine, methotrexate, levamisole, etc.) and the like. However, some of these drugs have been problematic such as serious adverse reactions, adverse reactions precluding a long-term administration, insufficient efficacy, lack of effect on established arthritis or the like.

Thienopyridine derivatives or thienodipyridine derivatives have been reported as anti-inflammatory drugs, especially as remedies for arthritis, in JP 8-225577 A (PCT International Application Publication No. WO96/14319); JP 10-36374 A (PCT International Application Publication No. WO97/40050), and PCT International Application Publication No. WO97/65916 and the like.

OBJECTS OF THE INVENTION

Medicaments with superior prophylactic and therapeutic efficacy against arthritis and the like have been still desired for the clinical treatment of arthritis and the like.

SUMMARY OF THE INVENTION

Under these circumstances, the present inventors have studied intensively and, as a result, the present inventors have found that novel thienopyridine derivatives, which are represented by the following formula (I) and are characteristic in ring B and group G in the 3-position, are useful as suppressants of joint destruction by possessing potent anti-inflammatory activity, in particular antiarthritic activity, are useful as bone resorption suppressants by possessing the excellent bone resorption suppressing activity with direct effect on the bone, and further are useful as immunosuppressants. The present inventors have further studied based on these findings. Thus the present invention has been completed.

That is, the present invention relates to:

(1) A compound represented by the formula (I):

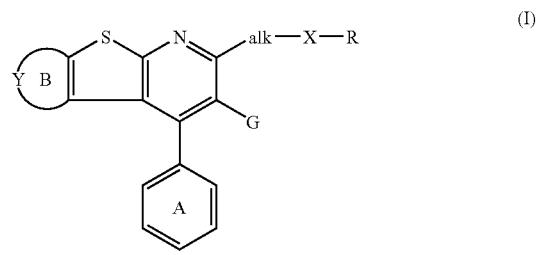

wherein G represents a halogen atom, hydroxyl group, an optionally substituted amino group, an optionally substituted lower alkyl group or an optionally substituted alkoxy group; alk represents an optionally substituted lower alkylene group; X represents oxygen atom, an optionally oxidized sulfur atom, or —(CH$_2$)$_q$— (q represents an integer of 0 to 5); R represents an optionally substituted amino group or an optionally substituted heterocyclic group; ring B represents an optionally substituted Y-containing 5- to 8-membered ring whose ring constituent atoms contain no nitrogen atom; Y represents oxygen atom, an optionally oxidized sulfur atom,

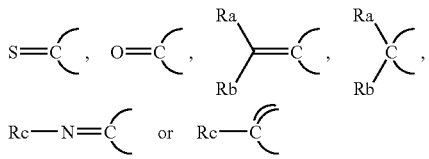

(wherein Ra and Rb are the same or different and, respectively, represent hydrogen atom, a halogen atom, an optionally substituted hydrocarbon group, an optionally substituted acyl group, an optionally substituted carbamoyl group, an optionally substituted thiocarbamoyl group, an optionally substituted sulfonyl group, an optionally substituted sulfinyl group, an optionally substituted hydroxyl group, an optionally substituted thiol group, an optionally esterified carboxyl group, or an optionally substituted heterocyclic group, or Ra and Rb may be combined each other to form a 5- to 7-membered ring; and Rc represents hydrogen atom, a halogen atom, an optionally substituted hydrocarbon group, an optionally substituted acyl group, an optionally substituted carbamoyl group, an optionally substituted thiocarbamoyl group, an optionally substituted sulfonyl group, an optionally substituted sulfinyl group, an optionally substituted hydroxyl group, an optionally substituted thiol group, an optionally esterified carboxyl group, or an optionally substituted heterocyclic group); and ring A represents an optionally substituted benzene ring, or a salt thereof;

(2) The compound according to the above (1), wherein alk is methylene;

(3) The compound according to the above (1), wherein G is a halogen atom;

(4) The compound according to the above (1), wherein G is chlorine atom;

(5) The compound according to the above (1), wherein X is —(CH$_2$)$_q$— (q represents an integer of 0 to 5);

(6) The compound according to the above (1), wherein X is a bond;

(7) The compound according to the above (1), wherein the optionally substituted amino group represented by R is —N(R$^1$)(R$^2$) (wherein R$^1$ and R$^2$, which may be the same or different, respectively, represent hydrogen atom, an optionally substituted hydrocarbon group, or an optionally substituted acyl, sulfonyl, sulfinyl, or heterocyclic group, or R$^1$ and R$^2$ may be combined each other to form an optionally substituted nitrogen-containing 5- to 7-membered heterocyclic group);

(8) The compound according to the above (7), wherein R$^1$ and R$^2$ are combined each other to form a nitrogen-containing optionally substituted 5- to 7-membered heterocyclic group;

(9) The compound according to the above (7), wherein R$^1$ and R$^2$ are acyl groups;

(10) The compound according to the above (1), wherein R is an optionally substituted nitrogen-containing heterocyclic group;

(11) The compound according to the above (1), wherein the substituent on the optionally substituted heterocyclic group represented by R is oxo group;

(12) The compound according to the above (1), wherein R is

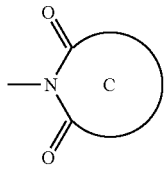

wherein ring C represents a 5- to 7-membered heterocyclic group optionally containing one or more hetero atoms selected from nitrogen, sulfur and oxygen atoms, in addition to the nitrogen atom;

(13) The compound according to the above (1), wherein ring B is an optionally substituted 6-membered ring containing Y;

(14) The compound according to the above (1), wherein the substituents on ring B are one to four substituents selected from a C$_{1-6}$ alkyl group and a halogen atom;

(15) The compound according to the above (1), wherein ring B is a ring represented by the formula:

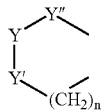

wherein Y' and Y" represent carbon atom, sulfur atom or oxygen atom, respectively; n represents an integer of 0 to 4;

and Y is as defined in the above 1, which may be substituted with one to four substituents selected from a C$_{1-6}$ alkyl group and a halogen atom;

(16) The compound according to the above (1), wherein Y is an optionally oxidized sulfur atom or

(17) The compound according to the above (1), wherein ring A is benzene ring which may be substituted with one to four substituents selected from a halogen atom, nitro group, an optionally substituted alkyl group, an optionally substituted hydroxyl, an optionally substituted thiol group, an optionally substituted amino group, an optionally substituted acyl group, an optionally esterified carboxyl group, and an optionally substituted aromatic ring group;

(18) The compound according to the above (1), wherein the substituent on ring A is a C$_{1-6}$ alkoxy group or hydroxyl group;

(19) The compound according to the above (1), wherein the compound represented by formula (I) is:

1-{[3-chloro-4-(4-methoxyphenyl)-7-oxo-5,6,7,8-tetrahydro[1]benzothieno[2,3-b]pyridin-2-yl]methly}-2,5-pyrrolidinedione ethylene ketal;

3-{[3-chloro-4-(4-methoxyphenyl)-7-oxido-5,8-dihydro-6H-thiopyrano[4',3':4,5]thieno[2,3-b]pyridin-2-yl]methyl}-1,3-thiazolidine-2,4-dione or an optically active substance thereof or a salt thereof;

3-{[3-chloro-4-(4-methoxyphenyl)-7-oxido-5,8-dihydro-6H-thiopyrano[4',3':4,5]thieno[2,3-b]pyridin-2-yl]methyl}-1,3-oxazolidine-2,4-dione or an optically active substance thereof or a salt thereof;

1-{[3-chloro-4-(4-methoxyphenyl)-7-oxido-5,8-dihydro-6H-thiopyrano[4',3':4,5]thieno[2,3-b]pyridin-2-yl]methyl}-2,5-pyrrolidinedione or an optically active substance thereof or a salt thereof;

1-{[3-chloro-4-(4-methoxyphenyl)-7-oxo-5,6,7,8-tetrahydro [1]benzothieno[2,3-b]pyridin-2-yl]methyl}-2,5-pyrrolidinedione or a salt thereof;

1-{[3-chloro-4-(4-methoxyphenyl)-7-oxo-5,6,7,8-tetrahydro[1]benzothieno[2,3-b]pyridin-2-yl]methyl}-2,5-pyrrolidinedione or a salt thereof;

3-{[3-chloro-4-(4-methoxyphenyl)-8,8-dimethyl-7-oxo-5,6,7,8-tetrahydro[1]benzothieno[2,3-b]pyridin-2-yl]methyl}-1,3-thiazolidine-2,4-dione or a salt thereof;

1-{[3-chloro-4-(4-methoxyphenyl)-6,6-dimethyl-7-oxo-5,6,7,8-tetrahydro[1]benzothieno[2,3-b]pyridin-2-yl]methyl}-2,5-pyrrolidinedione or a salt thereof; or 2-aminomethyl-3-chloro-4-(4-methoxyphenyl)-7-oxido-5,8-dihydro-6H-thiopyrano[4',3':4,5]thieno[2,3-b]pyridine or an optically active substance thereof or a salt thereof;

(20) The compound according to the above (1), wherein the compound represented by formula (I) is:

3-{[3-chloro-4-(4-methoxyphenyl)-7-oxido-5,8-dihydro-6H-thiopyrano[4',3':4,5]thieno[2,3-b]pyridin-2-yl]methyl}-1,3-thiazolidine-2,4-dione or an optically active substance thereof or a salt thereof;

3-{[3-chloro-4-(4-methoxyphenyl)-7-oxido-5,8-dihydro-6H-thiopyrano[4',3':4,5]thieno[2,3-b]pyridin-2-yl]methyl}-1,3-oxazolidine-2,4-dione or an optically active substance thereof or a salt thereof; or 1-{[3-chloro-4-(4-methoxyphenyl)-7-oxido-5,8-dihydro-6H-thiopyrano[4',3':4,5]thieno[2,3-b]pyridin-2-yl]methyl}-2,5-pyrrolidinedione or an optically active substance thereof or a salt thereof;

(21) The compound according to the above (1), wherein the compound represented by formula (I) is:

1-{[3-chloro-4-(4-methoxyphenyl)-7-oxo-5,6,7,8-tetrahydro[1]benzothieno[2,3-b]pyridin-2-yl]methyl}-2,5-pyrrolidinedione or a salt thereof;

1-{[3-chloro-4-(4-methoxyphenyl)-8,8-dimethyl-7-oxo-5,6,7,8-tetrahydro[1]benzothieno[2,3-b]pyridin-2-yl]methyl}-2,5-pyrrolidinedione or a salt thereof;

3-{[3-chloro-4-(4-methoxyphenyl)-8,8-dimethyl-7-oxo-5,6,7,8-tetrahydro[1]benzothieno[2,3-b]pyridin-2-yl]methyl}-1,3-thiazolidine-2,4-dione or a salt thereof; or 1-{[3-chloro-4-(4-methoxyphenyl)-6,6-dimethyl-7-oxo-5,6,7,8-tetrahydro[1]benzothieno[2,3-b]pyridin-2-yl]methyl}-2,5-pyrrolidinedione or a salt thereof;

(22) The compound according to the above (1), wherein the compound represented by formula (I) is:

1-{[3-chloro-4-(4-hydroxyphenyl)-7,7-dioxido-5,8-dihydro-6H-thiopyrano[4',3':4,5]thieno[2,3-b]pyridin-2-yl]methyl}-2,5-pyrrolidinedione or a salt thereof;

4-{3-chloro-2-[(2,5-dioxo-1-pyrrolidinyl)methyl]-7,7-oxido-5,8-dihydro-6H-thiopyrano[4',3':4,5]thieno[2,3-b]pyridin-4-yl}phenyl diisobutyl phosphate or a salt thereof; or butyl 4-{3-chloro-2-[(2,5-dioxo-1-pyrrolidinyl)methyl]-7,7-dioxido-5,8-dihydro-6H-thiopyrano[4',3':4,5]thieno[2,3-b]pyridin-4-yl}phenyl carbonate or a salt thereof;

(23) A prodrug of the compound according to the above (1);

(24) A process for producing a compound represented by the general formula (I):

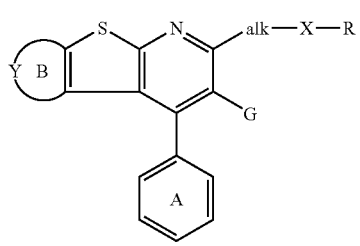

(I)

wherein G represents a halogen atom, hydroxyl group, an optionally substituted amino group, an optionally substituted lower alkyl group or an optionally substituted alkoxy group; alk represents an optionally substituted lower alkylene group; X represents oxygen atom, an optionally oxidized sulfur atom, or $—(CH_2)_q—$ (q represents an integer of 0 to 5); R represents an optionally substituted amino group or an optionally substituted heterocyclic group; ring B represents an optionally substituted Y-containing 5- to 8-membered ring whose ring constituent atoms contain no nitrogen atom; Y represents oxygen atom, an optionally oxidized sulfur atom,

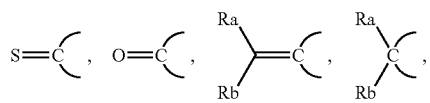

(wherein Ra and Rb are the same or different and, respectively, represent hydrogen atom, a halogen atom, an optionally substituted hydrocarbon group, an optionally substituted acyl group, an optionally substituted carbamoyl group, an optionally substituted thiocarbamoyl group, an optionally substituted sulfonyl group, an optionally substituted sulfinyl group, an optionally substituted hydroxyl group, an optionally substituted thiol group, an optionally esterified carboxyl group, or an optionally substituted heterocyclic group, or Ra and Rb may be combined each other to form a 5- to 7-membered ring; and Rc represents hydrogen atom, a halogen atom, an optionally substituted hydrocarbon group, an optionally substituted acyl group, an optionally substituted carbamoyl group, an optionally substituted thiocarbamoyl group, an optionally substituted sulfonyl group, an optionally substituted sulfinyl group, an optionally substituted hydroxyl group, an optionally substituted thiol group, an optionally esterified carboxyl group, or an optionally substituted heterocyclic group); and ring A represents an optionally substituted benzene ring, or a salt thereof which comprises reacting a compound represented by the formula (II-1):

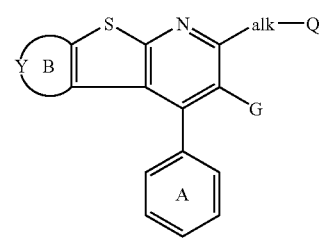

(II-1)

wherein Q represents a leaving group; and the other symbols are as defined above, or a salt thereof, with a compound represented by the formula (III):

(III)

wherein R is as defined above; and $X^1$ represents oxygen atom, or an optionally oxidized sulfur atom, or a salt thereof to obtain a compound represented by the formula (1-1):

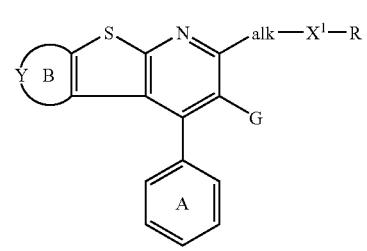

(I-1)

wherein each symbol is as defined above, or a salt thereof;
or
reacting a compound represented by the formula (II-2):

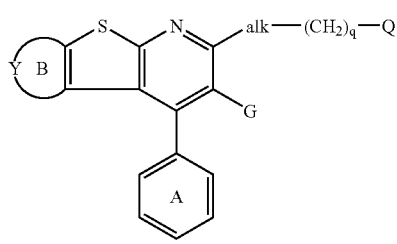

wherein each symbol is as defined above, or a salt thereof, with a compound represented by the formula (IV):

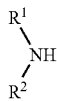

wherein $R^1$ and $R^2$, which may be the same or different, respectively, represent an optionally substituted hydrocarbon group, an optionally substituted acyl group, an optionally substituted sulfonyl group, or an optionally substituted heterocyclic group, or $R^1$ and $R^2$ may be combined each other to form an optionally substituted nitrogen-containing 5- to 7-membered ring, or a salt thereof to obtain a compound represented by the formula (I-2):

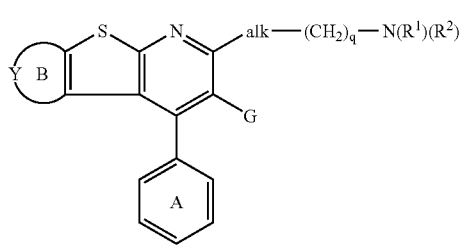

wherein each symbol is as defined above, or a salt thereof;
or
subjecting a compound represented by the formula (I-3):

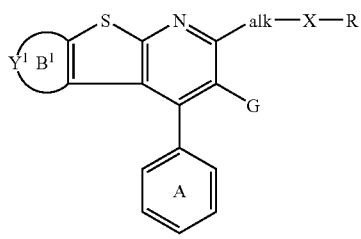

wherein ring $B^1$ represents an optionally substituted $Y^3$-containing 5- to 8-membered ring whose ring constituent atoms contain no nitrogen atom; $Y^1$ represents sulfur atom or

and the other symbols are as defined above, or a salt thereof to oxidation to obtain a compound represented by the formula (I-4):

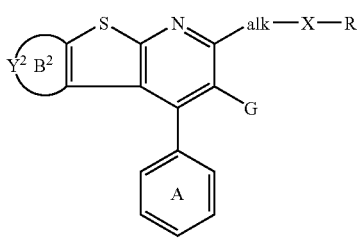

wherein ring $B^2$ represents an optionally substituted $Y^2$-containing 5- to 8-membered ring whose ring constituent atoms contain no nitrogen atom; $Y^2$ represents an oxidized sulfur atom or

and the other symbols are as defined above, or a salt thereof;
or
reacting a compound represented by the formula (II-3):

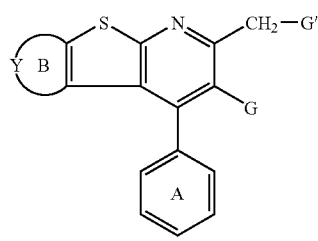

wherein G' represents a halogen atom; and the other symbols are as defined above, or a salt thereof, with

in a solvent to obtain a compound represented by formula (VI):

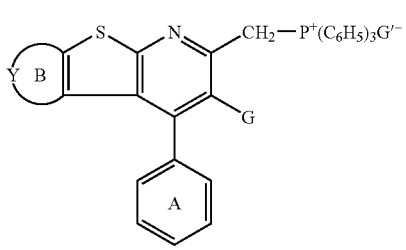

(VI)

wherein each symbol is as defined above, then reacting the compound represented by the formula (VI) with a compound represented by the formula (VII):

$$Z^1\text{-}(CH_2)_{q'}CHO \quad (VII)$$

wherein $Z^1$ represents an optionally substituted heterocyclic group; and q' represents an integer of 0 to 4, or a salt thereof to obtain a compound represented by formula (VIII):

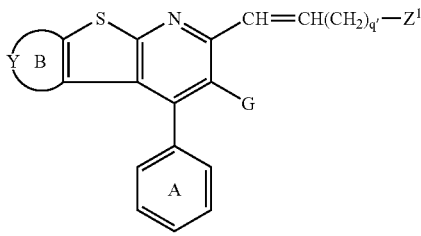

(VIII)

wherein each symbol is as defined above, or a salt thereof, and further subjecting the compound represented by formula (VIII) or a salt thereof to reduction to obtain a compound represented by the formula (I-5):

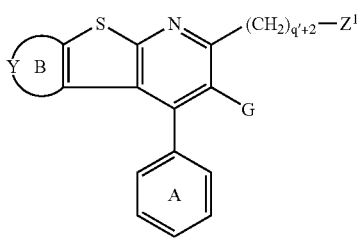

(I-5)

wherein each symbol is as defined above, or a salt thereof; or reacting a compound represented by the formula (II-1):

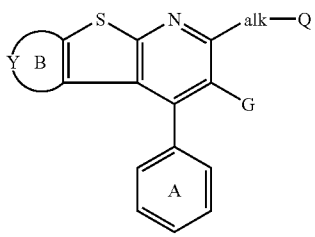

(II-1)

wherein each symbol is as defined above, or a salt thereof, with a compound represented by formula (XII):

$$R\text{—}H \quad (XII)$$

wherein R is as defined above, or a salt thereof to obtain a compound represented by the formula (I-9):

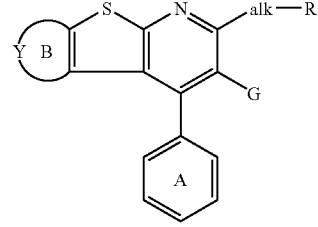

(I-9)

wherein each symbols is as defined above, or a salt thereof;

(25) A pharmaceutical composition comprising a compound represented by the general formula (I):

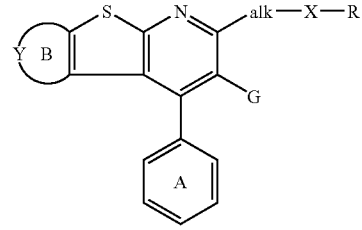

(I)

wherein G represents a halogen atom, hydroxyl group, an optionally substituted amino group, an optionally substituted lower alkyl group or an optionally substituted alkoxy group; alk represents an optionally substituted lower alkylene group; X represents oxygen atom, an optionally oxidized sulfur atom, or —$(CH_2)_q$— (q represents an integer of 0 to 5); R represents an optionally substituted amino group or an optionally substituted heterocyclic group; ring B represents an optionally substituted Y-containing 5- to 8-membered ring whose ring constituent atoms contain no nitrogen atom; Y represents oxygen atom, an optionally oxidized sulfur atom,

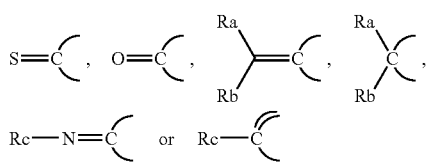

(wherein Ra and Rb are the same or different and, respectively, represent hydrogen atom, a halogen atom, an optionally substituted hydrocarbon group, an optionally substituted acyl group, an optionally substituted carbamoyl group, an optionally substituted thiocarbamoyl group, an optionally substituted sulfonyl group, an optionally substituted sulfinyl group, an optionally substituted hydroxyl group, an optionally substituted thiol group, an optionally esterified carboxyl group, or an optionally substituted heterocyclic group, or Ra and Rb may be combined each other to form a 5- to 7-membered ring; and Rc represents hydrogen atom, a halogen atom, an optionally substituted hydrocarbon group, an optionally substituted acyl group, an optionally substituted carbamoyl group, an optionally substituted thiocarbamoyl group, an optionally substituted sulfonyl group, an optionally substituted sulfinyl group, an optionally substituted hydroxyl group, an optionally substituted thiol group, an optionally esterified carboxyl group, or an optionally substituted heterocyclic group); and ring A represents an optionally substituted benzene ring, a prodrug thereof, or a pharmaceutically acceptable salt thereof;

(26) The pharmaceutical composition according to the above (25) for prevention or treatment of inflammatory diseases;

(27) The pharmaceutical composition according to the above (25) for prevention or treatment of arthritis;

(28) The pharmaceutical composition according to the above (25) for prevention or treatment of rheumatism;

(29) The pharmaceutical composition according to the above (25) for prevention or treatment of chronic rheumatoid arthritis;

(30) The pharmaceutical composition according to the above (25), which is a bone resorption suppressant;

(31) The pharmaceutical composition according to the above (25) for prevention or treatment of osteoporosis;

(32) The pharmaceutical composition according to the above (25), which is a suppressant of cytokine production;

(33) The pharmaceutical composition according to the above (25) for prevention or treatment of autoimmune diseases;

(34) The pharmaceutical composition according to the above (25) for prevention or treatment of rejection reaction after organ transplantation;

(35) The pharmaceutical composition according to the above (25), which is a T-cell differentiation-controlling medicament.

(36) A method for preventing or treating inflammatory diseases which comprises administering an effective amount of a compound represented by the formula (I):

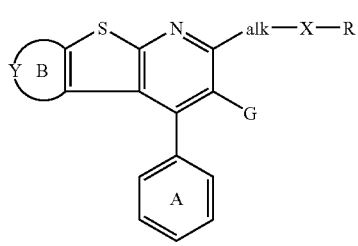

wherein G represents a halogen atom, hydroxyl group, an optionally substituted amino group, an optionally substituted lower alkyl group or an optionally substituted alkoxy group; alk represents an optionally substituted lower alkylene group; X represents oxygen atom, an optionally oxidized sulfur atom, or —(CH$_2$)$_q$— (q represents an integer of 0 to 5); R represents an optionally substituted amino group or an optionally substituted heterocyclic group; ring B represents an optionally substituted Y-containing 5- to 8-membered ring whose ring constituent atoms contain no nitrogen atom; Y represents oxygen atom, an optionally oxidized sulfur atom,

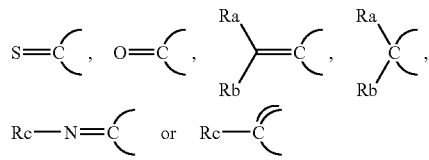

(wherein Ra and Rb are the same or different and, respectively, represent hydrogen atom, a halogen atom, an optionally substituted hydrocarbon group, an optionally substituted acyl group, an optionally substituted carbamoyl group, an optionally substituted thiocarbamoyl group, an optionally substituted sulfonyl group, an optionally substituted sulfinyl group, an optionally substituted hydroxyl group, an optionally substituted thiol group, an optionally esterified carboxyl group, or an optionally substituted heterocyclic group, or Ra and Rb may be combined each other to form a 5- to 7-membered ring; and Rc represents hydrogen atom, a halogen atom, an optionally substituted hydrocarbon group, an optionally substituted acyl group, an optionally substituted carbamoyl group, an optionally substituted thiocarbamoyl group, an optionally substituted sulfonyl group, an optionally substituted sulfinyl group, an optionally substituted hydroxyl group, an optionally substituted thiol group, an optionally esterified carboxyl group, or an optionally substituted heterocyclic group); and ring A represents an optionally substituted benzene ring, a prodrug thereof, or a pharmaceutically acceptable salt thereof, to a mammal in need of the prevention or treatment; and

(37) Use of a compound represented by the formula (I):

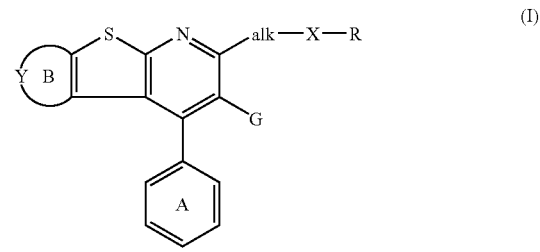

wherein G represents a halogen atom, hydroxyl group, an optionally substituted amino group, an optionally substituted lower alkyl group or an optionally substituted alkoxy group; alk represents an optionally substituted lower alkylene group; X represents oxygen atom, an optionally oxidized sulfur atom, or —(CH$_2$)$_q$— (q represents an integer of 0 to 5); R represents an optionally substituted amino group or an optionally substituted heterocyclic group; ring B represents an optionally substituted Y-containing 5- to 8-membered ring whose ring constituent atoms contain no nitrogen atom; Y represents oxygen atom, an optionally oxidized sulfur atom,

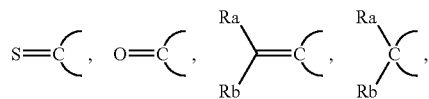

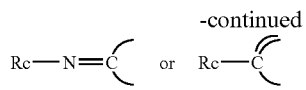

(wherein Ra and Rb are the same or different and, respectively, represent hydrogen atom, a halogen atom, an optionally substituted hydrocarbon group, an optionally substituted acyl group, an optionally substituted carbamoyl group, an optionally substituted thiocarbamoyl group, an optionally substituted sulfonyl group, an optionally substituted sulfinyl group, an optionally substituted hydroxyl group, an optionally substituted thiol group, an optionally esterified carboxyl group, or an optionally substituted heterocyclic group, or Ra and Rb may be combined each other to form a 5- to 7-membered ring; and Rc represents hydrogen atom, a halogen atom, an optionally substituted hydrocarbon group, an optionally substituted acyl group, an optionally substituted carbamoyl group, an optionally substituted thiocarbamoyl group, an optionally substituted sulfonyl group, an optionally substituted sulfinyl group, an optionally substituted hydroxyl group, an optionally substituted thiol group, an optionally esterified carboxyl group, or an optionally substituted heterocyclic group); and ring A represents an optionally substituted benzene ring, a prodrug thereof, or a pharmaceutically acceptable salt thereof in the manufacture of a pharmaceutical composition for preventing or treating inflammatory diseases.

DETAILED EXPLANATION OF THE INVENTION

The explanation of all definitions included in the above-mentioned general formulas and in the scope of the present invention as well as preferred examples thereof will be described below.

In the above formula (I), G represents a halogen atom (e.g., chlorine, bromine, iodine or fluorine); hydroxyl group, an optionally substituted amino group [e.g., amino group, a N—($C_{1-6}$ alkyl)amino group such as methylamino, ethylamino, propylamino, butylamino, etc.; a N,N-di($C_{1-6}$ alkyl) amino group such as dimethylamino, diethylamino, dipropylamino, dibutylamino, etc.]; an optionally substituted lower alkyl group [e.g., a $C_{1-6}$ alkyl group (e.g., methyl, ethyl, propyl, butyl, etc.) which may be substituted with one to three halogen atoms]; or an optionally substituted lower alkoxy group [e.g., a $C_{1-6}$ alkoxy group (e.g., methoxy, ethoxy, propoxy, butoxy, etc.) which may be substituted with 1 to 3 halogen atoms]. A preferred example of G is a halogen atom with chlorine being more preferred.

In the above formula, G represents a halogen atom (e.g., chlorine, bromine, iodine or fluorine). A preferred example of G' is chlorine.

Examples of the lower alkylene group of the optionally substituted lower alkylene group represented by alk include a $C_{1-6}$ alkylene group such as methylene, ethylene, propylene, and the like.

Examples of the substituents of the lower alkylene group represented by alk include 1 to 4 substituents selected from a halogen atom (e.g., chlorine, bromine, iodine or fluorine), hydroxyl group, an optionally substituted amino group [e.g., amino group, a N—($C_{1-6}$ alkyl)amino group such as methylamino, ethylamino, propylamino, butylamino, etc.; a N,N-di($C_{1-6}$ alkyl)amino group such as dimethylamino, diethylamino, dipropylamino, dibutylamino, etc.], a optionally substituted lower alkyl group [e.g., a $C_{1-6}$ alkyl group (e.g., methyl, ethyl, propyl, butyl, etc.) which may be substituted with 1 to 3 halogen atom, etc.], and an optionally substituted alkoxy group [e.g., a $C_{1-6}$ alkoxy group (e.g., methoxy, ethoxy, propoxy, butoxy, etc.) which may be substituted 1 to 3 halogen atom, etc.].

In the above formula (I), X represents oxygen atom, an optionally oxidized sulfur atom, or —$(CH_2)_q$— (q represents an integer of 0 to 5, preferably an integer of 0 to 3, and more preferably 0). As the optionally oxidized sulfur atom represented by X, there is thio group, sulfinyl group, and sulfonyl group, with thio group being preferred.

Preferably, X is —$(CH_2)_q$— (q represents an integer of 0 to 5, preferably an integer of 0 to 3, and more preferably 0).

In the above formula (I), examples of the optionally substituted amino group represented by R include a group represented by the formula: —$N(R^1)(R^2)$ (wherein $R^1$ and $R^2$, which may be the same or different, respectively, represent hydrogen atom or a hydrocarbon group, an acyl group, sulfonyl group, sulfinyl group or a heterocyclic group (preferably an acyl group), which respectively may be substituted, or $R^1$ and $R^2$ are combined each other to form an optionally substituted nitrogen-containing heterocyclic ring), and the like.

Examples of the hydrocarbon group in the optionally substituted hydrocarbon group represented by $R^1$ or $R^2$ include an aliphatic hydrocarbon group, an alicyclic hydrocarbon group, an alicyclic-aliphatic hydrocarbon group, an aromatic aliphatic hydrocarbon group, an aromatic hydrocarbon group, and the like.

Examples of said aliphatic hydrocarbon group include a $C_{1-8}$ saturated aliphatic hydrocarbon group (e.g., $C_{1-8}$ alkyl such as methyl, ethyl, propyl, isopropyl, butyl, isobutyl, sec-butyl, tert-butyl, pentyl, isopentyl, neopentyl, tert-pentyl, hexyl, isohexyl, heptyl, octyl, etc.), a $C_{2-8}$ unsaturated aliphatic hydrocarbon group (e.g., $C_{2-8}$ alkenyl, $C_{2-8}$ alkynyl, $C_{4-8}$ alkadienyl, and $C_{4-8}$ alkadiynyl, such as vinyl, 1-propenyl, 2-propenyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 3-hexenyl, 2,4-hexadienyl, 5-hexenyl, 1-heptenyl, 1-octenyl, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 3-hexynyl, 2,4-hexadiynyl, 5-hexynyl, 1-heptynyl, 1-octynyl, etc.), and the like.

Examples of said alicyclic hydrocarbon group include $C_{3-7}$ saturated alicyclic hydrocarbon group (e.g., $C_{3-7}$ cycloalkyl such as cyclopropyl, cyclobutyl, cyclopentyl, cyclohexyl, cycloheptyl, etc.) and $C_{5-7}$ unsaturated alicyclic hydrocarbon group (e.g., $C_{5-7}$ cycloalkenyl and $C_{5-7}$ cycloalkadienyl such as 1-cyclopentenyl, 2-cyclopentenyl, 3-cyclopentenyl, 1-cyclohexenyl, 2-cyclohexenyl, 3-cyclohexenyl, 1-cycloheptenyl, 2-cycloheptenyl, 3-cycloheptenyl, 2,4-cycloheptadienyl, etc.) and the like.

Examples of said alicyclic-aliphatic hydrocarbon group include, among the residues formed by combination of the above-mentioned alicyclic hydrocarbon groups and the above-mentioned aliphatic hydrocarbon groups, that having 4 to 9 carbon atoms such as cycloalkylalkyl, cycloalkylalkeny, and the like, each of which having 4 to 9 carbon atoms (e.g., cyclopropylmethyl, cyclopropylethyl, cyclobutylmethyl, cyclopentylmethyl, 2-cyclopentenylmethyl, 3-cyclopentenylmethyl, cyclohexylmethyl, 2-cyclohexenylmethyl, 3-cyclohexenylmethyl, cyclohexylethyl, cyclohexylpropyl, cycloheptylmethyl, cyclobutylethyl, etc.).

Examples of said aromatic alicyclic hydrocarbon group include $C_{7-9}$ phenylalkyl (e.g., benzyl, phenethyl, 1-phenylethyl, 3-phenylpropyl, 2-phenylpropyl, 1-phenylpropyl, etc.) and $C_{11-13}$ naphthylalkyl (e.g., α-naphthylmethyl, α-naphthylethyl, β-naphthylmethyl, β-naphthylethyl, etc.) and the like.

Examples of said aromatic hydrocarbon group include phenyl, naphthyl (α-naphthyl and β-naphthyl), and the like.

As for the hydrocarbon group in the optionally substituted hydrocarbon group represented by $R^1$ or $R^2$, $C_{1-6}$, straight chain or branched chain alkyl, particularly $C_{1-4}$, straight chain alkyl or $C_{3-4}$, branched chain alkyl is preferred. Specifically, groups such as methyl, ethyl, propyl, isopropyl, butyl, and the like are preferred.

Examples of the acyl group in the optionally substituted acyl group represented by $R^1$ or $R^2$ include (i) formyl, or (ii) groups where the carbonyl group is combined to a $C_{1-10}$ alkyl group, a $C_{2-10}$ alkenyl group, a $C_{3-10}$ alkynyl group, $Cx_{3-7}$ cycloalkyl, $C_{5-7}$ cycloalkenyl, or an aromatic group (e.g., phenyl group, pyridyl group, etc.), (e.g., acetyl, propionyl, butyryl, isobutyryl, valeryl, isovaleryl, pivaloyl, hexanoyl, heptanoyl, octanoyl, cyclobutanecarbonyl, cyclopentanecarbonyl, cyclohexanecarbonyl, cycloheptanecarbonyl, crotonyl, 2-cyclohexenecarbonyl, benzoyl, nicotinoyl, etc.).

Examples of the sulfonyl group in the optionally substituted sulfonyl group represented by $R^1$ or $R^2$ include groups where the sulfonyl group is combined to a $C_{1-10}$ alkyl group, a $C_{2-10}$ alkenyl group, a $C_{2-10}$ alkynyl group, $C_{3-7}$ cycloalkyl, $C_{5-7}$ cycloalkenyl, or an aromatic group (e.g., phenyl group, pyridyl group, etc.), (e.g., methanesulfonyl, ethanesulfonyl, benzenesulfonyl, etc.).

Examples of the sulfinyl group in the optionally substituted sulfinyl group represented by $R^1$ or $R^2$ include groups where the sulfinyl group is combined to a $C_{1-10}$ alkyl group, a $C_{2-10}$ alkenyl group, a $C_{2-10}$ alkynyl group, $C_{3-7}$ cycloalkyl, $C_{5-7}$ cycloalkenyl, or an aromatic group (e.g., phenyl group, pyridyl group, etc.), (e.g., methanesulfinyl, ethanesulfinyl, benzenesulfinyl, etc.).

Examples of the heterocyclic group in the optionally substituted heterocyclic group represented by $R^1$ or $R^2$ include (i) 5- to 7-membered heterocyclic groups containing one sulfur atom, one nitrogen atom, or one oxygen atom, (ii) 5- to 6-membered heterocyclic groups containing 2–4 nitrogen atoms, (iii) 5- to 6-membered heterocyclic groups containing 1–2 nitrogen atoms and one sulfur or oxygen atom, or the like, and (iv) these heterocyclic groups may be condensed with a 5- to 6-membered ring containing 2 or less nitrogen atoms, benzene ring, or a 5-membered ring containing one sulfur atom. In addition, each of the heterocyclic groups exemplified in (i) to (iv) may be a saturated or unsaturated heterocyclic group and the unsaturated heterocyclic group may be either aromatic or non-aromatic.

Examples of the heterocyclic group in the optionally substituted heterocyclic group represented by $R^1$ and $R^2$ include an aromatic-monocyclic heterocyclic group, an aromatic condensed heterocyclic group, and a non-aromatic, heterocyclic group.

Specific examples of the heterocyclic group in the optionally substituted heterocyclic group represented by $R^1$ and $R^2$ include (i) an aromatic-monocyclic heterocyclic group (e.g., furyl, thienyl, pyrrolyl, oxazolyl, isooxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyrimidinyl, pyridazinyl, pyrazinyl, triazinyl, etc.), (ii) an aromatic condensed heterocyclic group (e.g., benzofuranyl, isobenzofuranyl, benzo[b]thienyl, indolyl, isoindolyl, 1H-indazolyl, benzoimidazolyl, benzooxazolyl, 1,2-benzoisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxatinyl, thianthrenyl, phenanthredinyl, phenanthrolinyl, indolizinyl, pyrrolo[1,2-b]pyridazinyl, pyrazo[1,5-a]pyridyl, imidazo[1,2-a]pyridyl, imidazo[1,5-a]pyridyl, imidazo[1,2-b]pyridazinyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl, etc.), and (iii) a non-aromatic, heterocyclic group (e.g., oxiranyl, azetidinyl, oxetanyl, thietanyl, pyrrolidinyl, tetrahydrofuryl, thiolanyl, piperidyl, tetrahydropyranyl, morpholinyl, thiomorpholinyl, piperazinyl, etc.).

In the case where $R^1$ and $R^2$ are combined each other to form a ring, particularly a nitrogen-containing 5- to 7-membered ring, examples of such $—N(R^1)(R^2)$ include 1-pyrrolyl, 1-pyrrolidinyl, 1-imidazolidinyl, 1-pyrazolidinyl, 1-piperidyl (piperidino), 1-piperazinyl, 4-morpholinyl (morpholino), 4-thiomorpholinyl, homopiperazin-1-yl, pyrazol-1-yl, imidazol-1-yl, 1,3-thiadiazol-3-yl, 1,3-oxadiazol-3-yl, 1,2,4-triazol-1-yl, 1,2,4-triazol-2-yl, 1,2,4-triazol-4-yl, 1,2,3-triazol-1-yl, 1,2,4-triazol-2-yl, tetrazol-1-yl, oxazol-3-yl, thiazol-3-yl, and a partly or whole saturated nitrogen-containing heterocyclic group thereof. These heterocyclic groups may have the 1 to 3 same substituents as those of the hydrocarbon group, the acyl group, the sulfonyl group, the sulfinyl group and the heterocyclic group as described hereinafter, and may be condensed with the above-mentioned aromatic, monocyclic heterocyclic group or an aromatic ring such as benzene ring or the like. Specific examples in the case where the heterocyclic group condensed with the aromatic ring include benzimidazol-1-yl, indol-1-yl, 1H-indazol-1-yl, and the like; preferably, 1,2,4-triazol-1-yl, 1,2,4-triazol-2-yl, imidazol-1-yl, morpholino (4-morpholinyl), piperidino (1-piperidyl), oxazolidin-3-yl, thiazolidin-3-yl, hydantoin-1-yl, pyrrolidino (1-pyrrolidin-1-yl) and the like, each of which may be substituted and may be condensed with benzene ring; more preferably, a nitrogen-containing 5- to 7-membered ring that may have 1 to 2 oxo groups (e.g., 2,4-dioxooxazolidin-3-yl, 2,4-dioxothiazolidin-3-yl, 2,5-dioxohydantoin-1-yl, 2,5-dioxopyrrolidin-1-yl, etc.), with 2,5-dioxopyrrolidin-1-yl being particularly preferred.

The hydrocarbon group, the acyl group, the sulfonyl group, the sulfinyl group and the heterocyclic group represented by $R^1$ or $R^2$ may have 1 to 3 substituents at any possible positions on the chain or the ring thereof.

Examples of such a substituent of the hydrocarbon group, the acyl group, the sulfonyl group, the sulfinyl group and the heterocyclic group represented by $R^1$ or $R^2$ include an aliphatic-chain hydrocarbon group, an alicyclic hydrocarbon group, an aryl group, an aromatic, heterocyclic group, a non-aromatic, heterocyclic group, a halogen atom, an optionally substituted amino group, amidino group, an optionally substituted acyl group, an optionally substituted hydroxyl group, an optionally substituted thiol group, an optionally esterified or amidated carboxyl group, an aralkyl group (e.g., a $C_{6-14}$ aryl-$C_{1-6}$ alkyl group, etc.), a carbamoyl group, an optionally substituted thocarbamoyl group, an N-mono-substituted carbamoyl group (e.g., methylcarbamoyl, ethylcarbamoyl, phenylcarbamoyl, etc.), an N,N-disubstituted carbamoyl group (N,N-dimethylcarbamoyl, N,N-diethylcarbamoyl, piperidinocarbamoul, morpholinocarbamoyl, etc.), a sulfamoyl group, an N-mono-substituted sulfamoyl group (e.g., methylsulfamoyl, ethylsulfamoyl, phenylsulfamoyl, p-toluenesulfamoyl, etc.), an N,N-disubstituted sulfamoyl group (e.g., N,N-dimethylsulfamoyl, N-methyl-N-phenylsulfamoyl, piperidinosulfamoyl, morpholinosulfamoyl, etc.), mercapto group, sulfo group, cyano group, azido group, nitro group, nitroso group, oxo group, and the like.

Examples of the aliphatic-chain hydrocarbon group as the substituent of the hydrocarbon group, the acyl group, the sulfonyl group, the sulfinyl group and the heterocyclic group represented by $R^1$ or $R^2$ include a straight or branched chain aliphatic hydrocarbon group such as an alkyl group (preferably, a $C_{1-10}$ alkyl group), an alkenyl group (preferably, a $C_{2-10}$ alkenyl group), an alkynyl group (preferably, a $C_{2-10}$ alkynyl group), and the like. Preferred examples of said alkyl group include methyl, ethyl, propyl, isopropyl, butyl, isobutyl, sec-butyl, tert-butyl, pentyl, isopentyl, neopentyl, tert-pentyl, 1-ethylpropyl, hexyl, isohexyl, 1,1-dimethylbutyl, 2,2-dimethylbutyl, 3,3-dimethylbutyl, 2-ethylbutyl, hexyl, pentyl, octyl, nonyl, decyl, and the like. Preferred examples of said alkenyl group include vinyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl, and the like. Preferred examples of said alkynyl group include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, and the like.

Examples of the alicyclic hydrocarbon group as the substituent of the hydrocarbon group, the acyl group, the sulfonyl group, the sulfinyl group and the heterocyclic group represented by $R^1$ or $R^2$ include a saturated or unsaturated $C_{3-8}$ alicyclic hydrocarbon group such as a $C_{3-8}$ cycloalkyl group, a $C_{3-8}$ cycloalkenyl group, a $C_{4-8}$ cycloalkadienyl group and the like. Preferred examples of said $C_{3-8}$ cycloalkyl group include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, and the like. Preferred examples of said $C_{3-8}$ cycloalkenyl group include 2-cyclopenten-1-yl, 3-cyclopenten-1-yl, 2-cyclohexen-1-yl, 3-cyclohexen-1-yl, and the like. Preferred examples of said $C_{4-8}$ cycloalkadienyl group include 2,4-cyclopentadien-1-yl, 2,4-cyclohexadien-1-yl, 2,5-cyclohexadien-1-yl, and the like.

The aryl group as the substituent of the hydrocarbon group, the acyl group, the sulfonyl group, the sulfinyl group and the heterocyclic group represented by $R^1$ or $R^2$, and the aryl group in the aralkyl group mean a monocyclic, or condensed polycyclic aromatic hydrocarbon group. Preferred examples thereof include phenyl, naphthyl, anthryl, phenanthryl, acenaphthenyl, and the like, with $C_{6-10}$ aryl such as phenyl, 1-naphthyl, 2-naphthyl, and the like being more preferred.

Examples of an optionally substituted thiocarbamoyl group as the substituent of the hydrocarbon group, the acyl group, the sulfonyl group, the sulfinyl group and the heterocyclic group represented by $R^1$ or $R^2$ include methylthiocarbamoyl, ethylthiocarbamoyl, phenylthiocarbamoyl and the like.

Preferred examples of the aromatic heterocyclic group as the substituent of the hydrocarbon group, the acyl group, the sulfonyl group, the sulfinyl group and the heterocyclic group represented by $R^1$ or $R^2$ include an aromatic monocyclic heterocyclic group (e.g., a 5- to 6-memberd aromatic, monocyclic heterocyclic group containing 1 to 4 heteroatoms selected from nitrogen, sulfur, and oxygen atoms, such as furyl, thienyl, pyrrolyl, oxazolyl, isooxazolyl, thiazolyl, isothiazolyl, imidazolyl, pyrazolyl, 1,2,3-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pirazinyl, triazinyl, etc.) as well as an aromatic condensed heterocyclic group (e.g., a 8- to 12-memberd aromatic, monocyclic heterocyclic group containing 1 to 4 heteroatoms selected from nitrogen, sulfur, and oxygen atoms, such as benzofuranyl, isobenzofuranyl, benzo[b]thienyl, indolyl, isoindolyl, 1H-indazolyl, benzoimidazolyl, benzooxazolyl, 1,2-benzoisooxazolyl, benzothiazolyl, 1,2-benzoisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenoxazinyl, phenothiazinyl, phenazinyl, phenoxatinyl, thianthrenyl, phenanthredinyl, phenanthrolinyl, indolizinyl, pyrrolo[1,2-b]pyridazinyl, pyrazo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl, etc.), and the like.

Preferred examples of the non-aromatic heterocyclic group as the substituent of the hydrocarbon group, the acyl group, the sulfonyl group, the sulfinyl group and the heterocyclic group represented by $R^1$ or $R^2$ include a 5- to 8-membered non-aromatic, monocyclic heterocyclic group containing 1 to 4 heteroatoms selected from nitrogen, sulfur, and oxygen atoms, such as oxiranyl, azetidinyl, oxetanyl, thietanyl, pyrrolidinyl, tetrahydrofuryl, thiolanyl, piperidinyl, tetrahydropyranyl, morpholinyl, thiomorpholinyl, piperazinyl, and the like.

Examples of the halogen atom as the substituent of the hydrocarbon group, the acyl group, the sulfonyl group, the sulfinyl group and the heterocyclic group represented by $R^1$ or $R^2$ include fluorine, chlorine, bromine, and iodine, with fluorine and chlorine being particularly preferred.

Examples of the optionally substituted amino group as the substituent of the hydrocarbon group, the acyl group, the sulfonyl group, the sulfinyl group and the heterocyclic group represented by $R^1$ or $R^2$ include amino group, an N-monosubstituted amino group, and N,N-disubstituted amino group. Examples of said substituted amino groups include an amino group having one or two $C_{1-10}$ alkyl groups, $C_{3-7}$ cycloalkyl groups, $C_{2-10}$ alkenyl groups, $C_{2-10}$ alkynyl groups $C_{3-7}$ cycloalkenyl groups, $C_{6-14}$ aryl groups that may have a $C_{1-4}$ alkyl group, a heterocyclic group (e.g., the same heterocyclic group as that as the substituent of the hydrocarbon group, the acyl group, the sulfonyl group, and the heterocyclic group represented by $R^1$ or $R^2$), or $C_{1-10}$ acyl groups (e.g. $C_{3-7}$ alkanoyl, etc.) as the substituents thereof (e.g., methylamino, dimethylamino, ethylamino, diethylamino, dibutylamino, diallylamino, cyclohexylamino, phenylamino, N-methyl-N-phenylamino, acetylamino, propionylamino, benzoylamino, nicotinoylamino, etc.). In addition, the two groups in said substituted amino group may be combined to form a nitrogen-containing, 5- to 7-membered ring (e.g., the same ring as that formed by combining $R^1$ and $R^2$ each other, preferably, piperidine, morpholino, thiomorpholino, etc.).

Further, the carbamoyl group and the sulfamoyl group as the substituent of the hydrocarbon group, the acyl group, the sulfonyl group, the sulfinyl group and the heterocyclic group represented by $R^1$ or $R^2$ may have the same one or two substituents as those of the above-mentioned substituted amino group.

Examples of the optionally substituted acyl group as the substituent of the hydrocarbon group, the acyl group, the sulfonyl group, the sulfinyl group and the heterocyclic group represented by $R^1$ or $R^2$ include (i) formyl or (ii) a group where the carbonyl group is combined with a $C_{1-10}$ alkyl group, a $C_{2-10}$ alkenyl group, a $C_{2-10}$ alkynyl group, a $C_{3-7}$ cycloalkyl group, a $C_{5-7}$ cycloalkenyl group, or an aromatic group (e.g., phenyl group, pyridyl group, etc.) (e.g., acetyl, propionyl, butyryl, isobytyryl, valeryl, isovaleryl, pivaloyl, hexanoyl, heptanoyl, octanoyl, cyclobutanecarbonyl, cyclopentanecarbonyl, cyclohexanecarbonyl, cycloheptanecarbonyl, crotonyl, 2-cyclohexenecarbonyl, benzoyl, etc.) and the like.

Examples of the optionally substituted hydroxyl group as the substituent of the hydrocarbon group, the acyl group, the sulfonyl group, the sulfinyl group and the heterocyclic group represented by $R^1$ or $R^2$ include hydroxyl group and a hydroxyl group having an appropriate substituent, particularly, that to be used as a protective group (e.g., alkoxy, alkenyloxy, alkynyloxy, aralkyloxy, acyloxy, aryloxy, etc.).

As the preferred alkoxy, there is $C_{1-10}$ alkoxy (e.g., methoxy, ethoxy, propoxy, isopropoxy, butoxy, isobutoxy, sec-butoxy, tert-butoxy, pentyloxy, isopentyloxy, neopentyloxy, hexyloxy, heptyloxy, nonyloxy, etc.), $C_{3-7}$ cycloalkyloxy (e.g., cyclobutoxy, cyclopentyloxy, cyclohexyloxy, etc.).

As the preferred alkenyloxy, there is $C_{2-10}$ alkenyloxy (e.g., allyloxy, crotyloxy, 2-pentenyloxy, 3-hexenyloxy, etc.) or $C_{3-7}$ cycloalkyloxy (e.g., 2-cyclopentenylmethoxy, 2-cyclohexenylmethoxy, etc.).

As the preferred alkynyloxy, there is $C_{2-10}$ alkynyloxy (e.g., ethynyloxy, 2-propinyloxy, etc.).

As the preferred aralkyloxy, there is, for example, phenyl-$C_{1-4}$ alkyloxy (e.g., benzyloxy, phenethyloxy, etc.).

As the preferred acyloxy, there is $C_{3-4}$ alkanoyloxy (e.g., acetyloxy, propionyloxy, butyryloxy, isobutyryloxy, etc.), $C_{3-4}$ alkenoyloxy, or $C_{3-4}$ alkynoyloxy.

As the preferred aryloxy, there is phenoxy, a phenoxy optionally substituted with a halogen atom such as 4-chlorophenoxy, or the like.

Examples of the optionally substituted thiol group as the substituent of the hydrocarbon group, the acyl group, the sulfonyl group, the sulfinyl group and the heterocyclic group represented by $R^1$ or $R^2$ include thiol group and a thiol group having an appropriate substituent, particularly, that to be used as a protective group (e.g., alklythio, alkenylthio, alkynylthio, aralkylthio, acylthio, arylthio, etc.), and examples of said substituent include the same substituent as that of the optionally substituted hydroxyl group.

Examples of the optionally esterified carboxyl group as the substituent of the hydrocarbon group, the acyl group, the sulfonyl group, the sulfinyl group and the heterocyclic group represented by $R^1$ or $R^2$ include, in addition to carboxyl group, an alkyloxycarbonyl group, an alkenyloxycarbonyl, an alkynyloxycarbonyl, an aralkyloxycarbonyl group, an acyoxycarbonyl group, an aryloxycarbonyl group, and the like.

Examples of the alkyl group in said alkyloxycarbonyl group include a $C_{1-6}$ alkyl group (e.g., methyl, ethyl, propyl, isopropyl, butyl, isobutyl, sec-butyl, tert-butyl, etc.).

Examples of the alkenyl group in said alkenyloxycarbonyl group include a $C_{2-6}$ alkenyl group (e.g., vinyl, allyl, isopropenyl, 1-propenyl, 1-butenyl, 2-butenyl, 3-methylallyl, etc.).

Examples of the alkynyl group in said alkynyloxycarbonyl group include a $C_{2-6}$ alkynyl group (e.g., ethynyl, 2-propynyl, etc.).

The aralkyl group in said aralkyloxycarbonyl group means an aryl-alkyl group (e.g., $C_{6-10}$ aryl-$C_{3-6}$ alkyl, etc.). The aryl group in said aryl-alkyl group means a monocyclic or condensed polycyclic aromatic hydrocarbon group, and preferred examples include phenyl, naphthyl, anthryl, phenanthryl, acenaphthenyl, and the like. They may have a substituent such as a $C_{1-10}$ alkyl group, a $C_{2-10}$ alkenyl group, a $C_{2-10}$ alkynyl group, a $C_{3-8}$ cycloalkyl group, a $C_{3-8}$ cycloalkenyl group, a $C_{4-8}$ cycloalkadienyl group, an aryl group (e.g., $C_{6-14}$ aryl, etc.), an aromatic heterocyclic group (e.g., the same aromatic heterocyclic group as that of the substituent of the hydrocarbon group, the acyl group, the sulfonyl group, the sulfinyl group and the heterocyclic group represented by $R^1$ or $R^2$, etc.), a non-aromatic heterocyclic group (e.g., the same non-aromatic heterocyclic group as that of the substituent of the hydrocarbon group, the acyl group, the sulfonyl group, the sulfinyl group and the heterocyclic group represented by $R^1$ or $R^2$, etc.), an aralkyl group (e.g., a $C_{6-14}$ aryl-$C_{1-6}$ alkyl group, etc.), amino group, an N-mono-substituted amino group (e.g., the same N-mono-substituted amino group as that of the substituent of the hydrocarbon group, the acyl group, the sulfonyl group, the sulfinyl group and the heterocyclic group represented by $R^1$ or $R^2$, preferably a N-mono-$C_{1-4}$ alkylamino group, etc.), a N,N-disubstituted amino group (e.g., the same N,N-disubstituted amino group as that of the substituent in the hydrocarbon group, the acyl group, the sulfonyl group, the sulfinyl group and the heterocyclic group represented by $R^1$ or $R^2$, preferably a N,N-di-$C_{1-4}$ alkylamino group, etc.), amidino group, an acyl group (e.g., the same acyl group as that of the substituent of the hydrocarbon group, the acyl group, the sulfonyl group, the sulfinyl group and the heterocyclic group represented by $R^1$ or $R^2$, etc.), carbamoyl group, a N-mono-substituted carbamoyl group (e.g., a N-mono-$C_{1-4}$ alkylcarbamoyl group such as methylcarbamoyl, ethylcarbamoyl, etc.; phenylcarbamoyl; etc.), a N,N-disubstituted carbamoyl group (a N,N-di-$C_{1-4}$ alkylcarbamoyl group such as N,N-dimethylcarbamoyl, N,N-diethylcarbamoyl, etc.; piperidinocarbamoyl; morpholinocarbamoyl; etc.), sulfamoyl group, a N-monosubstituted sulfamoyl group (e.g., a N-mono-$C_{1-4}$ alkylsulfamoyl group such as methylsulfamoyl, ethylsulfamoyl, etc.; phenylsulfamoyl; p-toluenesulfamoyl; etc.), a N,N-disubstituted sulfamoyl group (e.g., a N,N-disubstituted $C_{1-4}$ alkylsulfamoyl group such as N,N-dimethylsulfamoyl, etc.; a N—$C_{1-4}$ alkyl-N-phenylsulfamoyl group such as N-methyl-N-phenylsulfamoyl, etc.; piperidinosulfamoyl; morpholinosulfamoyl; etc.), carboxyl group, a $C_{1-10}$ alkoxycarbonyl group (e.g., methoxycarbonyl, ethoxycarbonyl, isopropoxycarbonyl, sec-butoxycarbonyl, isobutoxycarbonyl, tert-butoxycarbonyl, etc.), hydroxyl group, a $C_{1-10}$ alkoxy group, a $C_{2-10}$ alkenyloxy group, a $C_{3-7}$ cycloalkyloxy group, an aralkyloxy group (e.g., $C_{6-14}$ aryl-$C_{1-6}$ alkyloxy, etc.), an aryloxy group (e.g., $C_{6-14}$ aryloxy, etc.), mercapto group, a $C_{1-10}$ alkylthio group, an aralkylthio group (e.g., $C_{6-14}$ aryl-$C_{1-6}$ alkylthio, etc.), an arylthio group (e.g., $C_{6-14}$, arythio, etc.), sulfo group, cyano group, azido group, nitro group, nitroso group, a halogen atom, or the like. As for an alkyl group in said aryl-alkyl group, a $C_{1-6}$ alkyl group (e.g., methyl, ethyl, propyl, butyl, etc.) is preferred. Preferred examples of said aralkyl group, i.e., an aryl-alkyl group include benzyl, phenethyl, 3-phenylpropyl, (1-naphthyl)methyl, (2-naphthyl)methyl, and the like. Among them, benzyl, phenethyl, and the like are preferred.

As the acyl group in said acyloxycarbonyl group, for example, there are formyl, a $C_{2-4}$ alkanoyl group, a $C_{3-4}$ alkenoyl group, a $C_{3-4}$ alkynoyl group, and the like.

As the aryl group in said aryloxycarbonyl group, for example, there are phenyl, naphthyl, and the like.

Examples of the amidated carboxyl group as the substituent of the hydrocarbon group, the acyl group, the sulfonyl group, the sulfinyl group and the heterocyclic group represented by $R^1$ or $R^2$ include the carboxyl group amidated with an optionally substituted amino group as the substituent of the hydrocarbon group, the acyl group, the sulfonyl group, and the heterocyclic group represented by the above mentioned $R^1$ or $R^2$, each of which may be substituted.

In the above-mentioned formula (I), examples of the heterocyclic group of the optionally substituted heterocyclic group represented by R include the same heterocyclic group as that defined with respect to the above-mentioned $R^1$ or $R^2$. The optionally substituted heterocyclic group represented by R may be attached to the adjacent X through any possible atom (e.g., nitrogen, carbon) in the heterocyclic group. It is preferred that the optionally substituted heterocyclic group represented by R is attached to X through nitrogen atom.

Examples of the heterocyclic group of the optionally substituted heterocyclic group represented by R (preferably, a nitrogen-containing heterocyclic group) include (i) a 5- to 7-membered heterocyclic group containing one sulfur atom, one nitrogen atom, or one oxygen atom, (ii) a 5- to 7-membered heterocyclic group containing 2 to 4 nitrogen atoms, or (iii) a 5- to 7-membered heterocyclic group containing 1 to 2 nitrogen atoms and one sulfur atom or one oxygen atom, or (iv) these heterocyclic groups may be condensed with a 5- to 6-membered ring containing 2 or less nitrogen atoms, benzene ring, or a 5-membered ring containing one sulfur atom. Each of the heterocyclic groups exemplified in (i) to (iv) may be a saturated or unsaturated heterocyclic group, and the unsaturated heterocyclic group may be either aromatic or non-aromatic.

These heterocyclic groups may have 1 to 3 substituents at any possible positions. Examples of such a substituent include the same substituent as that defined with respect to the substituent of the hydrocarbon group, the acyl group, the sulfonyl group, the sulfinyl group and the heterocyclic group represented by $R^1$ or $R^2$ (preferably, oxo group), or the like.

Specific examples of the optionally substituted heterocyclic group represented by R, in the case where the constituent carbon atom in the heterocyclic group is attached to the adjacent X, include 2-imidazolyl, 1,2,4-triazol-3-yl, 2-thiazolyl, 2-oxazolyl, 2-pyridyl, 3-pyridyl, 4-pyridyl, 2-benzoimidazolyl, and the like.

Examples of the optionally substituted heterocyclic group represented by R, in the case where the constituent nitrogen atom in the heterocyclic group is attached to the adjacent X, include 1-pyrrolyl, 1-pyrrolidinyl, 1-imidazolidinyl, 1-pyrazolidinyl, 1-piperidyl (piperidino), 1-piperazinyl, 4-morpholinyl (morpholino), 4-thiomorpholinyl, homopiperazin-1-yl, pyrazol-1-yl, imidazol-1-yl, 1,3-thiadiazol-3-yl, 1,3-oxadiazol-3-yl, 1,2,4-triazol-1-yl, 1,2,4-triazol-2-yl, 1,2,4-triazol-4-yl, 1,2,3-triazol-1-yl, 1,2,3-triazol-2-yl, tetrazol-1-yl, oxazol-3-yl, thiazol-3-yl, and partly or whole saturated, nitrogen-containing, heterocyclic groups thereof. These heterocyclic groups may have the 1 to 3 same substituent as the optional substituent of the hydrocarbon group, the acyl group, the sulfonyl group, the sulfinyl group and the heterocyclic group represented by $R^1$ and $R^2$, and may be condensed with the above-mentioned non-aromatic, monocyclic heterocyclic group or aromatic ring such as benzene ring or the like. Specific examples, in the case where the heterocyclic group is condensed with an aromatic ring, include benzimidazol-1-yl, indol-1-yl, 1H-indazol-1-yl, and the like; preferably, 1,2,4-triazol-1-yl, 1,2,4-triazol-2-yl, imidazol-1-yl, morpholino (4-morpholinyl), piperidino (1-piperidyl), oxazolidin-3-yl, thiazolidin-3-yl, hydantoin-1-yl, pyrrolidino (1-pyrrolidin-1-yl), and the like, each of which may be substituted and may be condensed with benzene ring; more preferably, a nitrogen-containing, 5- to 7-membered ring that may have 1 to 2 oxo groups (e.g., 2,4-dioxooxazolidin-3-yl, 2,4-dioxothiazolidin-3-yl, 2,5-dioxohydantoin-1-yl, 2,5-dioxopyrrolidin-1-yl, etc.), with 2,5-dioxopyrrolidin-1-yl being particularly preferred.

R is preferably

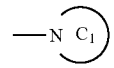

wherein ring $C_1$ represents a 5- to 7-membered heterocyclic group which may contain 1 to 3 hetero atoms selected from nitrogen, sulfur and oxygen in addition to the nitrogen atom, and may be substituted with the 1 to 3 same substituents of the hydrocarbon group, the acyl group, the sulfonyl group, the sulfinyl group and the heterocyclic group represented by $R^1$ and $R^2$.

More preferably, R is

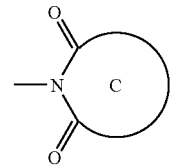

wherein ring C represents a 5- to 7-membered heterocyclic group which may contain one or more (1 to 3, preferably 1) hetero atoms selected from nitrogen, sulfur and oxygen, in addition to the nitrogen atom.

In the above formula (I), Y is oxygen atom, an optionally oxidized sulfur atom, or

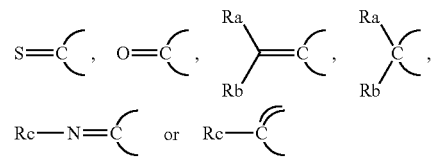

(wherein Ra and Rb, which may be the same or different, respectively, represent hydrogen atom, a halogen atom, an optionally substituted hydrocarbon group, an optionally substituted acyl group, an optionally substituted carbamoyl group, an optionally substituted thiocarbamoyl group, an optionally substituted sulfonyl group, an optionally substituted sulfinyl group, an optionally substituted hydroxyl group, an optionally substituted thiol group, an optionally esterified carboxyl group, or an optionally substituted heterocyclic group, or Ra and Rb may be combined each other to form a 5- to 7-membered ring; and Rc represents hydrogen atom, a halogen atom, an optionally substituted hydrocarbon group, an optionally substituted acyl group, an optionally substituted carbamoyl group, an optionally substituted thiocarbamoyl group, an optionally substituted sulfonyl group, an optionally substituted sulfinyl group, an optionally substituted hydroxyl group, an optionally substituted thiol group, an optionally esterified carboxyl group, or an optionally substituted heterocyclic group).

Examples of the optionally substituted hydrocarbon group represented by Ra, Rb, or Rc include the same group as the optionally substituted hydrocarbon group represented by the above-mentioned $R^1$ or $R^2$. Among them, methyl, ethyl, isopropyl, propyl, butyl, benzyl, phenethyl, 2-, 3-, or 4-pyridylmethyl, or the like is preferred as the optionally substituted hydrocarbon group represented by Ra, Rb, or Rc.

Examples of the optionally substituted acyl group represented by Ra, Rb, or Rc include the same group as the optionally substituted acyl group represented by the above-mentioned $R^1$ or $R^2$. In particular, benzoyl, acetyl or the like is preferred.

Examples of the optionally substituted carbamoyl group represented by Ra, Rb, or Rc include the same group as the optionally substituted carbamoyl group defined with respect to the substituent of the hydrocarbon group, acyl group, sulfonyl group, or heterocyclic group represented by the above-mentioned $R^1$ or $R^2$.

Examples of the optionally substituted thiocarbamoyl group represented by Ra, Rb, or Rc include the same group as the optionally substituted thiocarbamoyl group defined with respect to the substituent of the optionally substituted hydrocarbon group, acyl group, sulfonyl group, or heterocyclic group represented by the above-mentioned $R^1$ or $R^2$.

Examples of the optionally substituted sulfonyl group represented by Ra, Rb, or Rc include the same group as the optionally substituted sulfonyl group represented by the above-mentioned $R^1$ or $R^2$.

Examples of the optionally substituted sulfinyl group represented by Ra, Rb, or Rc include the same group as the optionally substituted sulfinyl group represented by the above-mentioned $R^1$ or $R^2$.

Examples of the optionally substituted hydroxyl group represented by Ra, Rb, or Rc include the same group as the optionally substituted hydroxyl group defined with respect to the substituent of the hydrocarbon group, acyl group, sulfonyl group, the sulfinyl group or heterocyclic group represented by the above-mentioned $R^1$ or $R^2$.

Examples of the optionally substituted thiol group represented by Ra, Rb, or Rc include the same group as the optionally substituted thiol group defined with respect to the substituent of the hydrocarbon group, acyl group, sulfonyl group, the sulfinyl group or heterocyclic group represented by the above-mentioned $R^1$ or $R^2$.

Examples of the optionally substituted, esterified carboxyl group represented by Ra, Rb, or Rc include the same group as the optionally substituted, esterified carboxyl group defined with respect to the substituent of the hydrocarbon group, the acyl group, the sulfonyl group, the sulfinyl group or the heterocyclic group represented by the above-mentioned $R^1$ or $R^2$.

Examples of the optionally substituted heterocyclic group represented by Ra, Rb, or Rc include the same group as the optionally substituted heterocyclic group defined with respect to the above-mentioned $R^1$ or $R^2$.

Also, examples of the 5- to 7-membered ring, in the case where Ra and Rb are combined each other to form the 5- to 7-membered ring, include a $C_{3-7}$ saturated hydrocarbon ring (e.g., cyclopentane, cyclohexane, and cycloheptane) or a 5- to 7-membered, saturated heterocyclic group containing one to four heteroatoms selected from nitrogen, sulfur, and oxygen [e.g., nitrogen-containing, $C_{3-7}$ saturated hydrocarbon ring (e.g., tetrahydrofuran, tetrahydropyran, pyrrolidine, piperidine), oxygen-containing, $C_{5-7}$ saturated hydrocarbon (e.g., dioxolan, dioxane, dioxepane ring), etc.], preferably a $C_{5-7}$ saturated hydrocarbon ring (e.g., cyclopentane, cyclohexane, cycloheptane) or an oxygen-containing, $C_{5-7}$ saturated hydrocarbon ring (e.g., dioxolan, dioxane, dioxepane ring), or the like.

Preferred examples of Rc include hydrogen atom, hydroxyl group, methoxy group, ethoxy group, and the like.

Preferred examples of Y include an optionally substituted sulfur atom, or

In the above-mentioned formula (I), when ring B represents to form a Y-containing optionally substituted 5- to 8-membered (preferably 6-membered) ring whose ring constituent atoms contain no nitrogen atom together with the carbon-double bond portion in the adjacent thiophene ring. Also, ring B may form a Y-containing lactone ring in the case where Y is

As the 5- to 8-membered ring in the Y-containing optionally substituted 5- to 8-membered ring whose ring constituent atoms contain no nitrogen atom, for example, there is:

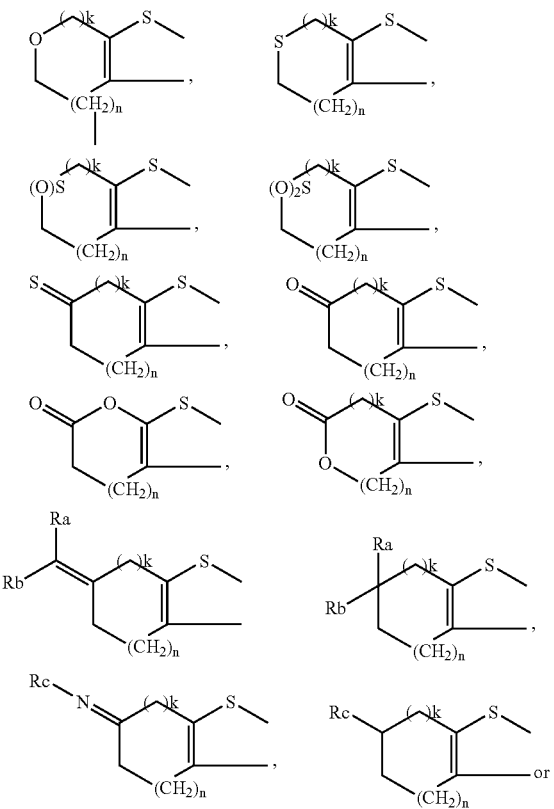

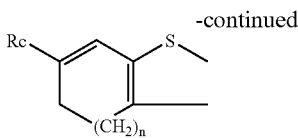

wherein Ra, Rb, and Rc are as defined above; n is an integer of 0 to 4; and k is an integer of 0 to 4 (where the sum of n and k is 1 to 4); preferably, n and k represent 1, or the like as well as a ring a part or the whole of which is converted to an unsaturated bond, or the like, i.e., a ring represented by

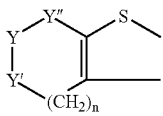

each of Y' and Y" represents carbon, sulfur or oxygen (preferably, carbon) atom; and Y and n are as defined above.

More preferred examples include:

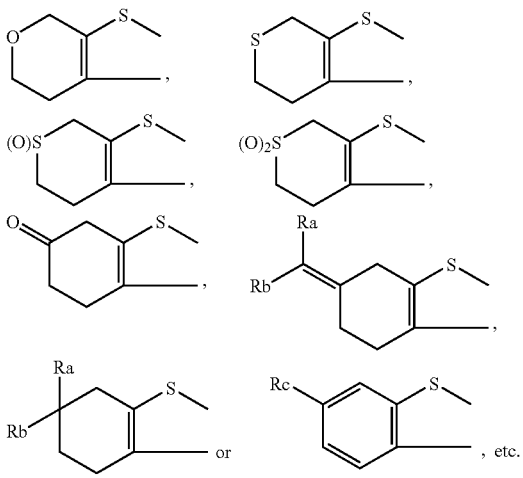

Further, in the above formula, the compound wherein at least one of Y' or Y" represents nitrogen atom, for example,

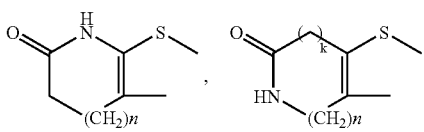

wherein each symbol is as defined above, or a salt thereof can be produced by the process as described hereinafter and has the activities as described hereinafter.

The Y-containing optionally substituted. 5- to 8-membered ring whose ring constituent atoms contain no nitrogen atom may further have 1 to 4 substituents other than the substituent shown with respect to the Y portion, for example, the 1 to 4 same substituents as those defined with respect to the substituent of the heterocyclic group of $R^1$ or $R^2$; preferably, those selected from an aliphatic-chain hydrocarbon group [e.g., an alkyl group (preferably, a $C_{1-10}$ alkyl group), an alkenyl group (preferably, a $C_{2-10}$ alkenyl group), an alkynyl group (preferably, a $C_{2-10}$ alkynyl group), an optionally substituted acyl group, a halogen atom, etc.; more preferably, a $C_{1-10}$ alkyl group (particularly, a $C_{1-6}$ alkyl group) and a halogen atom (e.g., chlorine, bromine, iodine, or fluorine).

In the above-mentioned formula (I), ring A may have, at any possible position on its ring, 1 to 4, preferably one or two, more preferably one, substituents that may be the same or different. As for said substituent on ring A, there is employed, for example, a halogen atom, nitro group, an optionally substituted alkyl group, an optionally substituted hydroxyl group, an optionally substituted thiol group, an optionally substituted amino group, an optionally substituted acyl group, an optionally esterified carboxyl group, or an optionally substituted aromatic ring group.

Examples of the halogen atom as the substituent on ring A include fluorine, chlorine, bromine, and iodine.

Examples of the alkyl group of the optionally substituted alkyl group as the substituent on ring A include any of a $C_{1-10}$ straight chain alkyl group, a $C_{3-10}$ branched chain alkyl, and a $C_{3-10}$ cyclic alkyl, for example, methyl, ethyl, propyl, isopropyl, butyl, isobutyl, sec-butyl, tert-butyl, pentyl, isopentyl, neopentyl, hexyl, heptyl, octyl, nonyl, decyl, cyclopropyl, cyclobutyl, cyclopentyl, cyclohexyl, cycloheptyl, or the like.

Examples of the substituent in the optionally substituted alkyl group as the substituent on ring A include the same substituent as that defined with respect to the hydrocarbon group, acyl group, sulfonyl group, the sulfiniyl group or heterocyclic group represented by the above-mentioned $R^1$ or $R^2$.

Examples of the optionally substituted hydroxyl group as the substituent on ring A include an optionally substituted hydrocarbon group, an optionally substituted acyl group, an optionally substituted carbamoyl group, an optionally substituted sulfonyl group, an optionally substituted sulfinyl group, an optionally substituted heterocyclic group or an optionally esterified carboxy group.

Examples of the substituents of the optionally substituted hydrocarbon group, the optionally substituted acyl group, the optionally substituted sulfonyl group, the optionally substituted sulfinyl group and the optionally substituted heterocyclic group include the same substituents as those of the optionally substituted hydrocarbon group, the optionally substituted acyl group, the optionally substituted sulfonyl group, the optionally substituted sulfinyl group or the optionally substituted heterocyclic group represented by the above-mentioned $R^1$ or $R^2$. Further, examples of the optionally substituted carbamoyl group and the optionally esterified carboxy group include the same groups as those defined with respect to the substituents of the optionally substituted hydrocarbon group, the optionally substituted acyl group, the optionally substituted sulfonyl group, the optionally substituted sulfinyl group or the optionally substituted heterocyclic group represented by the above-mentioned $R^1$ or $R^2$.

As the optionally substituted hydroxyl group as the substituent of ring A, preferably, there is a $C_{1-6}$ alkoxy group or hydroxyl group, more preferably a $C_{1-6}$ alkoxy group, most preferably a $C_{1-3}$ alkoxy group, and particularly, methoxy group.

Examples of the optionally substituted thiol group as the substituent of ring A include the same optionally substituted thiol group as that defined with respect to the substituent of the hydrocarbon group, the acyl group, the sulfonyl group, the sulfinyl group or the heterocyclic group represented by the above-mentioned $R^1$ or $R^2$.

Examples of the optionally substituted amino group as the substituent of ring A include the same optionally substituted amino group as that defined with respect to the substituent of the hydrocarbon group, the acyl group, the sulfonyl group, the sulfinyl group or the heterocyclic group represented by the above-mentioned $R^1$ or $R^2$.

Examples of the optionally substituted acyl group as the substituent of ring A include the same optionally substituted acyl group as that represented by the above-mentioned $R^1$ or $R^2$.

Examples of the optionally esterified carboxyl group as the substituent of ring A include the same optionally esterified carboxyl group as that defined with respect to the substituent of the hydrocarbon group, the acyl group, the sulfonyl group, the sulfinyl group or the heterocyclic group represented by the above-mentioned $R^1$ or $R^2$.

Examples of the optionally substituted aromatic ring as the substituent on ring A include a $C_{6-14}$ aromatic hydrocarbon group such as phenyl, naphthyl, anthryl, or the like as well as a 5- to 7-membered hetero-aromatic residue having heteroatoms(s) selected from nitrogen, sulfur, and oxygen, such as pyridyl, furyl, thienyl, imidazolyl, thiazolyl, or the like.

The substituent(s) on ring A are located preferably at the 3-position and/or 4-position on ring A. In the case where these substituents on ring A are adjacent each other, the adjacent substituents may be combined to form a ring represented by —$(CH_2)_m$— or —O—$(CH_2)_l$—O— [wherein, m represents an integer of 3 to 5 and l represents an integer of 1 to 3]. Such a ring includes a 5- to 7-membered ring that is formed with the carbon atoms in the benzene ring.

It is preferred that ring A is substituted with at least one optionally substituted hydroxyl group, preferably a $C_{1-6}$ alkoxy group or hydroxyl group, more preferably a $C_{1-6}$ alkoxy group, most preferably a $C_{1-6}$ alkoxy group, in particular, methoxy group. More preferably, ring A is substituted with one optionally substituted hydroxyl. Specifically, for example, it is preferred that the 4-position in ring A is substituted with an optionally substituted hydroxyl group (particularly, methoxy group).

Preferred examples of the compound represented by the above-mentioned formula (I) include a compound, wherein alk is methylene, G is a halogen atom such as chlorine atom, etc., X is —$(CH_2)_q$— (q represents an integer of 0 to 5), R is an optionally substituted amino group; ring B is an optionally substituted 5- to 8-membered ring containing Y, Y is an optionally substituted sulfur atom or

and ring A is substituted with a $C_{1-6}$ alkoxy group or hydroxyl group, a prodrug thereof or a salt thereof; more preferably a compound, wherein alk is methylene, G is a halogen atom such as chlorine atom, etc., X is —$(CH_2)_q$— (q represents 0, i.e., a bond), R is

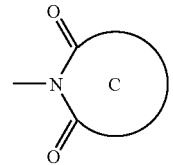

(wherein C is as defined above), ring B is a ring represented by

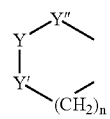

[wherein Y' and Y" represent carbon, sulfur, oxygen atom (preferably carbon), respectively and Y and n are as defined above (preferably an optionally oxidized sulfur atom or

n is as defined above (preferably 1)] which may be substituted with 1 to 4 substituents selected from a $C_{1-6}$ alkyl group and a halogen atom, and ring A is substituted with a $C_{1-6}$ alkoxy group or hydroxyl group (preferably substituted with a $C_{1-6}$ alkoxy group at the 4-position in ring A), a prodrug thereof or a salt thereof.

Preferably examples of such a compound include;

3-{[3-chloro-4-(4-methoxyphenyl)-7-oxido-5,8-dihydro-6H-thiopyrano[4',3':4,5]thieno[2,3-b]pyridin-2-yl]methyl}-1,3-thiazolidine-2,4-dione, an optically active substance thereof or a salt thereof;

3-{[3-chloro-4-(4-methoxyphenyl)-7-oxido-5,8-dihydro-6H-thiopyrano[4',3':4,5]thieno[2,3-b]pyridin-2-yl]methyl}-1,3-oxazolidine-2,4-dione, an optically active substance thereof or a salt thereof;

1-{[3-chloro-4-(4-methoxyphenyl)-7-oxido-5,8-dihydro-6H-thiopyrano[4',3':4,5]thieno[2,3-b]pyridin-2-yl]methyl}-2,5-pyrrolidinedione, an optically active substance thereof or a salt thereof;

1-{[3-chloro-4-(4-methoxyphenyl)-7-oxo-5,6,7,8-tetrahydro[1]benzothieno[2,3-b]pyridin-2-yl]methyl}-(2,5-pyrrolidinedione or a salt thereof;

1-{[3-chloro-4-(4-methoxyphenyl)-8,8-dimethyl-7-oxo-5,6,7,8-tetrahydro[1]benzothieno[2,3-b]pyridin-2-yl}methyl)-2,5-pyrrolidinedione or a salt thereof;

3-{[3-chloro-4-(4-methoxyphenyl)-8,8-dimethyl-7-oxo-5,6,7,8-tetrahydro[1]benzothieno[2,3-b]pyridin-2-yl]methyl}-1,3-thiazolidine-2,4-dione or a salt thereof;

1-{[3-chloro-4-(4-methoxyphenyl)-6,6-dimethyl-7-oxo-5,6,7,8-tetrahydro[1]benzothieno[2,3-b]pyridin-2-yl]methyl}-2,5-pyrrolidinedione or a salt thereof;

2-aminomethyl-3-chloro-4-(4-methoxyphenyl)-7-oxido-5,8-dihydro-6H-thiopyrano[4',3':4,5]thieno[2,3-b]pyridine, an optically active substance thereof or a salt thereof;

1-{[3-chloro-4-(4-hydroxyphenyl)-7,7-dioxido-5,8-dihydro-6H-thiopyrano[4',3':4,5]thieno[2,3-b]pyridin-2-yl]methyl}-2,5-pyrrolidinedione or a salt thereof;

4-{3-chloro-2-(2,5-dioxo-1-pyrrolidinyl)methyl]-7,7-dioxido-5,8-dihydro-6H-thiopyrano[4',3':4,5]thieno[2,3-b]pyridin-4-yl}phenyl diisobutyl phosphate or a salt thereof; or butyl 4-{3-chloro-2-[(2,5-dioxo-1-pyrrolidinyl)methyl]-7,7-dioxido-5,8-dihydro-6H-thiopyrano[4',3':4,5]thieno[2,3-b]pyridin-4-yl}phenyl carbonate or a salt thereof.

In addition, preferred examples of the compound represented by the above-mentioned formula (I) include a compound, wherein G is chloridne atom, X is —(CH$_2$)$_q$— (q represents an integer of 0 to 5.), R is an optionally substituted amino group, ring B is a Y containing optionally substituted 5- to 8-membered ring, Y is

(wherein, Ra and Rb, which may be the same or different, respectively, represent hydrogen atom, a halogen atom, an optionally substituted hydrocarbon group, an optionally substituted acyl group, an optionally substituted carbamoyl group, an optionally substituted thiocarbamoyl group, an optionally substituted sulfonyl group, an optionally substituted sulfinyl group, an optionally substituted hydroxyl group, an optionally substituted thiol group, an optionally esterified carboxyl group, or an optionally substituted heterocyclic group, or Ra and Rb may be combined each other to form a 5- to 7-membered ring), and ring A is substituted with a C$_{1-6}$ alkoxy group. Example of such a compound include:

3-chloro-2-[(2,5-dioxopyrrolidin-1-yl)methyl]-5,6,7,8-tetrahydro-7-oxo-4-(4-methoxyphenyl)[1]-benzothieno[2,3-b]pyridine ethylene ketal or a salt thereof, or the like.

As for a salt of the compound represented by the formula (I) in the present invention [hereinafter referred to as compound (I)] and a salt of the starting compound for the production of compound (I), a pharmaceutically acceptable salt is preferred. Examples thereof include a salt with an inorganic base, a salt with an organic base, a salt with an inorganic acid, a salt with an organic acid, a salt with a basic or acidic amino acid, and the like. Preferred examples of the salt with an inorganic base include alkali metal salts such as the sodium salt, the potassium salt, and the like; alkaline earth metal salts such as the calcium salt, the magnesium salt, and the like; as well as an aluminum salt, an ammonium salt, and the like. Preferred examples of the salt with an organic base include salts with trimethylamine, triethylamine, pyridine, picoline, ethanolamine, diethanolamine, triethanolamine, dicyclohexylamine, N,N'-dibenzylethylenediamine, and the like. Preferred examples of the salt with an inorganic acid include salts with hydrochloric acid, hydrobromic acid, nitric acid, sulfuric acid, phosphoric acid, and the like. Preferable examples of the salt with an organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, and the like. Preferable examples of the salt with a basic amino acid include salts with arginine, lysine, ornithine and the like. Preferable examples of the salt with an acidic amino acid include salts with aspartic acid, glutamic acid, and the like.

Compound (I) or its salt may be in the form of a prodrug thereof. The prodrug of compound (I) or its salt refers to a compound that is converted into compound (I) or its salt by a reaction with an enzyme, gastric acid, or the like under a physiological condition in the living body, namely, [1] a compound that is converted into compound (I) or its salt by an enzymatic oxidation, reduction, hydrolysis, or the like and [2] a compound that is converted into compound (I) or its salt by hydrolysis with gastric acid or the like. Examples of the prodrug of compound (I) or its salt include a compound or its salt, wherein the hydroxyl group in compound (I) or its salt is acylated, alkylated, phosphorylated, or converted into the borate (e.g., a compound or its salt, wherein the hydroxyl group in compound (I) or its salt is converted into acetyloxy, palmitoyloxy, propanoyloxy, pivaloyloxy, succinyloxy, fumaryloxy, alanyloxy, or dimethylaminomethylcarbonyloxy, etc.), a compound or its salt, wherein the carboxyl group in compound (I) or its salt is esterified or amidated (e.g., a compound or its salt or the like, wherein the carboxyl group in compound (I) or its salt is subjected to ethyl esterification, phenyl esterification, carboxyoxymethyl esterification, dimethylaminomethyl esterification, pivaloyloxymethyl esterification, ethoxycarbonyloxyethyl esterification, phthalidyl esterification, (5-methyl-2-oxo-1,3-dioxolan-4-yl)methyl esterification, cyclohexyloxycarbonyl esterification, or conversion into the methyl amide), and the like. These prodrugs can be produced according to a per se known method or its modified method.

Moreover, the prodrug of compound (I) or its salt may be a compound that is converted into compound (I) or its salt under a physiological condition as described in "Iyakuhin no Kaihatu (Development of Drugs)", Vol. 7, Bunishi Sekkei (Molecular Design), Hirokawa Shoten, 1990, pages 163–198.

Compound (I) or its salt may be labeled with an isotope (e.g., $^3$H, $^{14}$C, $^{35}$S, $^{125}$I, etc.) or the like.

When compound (I) of the present invention is a racemate, it can be separated into the corresponding (S)-form and (R)-form according to a conventional optical resolution method. The present invention includes each optically active substance (compound) and a racemate.

The above-mentioned compound (I) can be produced in the following manner. That is,

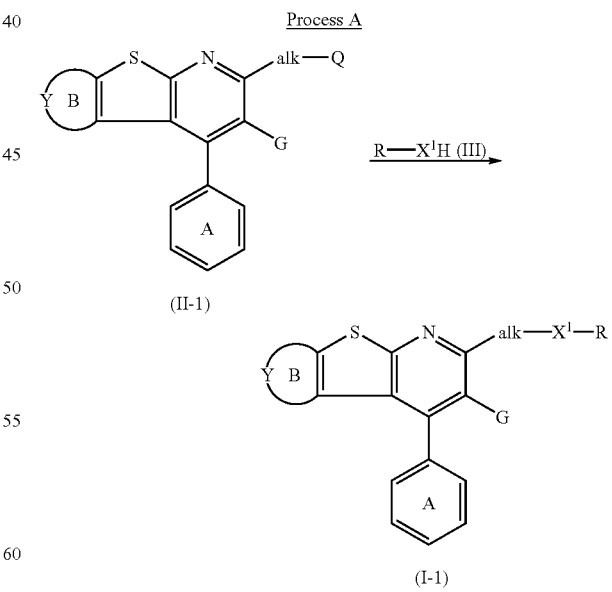

wherein alk represents an optionally substituted lower alkylene group; Q represents a leaving group; X$^1$ represents oxygen atom or an optionally oxidized sulfur atom; and the other symbols are as defined above.

In the general formula (II-1), examples of the leaving group represented by Q include halogen, preferably chlorine, bromine, or iodine, and a hydroxyl group activated by esterification such as a residue of organic sulfonic acid (e.g., p-toluenesulfonyloxy group, methansulfonyloxy group, etc.), a residue of organic phosphoric acid such as diphenylphosphoryloxy group, dibenzylphosphoryloxy group, dimethylphosphoryloxy group, and the like.

In this process, (II-1) is reacted with (III) in the presence of a base to produce (I-1). The reaction of (II-1) with (III) is carried out in an appropriate solvent. Examples of said solvent include aromatic hydrocarbon such as benzene, toluene, xylene, etc.; ether such as dioxane, tetrahydrofuran (THF), dimethoxyethane, or the like; alcohol such as methanol, ethanol, propanol, etc.; ethyl acetate; acetonitrile; pyridine; N,N-dimethylformamide (DMF); dimethyl sulfoxide (DMSO); chloroform; dichloromethane; 1,2-dichloroethane; 1,1,2,2,-tetrachloroethane; acetone; 2-butanone; and a mixture thereof. The reaction of (II-1) with (III) is carried out in the presence of an appropriate base such as an alkali metal salt, for example, sodium hydroxide, potassium hydroxide, potassium carbonate, sodium carbonate, sodium hydrogen carbonate, etc.; silver carbonate (Ag$_2$CO$_3$); sodium hydride; potassium hydride; an amine, for example, pyridine, triethylamine, N,N-dimethylaniline, 1,5-diazabicyclo[4.3.0]non-5ene, 1,4-diazabicyclo[2.2.2]octane, 1,8-diazabicyclo[5.4.0]undec-7-ene (DBU), etc.; or the like. The amount of the base to be used is preferably about 1–5 molar equivalents for compound (II-1). This reaction is carried out usually at –20° C. to 150° C., preferably –10° C. to 100° C.

The thus-obtained thienopyridine derivative (I-1) can be isolated and purified by a known separation and purification means, for example, concentration, concentration under reduced pressure, solvent extraction, crystallization, recrystallization, trans-solubilization, chromatography, and the like.

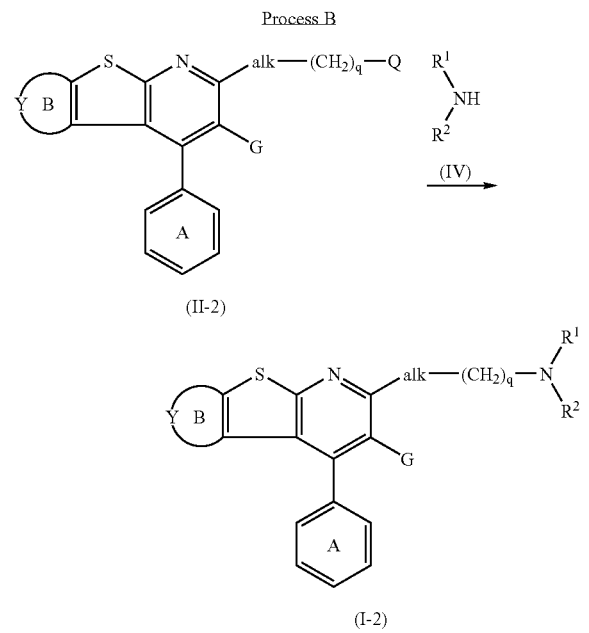

(II-2)

(I-2)

wherein each symbol is as defined above.

In this process, (II-2) is reacted with (IV) in the presence of a base to produce (I-2). The reaction of (II-2) with (IV) is carried out in an appropriate solvent. Examples of said solvent include aromatic hydrocarbon such as benzene, toluene, xylene, etc.; ether such as dioxane, tetrahydrofuran, dimethoxyethane, etc.; alcohol such as methanol, ethanol, propanol, etc.; ethyl acetate; acetonitrile; pyridine; N,N-dimethylformamide (DMF); dimethylacetamide (DMA); dimethyl sulfoxide (DMSO); 1-methyl-2-pyrrolidone; 1,3-dimethyl-2-imidazolidinone; chloroform; dichloromethane; 1,2.-dichloroethane; 1,1,2,2,-tetrachloroethane; acetone; 2-butanone; and a mixture thereof. The reaction of (II-2) with (IV) is carried out in the presence of an appropriate base such as an alkali metal salt, for example, sodium hydroxide, potassium hydroxide, potassium carbonate, sodium carbonate, sodium hydrogen carbonate, etc.; a metal alkoxide such as sodium methoxide, sodium ethoxide, sodium tert-butoxide, potassium tert-butoxide, etc.; an amine for example, pyridine, triethylamine, N,N-dimethylaniline, etc., sodium hydride; potassium hydride; or the like. The amount of the base to be used is preferably about 1–5 molar equivalents for compound (II-2). This reaction is carried out usually at –20° C. to 150° C., preferably –10° C. to 100° C. The present reaction, also, is carried out by using an excess amount of (IV) as the base.

The thus-obtained thienopyridine derivative (I-2) can be isolated and purified by a known separation and purification means such as concentration, concentration under reduced pressure, solvent extraction, crystallization, recrystallization, trans-solubilization, chromatography, and the like.

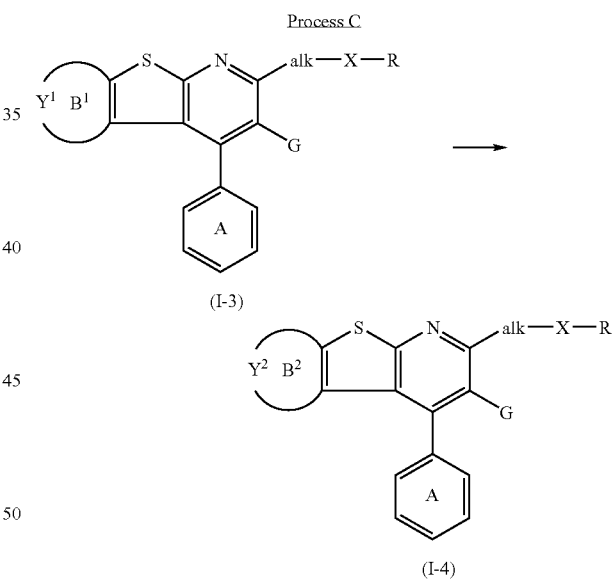

(I-3)

(I-4)

[wherein ring B$^1$ represents the formation of a Y$^1$-containing optionally substituted 5- to 8-membered ring whose ring constituent atoms contain no nitrogen atom; Y$^1$ represents sulfur atom or

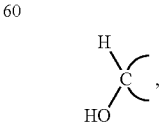

and the other symbols are as defined above.

In this process, (I-3) is subjected to oxidation to produce (I-4). This reaction is carried out in an appropriate solvent in the presence of an oxidizing agent or, if necessary, a catalyst. Examples of said solvent include a high polar aprotic solvent such as 1-methyl-2-pyrrolidone, 1,3-dimethyl-2-imidazolidinone, dimethylformamide, dimethylacetamide, dimethyl sulfoxide, etc.; aromatic hydrocarbon such as benzene, toluene, xylene, etc.; ether such as dioxane, tetrahydrofuran, dimethoxyethane, etc.; ethyl acetate; chloroform; dichloromethane; 1,2-dichloroethane; 1,1,2,2,-tetrachloroethane; and a mixture thereof. As the oxidizing agent, for example, there is hydrogen peroxide solution, peracetic acid, metachloroperbenzoic acid, cumene hydroperoxide, tert-butyl hydroperoxide, activated DMSO, manganese dioxide, nitric acid, or the like. As the catalyst, preferably, a complex containing a metal is used. Examples of the metal include vanadium, titanium, ruthenium, rhenium, tungsten, manganese, cobalt, etc. Among them, vanadium is preferred. Examples of the vanadium complex include vanadium oxides such as vanadium oxide acetylacetonate, vanadium oxide benzoylacetonate, vanadium oxide picolinate, vandium (V) oxide, vanadium (IV) oxide acetate, vanadium (IV) oxide sulfate hydrate, etc.; vanadium nitrides such as vanadium nitride; vanadium chlorides such as vanadium oxytrichloride, vanadium dichloride, vanadium tetrachloride, etc.; vanadium oxide trimethoxide; vanadium oxide triethoxide; vanadium oxide tri-n-propoxide; vanadium oxide triisopropoxide, vanadium tri-n-butoxide; vanadium oxide tri-sec-butoxide; vanadium oxide-t-butoxide; vanadium oxide β-hydroxyquinolyl; vanadium oxide β-hydroxypyridyl; and the like. The amount of the oxidizing agent is preferably an equivalent or an excess amount (for example, about 1–50 molar equivalents) for compound (I-3). Further, the amount of the catalyst to be used is 0.0000001 to 10 equivalents, preferably 0.0000005 to 1 equivalent for compound (I-3). This reaction is carried out usually at −70° C. to 150° C., preferably −60° C. to 120° C. and the reaction time is usually 1–100 hours.

The thus-obtained thienopyridine derivative (I-4) can be isolated and purified by a known separation and purification means such as concentration, concentration under reduced pressure, solvent extraction, crystallization, recrystallization, trans-solubilization, chromatography, and the like.

Process D

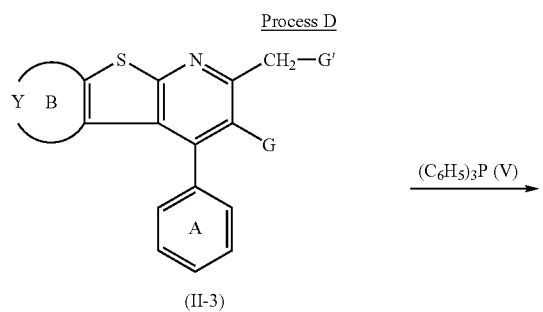

(II-3)

$(C_6H_5)_3P$ (V)

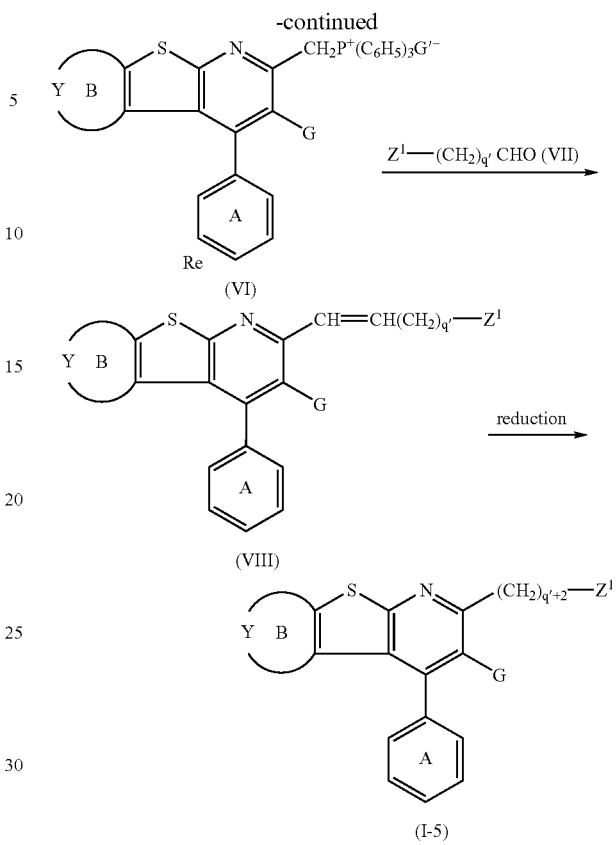

(I-5)

wherein $Z^1$ represents an optionally substituted heterocyclic group; q' represents an integer of 0 to 4; G' represents a halogen atom; and the other symbols are as defined above.

In this process, the compound represented by the general formula (II-3) is first reacted with a corresponding amount of triphenylphosphine to produce a phosphonium salt derivative represented by the general formula (VI). This reaction is carried out in a solvent and examples of said solvent include aromatic hydrocarbon such as benzene, toluene, xylene, etc.; ether such as tetrahydrofuran, dioxane, dimethoxyethane, etc.; acetonitrile; and a mixture thereof. This reaction is carried out at 10° C. to 200° C., preferably 30° C. to 150° C. for 0.5–50 hours.

Then, the phosphonium salt derivative (VI) and an aldehyde derivative (VII) are subjected to condensation reaction to produce (VIII). The condensation reaction of (VI) and (VII) is carried out in an appropriate solvent in the presence of a base. Examples of said solvent include alcohol such as methanol, ethanol, propanol, etc.; ether such as ethyl ether, dioxane, tetrahydrofuran, dimethoxyethane, etc.; aromatic hydrocarbon such as benzene, toluene, xylene, etc.; dichloromethane; 1,2-dichloroethane; N,N-dimethylformamide; dimethyl sulfoxide; and a mixture thereof. Examples of the base include an alkali metal hydride such as sodium hydride, potassium hydride, etc.; an alkoxide such as sodium ethoxide, sodium methoxide, potassium ethoxide, potassium tert.-butoxide, etc.; an organic lithium compound such as methyllithium, butyllithium, phenyllithium, etc.; sodium amide; and the like. The amount of the base to be used is preferably about 1–1.5 molar equivalents for compound (VI). This reaction is carried out usually at −50° C. to 100° C., preferably −20° C. to 50° C. The reaction time is 0.5–20 hours.

Although (VIII) is obtained as an isomeric mixture of the (E) form and the (Z) form with respect to the newly formed double bond, these (E) and (Z) forms, after separation into each isomer or as a mixture thereof without separation, are subjected to reduction to produce (I-5). This reduction is carried out by a conventional method in a solvent under an atmosphere of hydrogen in the presence of a catalyst such as a palladium catalyst (palladium-carbon, palladium black, etc.), a platinum catalyst (platinum dioxide, etc.), Raney nickel, or the like. Examples of said solvent include alcohol such as methanol, ethanol, propanol, etc.; ether such as ethyl ether, dioxane, tetrahydrofuran, dimethoxyethane, etc.; aromatic hydrocarbon such as benzene, toluene, xylene, etc.; dichloromethane; 1,2-dichloroethane; ethyl acetate; acetonitrile; acetone; 2-butanone; N,N-dimethylformamide; dimethyl sulfoxide; and a mixture thereof. The pressure of hydrogen atmosphere is 1–150 atmospheric pressure, preferably 1–20 atmospheric pressure. The thus-obtained thienopyridine derivative (I-5) can be isolated and purified according to a known separation and purification means such as concentration, concentration under reduced pressure, solvent extraction, crystallization, recrystallization, trans-solubilization, chromatography, and the like.

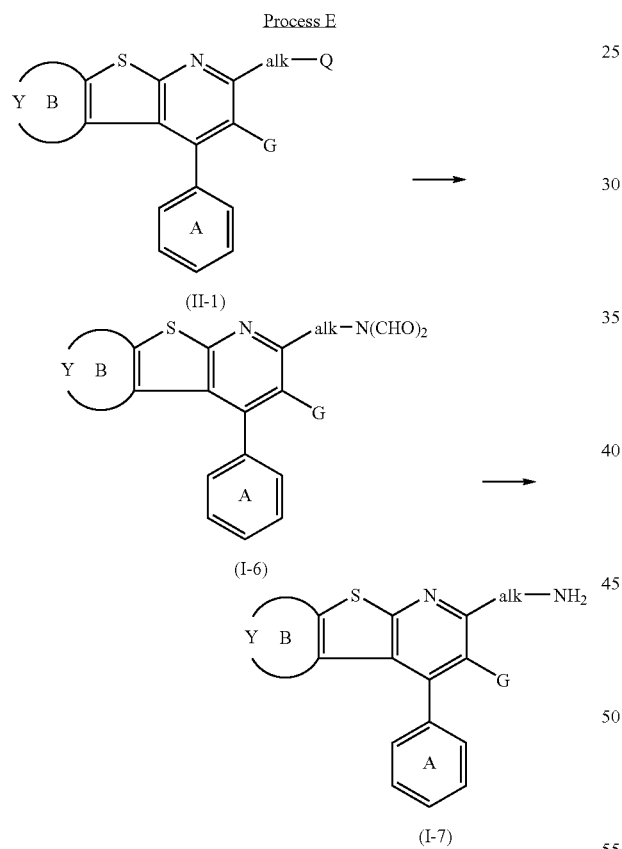

wherein each symbol is as defined above.

In this process, (II-1) is reacted with an alkali metal salt of diformylimide such as the sodium salt of diformylimide to be converted into a formylamino compound (I-6), which is then reacted with an acid to produce (I-7).

The reaction of compound (II-1) with an alkali metal salt of diformylimide such as the sodium salt of diformylimide is carried out in the same manner as that in Process A.

Compound (I-7) is produced by subjecting the formylamino compound (I-6) to hydrolysis in the presence of an acid. The hydrolysis of compound (I-6) is carried out in a water-containing solvent. Examples of said solvent include ether such as dioxane, tetrahydrofuran, dimethoxyethane, etc.; alcohol such as methanol, ethanol, propanol, butanol, 2-methoxyethanol, etc.; acetonitrile; N,N-dimethylformamide; dimethyl sulfoxide; acetone; 2-butanone; acetic acid; and a mixture thereof. The acid is, for example, hydrochloric acid, sulfuric acid, nitric acid, hydrobromic acid, or the like. The amount of the acid to be used is preferably a large excess amount, e.g., about 5–50 molar equivalents for compound (I-6). This reaction is carried out usually at 30° C. to 150° C., preferably about 50° C. to 120° C. and the reaction time is usually 1–100 hours. Furthermore, the sulfonylamino derivative of compound (I-7) is produced according to Process F described in JP 10-36374 A, and the acylamino derivative thereof is produced according to its Process I.

The thus-obtained thienopyridine derivative can be isolated and purified by a known separation and purification means such as concentration, concentration under reduced pressure, solvent extraction, crystallization, recrystallization, trans-solubilization, chromatography, and the like.

Compound (I-7) obtained by Process E is also produced by the Gabriel method, wherein compound A, obtained by the reaction of compound (II-1) with an alkali metal salt of phthalimide such as the potassium salt of phthalimide, is decomposed by the reaction thereof with an acid or hydrazine (Process F).

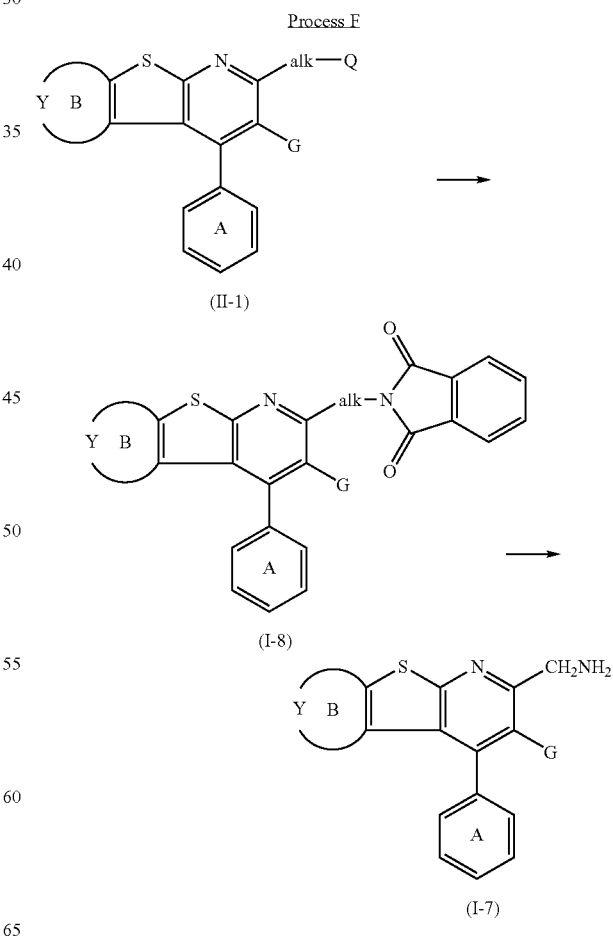

wherein each symbol is as defined above.

The reaction of compound (II-1) with an alkali metal salt of phthalimide such as the potassium salt of phthalimide is carried out in the same manner as that of Process A. Compound (I-7) is produced by subjecting to decomposition reaction in the presence of an acid or hydrazine. The decomposition reaction of compound (I-8) is carried out in the presence of water. As for said solvent, there can be used the same solvent as that used in the hydrolysis of compound (I-6) in Process E. As for said acid, there can be used hydrochloric acid, sulfuric acid, nitric acid, hydrobromic acid, or the like.

The thus-obtained thienopyridine derivative (I-7) and (I-8) can be isolated and purified by a known separation and purification means such as concentration, concentration under reduced pressure, solvent extraction, crystallization, recrystallization, trans-solubilization, chromatography, and the like.

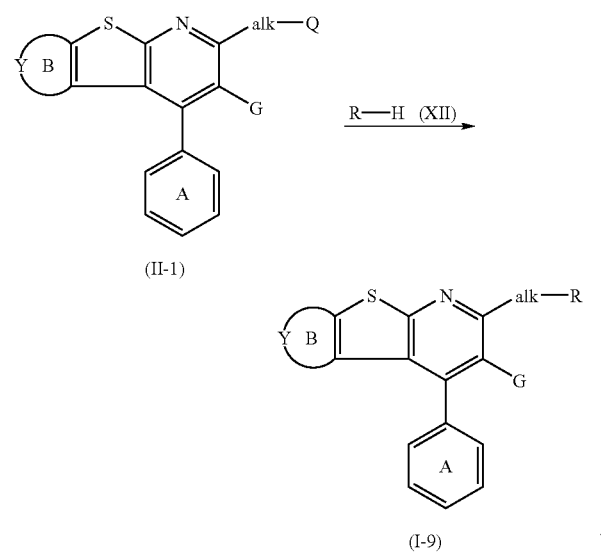

wherein each symbol is as defined above.

In this method, (II-1) is reacted with (XII) in the presence of a base to produce (I-9). The reaction of (II-1) with (XII) is carried out in an appropriate solvent. Examples of said solvent include aromatic hydrocarbon such as benzene, toluene, xylene, and the like; ether such as dioxane, tetrahydrofuran, dimethoxyethane, and the like; alcohol such as methanol, ethanol, propanol, and the like; ethyl acetate; acetonitrile; pyridine; N,N-dimethylformamide (DMF); dimethyl sulfoxide (DMSO); chloroform; dichloromethane; 1,2-dichloroethane; 1,1,2,2,-tetrachloroethane; acetone; 2-butanone; and a mixture thereof. The reaction of (II-1) with (XII) is carried out in the presence of an appropriate base such as an alkali metal salt, for example, sodium hydroxide, potassium hydroxide, potassium carbonate, sodium carbonate, sodium hydrogen carbonate, or the like; an amine such as pyridine, triethylamine, N,N-dimethylaniline, or the like; sodium hydride; potassium hydride; n-butyllithium; t-butyllithium; lithium diisopropylamide (LDA); or the like. The amount of the base to be used is preferably about 1–5 molar equivalents for compound (II-1). This reaction is carried out usually at −70° C. to 150° C., preferably −70° C. to 100° C. This reaction is also carried out by the use of an excess amount of (XII) as the base.

The thus-obtained thienopyridine derivative (I-9) can be isolated and purified by a known separation and purification means such as concentration, concentration under reduced pressure, solvent extraction, crystallization, recrystallization, trans-solubilization, chromatography, and the like.

Further, the compound represented by the general formula (II-1), which is the starting material in the above-mentioned Process A, Process E, Process F, and Process G, can be produced, for example, in the following manner.

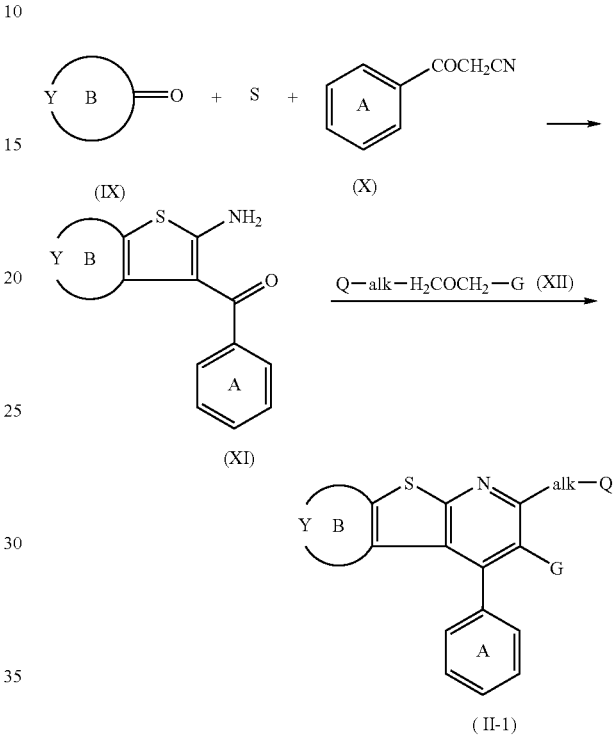

wherein each symbol is as defined above.

According to a process described in Journal of Medicinal Chemistry, 17, 624 (1974), compound (XI) is produced by reaction of compound (IX), sulfur, and compound (X) in the presence of a base in a solvent. Examples of said solvent include aromatic hydrocarbon such as benzene, toluene, xylene, and the like; ether such as dioxane, tetrahydrofuran, dimethoxyethane, and the like; alcohol such as methanol, ethanol, propanol, and the like; chloroform; dichloromethane; 1,2-dichloroethane; 1,1,2,2,-tetrachloroethane; N,N-dimethylformamide (DMF); dimethylacetamide (DMA); dimethyl sulfoxide (DMSO); 1-methyl-2-pyrrolidone; 1,3-dimethyl-2-imidazolidinone; and a mixture thereof. The reaction is carried out in the presence of an appropriate base such as an alkali metal salt such as sodium hydroxide, potassium hydroxide, potassium carbonate, sodium carbonate, sodium bicarbonate, etc.; a metal alkoxide such as sodium methoxide, sodium ethoxide, sodium tert-butoxide, potassium tert-butoxide, etc.; an amine such as triethylamine, diethylamine, morpholino, piperidine, N,N-dimethylaniline, or the like. The amount of this base is preferably about 1–5 molar equivalents for compound (IX). This reaction is carried out usually at −20° C. to 150° C., preferably −10° C. to 100° C. Then, compound (II-1) is produced by the reaction of compound (XI) and compound (XII). The reaction of (XI) and (XII) is carried out in a solvent in the presence of an appropriate acid such as a Lewis acid, for example, aluminum chloride, zinc chloride, or the like; hydrochloric acid; sulfuric acid; trifluoroacetic acid; p-toluenesulfonic acid; or the like. Examples of said solvent include aromatic hydrocarbon such as benzene, toluene, xylene, and the like; ether such as dioxane, tetrahydrofuran, dimethoxyethane, and the like; alcohol such as methanol, ethanol, propanol, and the like; ethyl acetate; N,N-dimethylformamide (DMF); dimethyl sulfoxide (DMSO); chloroform; dichloromethane; 1,2-dichloroethane; 1,1,2,2,-tetrachloroethane; and a mixture thereof. The amount of compound (VIII) to be used is preferably about 1.0–2.0 molar equivalents for compound (VII). The amount of the acid is preferably about 0.05–2.0 molar equivalents for compound (VII). This reaction is carried out usually at 0° C. to 200° C., preferably about 20° C. to 120° C. The reaction time is 0.5–20 hours, preferably 1–10 hours.

The thus-obtained compound represented by the general formula (II-1) can be isolated and purified by a known separation and purification means such as concentration, concentration under reduced pressure, solvent extraction, crystallization, recrystallization, trans-solubilization, chromatography, and the like.

In the case where the thienopyridine derivatives produced by Process A to Process G have isopropoxy group as a substituent on ring A, the isopropoxy group can be converted into hydroxyl group by treatment with titanium tetrachloride. This reaction is carried out in a solvent such as chloroform, dichloromethane, carbon tetrachloride, or the like at −50° C. to 30° C., preferably about −10° C. to 20° C.

Since compound (I) or a salt thereof of the present invention has anti-inflammatory activity and further anti-arthritic activity, it can be used in the prevention or treatment of all arthritic diseases with inflammatory conditions in joints. The arthritic diseases include, for example, chronic rheumatoid arthritis and the like.

Also, compound (I) of the present invention or a salt thereof can be used in the prevention and treatment of rheumatism and the like.

Further, compound (I) of the present invention or a salt thereof has excellent suppressing effect on bone resorption and is useful in the prevention and treatment of bone destruction, osteoporosis, and the like, which accompany arthritis. Furthermore, the compound of the present invention has suppressing effect on immune cytokine production and is also useful in the prevention and treatment of diseases associated with immune reactions, and/or in the prevention and treatment of rejection reaction after organ transplantation.

Furthermore, compound (I) of the present invention or a salt thereof has suppressing effect on the production of immune cytokines [e.g., interleukin-2 (IL-2), interferon-γ (IFN-γ), etc.] and is useful in the prevention and treatment of diseases associated with immune including autoimmune diseases.

Examples of these diseases include systemic lupus erythematosus, inflammatory bowel disease (ulcerative colitis, Crohn's disease), multiple sclerosis, psoriasis, chronic hepatitis, urinary bladder carcinoma, breast carcinoma, uterine cervix carcinoma, chronic lymphocytic leukemia, chronic myelocytic leukemia, colorectal cancer, colon cancer, rectal cancer, infection with Helicobacter pylori, Hodgkin's disease, insulin-dependent diabetes mellitus, malignant melanoma, multiple myeloma, non Hodgkin's lymphoma, non-small cell lung carcinoma, ovarian cancer, peptic ulcer, prostatic carcinoma, septic shock, tuberculosis, sterility, arteriosclerosis, Behcet's disease, asthma, atopic dermatitis, nephritis, systemic mycosis, acute bacterial meningitis, acute myocardial infarction, acute pancreatitis, acute viral encephalitis, adult respiratory distress syndrome, bacterial pneumonia, chronic pancreatitis, herpes simplex virus infection, varicella-zoster virus infection, AIDS, human papilloma virus infection, influenza, invasive staphylococcal infection, peripheral vascular diseases, sepsis, interstitial hepatic diseases, regional ileitis, and the like. Compound (I) of the present invention or a salt thereof is used, among others, in prevention or treatment of lupus erythematosus, chronic hepatitis, interstitial hepatic diseases, asthma, psoriasis, ulcerative colitis, Crohn's disease, regional ileitis, multiple sclerosis, or the like.

Also, compound (I) of the present invention or a salt thereof is useful in the prevention and treatment of rejection reaction after organ transplantation.

Moreover, compound (1) of the present invention or a salt thereof is useful as a T-cell differentiation modifying drug. A T-cell differentiation modifying drug is a generic name of a compound which modifies differentiation of T lymphocyte into Type-1 T lymphocyte (T1 cell) or Type-II T lymphocyte (T2 cell). T1 cells are T lymphocytes mainly producing IFN-γ, IL-2 and TNFβ as cytokines, and include $CD4^-$ T lymphocytes and $CD8^-$ T lymphocytes. T2 cells are T lymphocytes mainly producing IL-4, IL-5 and IL-10 as cytokines and include $CD4^-$ T lymphocytes and $CD8^+$ T lymphocytes. Therefore, a T-cell differentiation modifying drug can be used for preventing or treating arthritis and the above-mentioned other diseases.

The toxicity of the compound of the present invention is low.

Therefore, compound (I) of the present invention or a salt thereof may be used as prophylactic and therapeutic drugs of inflammatory diseases, arthritis, rheumatism, rheumatoid arthritis, or autoimmune diseases; as prophylactic and therapeutic drugs of rejection reaction after organ transplantation; and as prophylactic and therapeutic drugs of bone destruction, osteoporosis, and the like, which accompany arthritis, in mammalian animals including human being (e.g., human being, horse, cow, pig, dog, cat, rat, mouse, etc.).

The dosage of compound (I) and a salt thereof can be selected in various ways depending on the administration route and the symptom of the patient to be treated. Usually, as compound (I) per an adult, the daily dosage can be selected from a range of about 1 mg to about 500 mg, preferably about 5 mg to about 100 mg in the case of oral administration, and from a range of about 0.1 mg to about 100 mg, further preferably about 0.3 mg to about 10 mg in the case of parenteral administration. The dosage can be administered by dividing 1–3 times per day.

The compound (I) or a salt thereof of the present invention can be compounded with a pharmaceutically permissible carrier and can be orally or parenterally administered as solid formulations such as tablets, capsules, granules, powders, or the like; or liquid formulations such as syrups, injections, or the like. Also, there can be prepared formulations for transdermal administration such as patchings, cataplasms, ointments (including creams), plasters, tapes, lotions, solutions, suspensions, emulsions, sprays, and the like.

As for the pharmaceutically acceptable carrier, a variety of organic or inorganic carrier substances, which have been conventionally employed as formulation materials, are used, and are compounded as an excipient, a lubricant, a binding agent, and a disintegrator in solid formulations; a solvent, a solubilizing agent, a suspending agent, an isotonic agent, a buffering agent, and an analgesic in liquid formulations.

Also, as needed, formulation additives such as a preservative, an antioxidant, a stabilizer, a coloring agent, a sweetening agent, and the like can be used.

Preferred examples of the excipient include lactose, sucrose, D-mannitol, starch, crystalline cellulose, light anhydrous silicic acid, and the like. Preferred examples of the lubricant include magnesium stearate, potassium stearate, talc, colloidal silica, and the like. Preferable examples of the binding agent include crystalline cellulose, α-starch, sucrose, D-mannitol, dextrin, hydroxypropyl cellulose, hydroxypropylmethyl cellulose, polyvinyl pyrrolidone, and the like. Preferable examples of the disintegrator include starch, carboxymethyl cellulose, calcium carboxymethyl cellulose, croscarmellose sodium, sodium carboxymethyl starch, low-substituted hydroxypropyl cellulose, and the like. Preferable examples of the solvent include water for injection, alcohol, propylene glycol, macrogol, sesame oil, corn oil, and the like.

As needed, for the purpose of taste masking, enteric coating, or prolonged action, oral formulations can be coated by a per se known method. Examples of this coating agent include hydroxypropylmethyl cellulose, ethyl cellulose, hydroxymethyl cellulose, hydroxypropyl cellulose, polyoxyethylene glycol, Tween 80, Pluronic F68 [polyoxyethylene (160) polyoxypropylene (30) glycol], cellulose acetate phthalate, hydroxypropylmethyl cellulose phthalate, hydroxymethyl cellulose acetate phthalate, Eudragit (manufactured by Rohm Company, methacrylic acid-acrylic acid copolymer), and the like.

Preferred examples of the solubilizing agent include polyethylene glycol, propylene glycol, benzyl benzoate, ethanol, trisamiomethane, cholesterol, triethanolamine, sodium carbonate, sodium citrate, and the like. Preferred examples of the suspending agent include surfactants such as stearyltriethanolamine, sodium lauryl sulfate, laurylaminopropionic acid, lecithin, benzalkonium chloride, benzethonium chloride, glycerin monostearate, etc.; hydrophilic high molecular weight substances such as polyvinyl alcohol, polyvinyl pyrrolidone, sodium carboxymethyl cellulose, methyl cellulose, hydroxymethyl cellulose, hydroxyethyl cellulose hydroxypropyl cellulose, etc.; and the like. Preferred examples of the isotonic agent include sodium chloride, glycerin, D-mannitol, and the like. Preferred examples of the buffering agent include buffer solutions of a phosphate, an acetate, a carbonate, a citrate, or the like. Preferred examples of the analgesic include benzyl alcohol and the like. Preferred examples of the preservative include paraoxybenzoic acid ester, chlorobutanol, benzyl alcohol, phenethyl alcohol, dehydroacetic acid, sorbic acid, and the like. Preferred examples of the antioxidant include sulfite, ascorbic acid, and the like.

Moreover, compound (I) or a salt thereof can be administered as a single formulation, or simultaneously or at temporal intervals together with [1 a cyclooxygenase inhibitor (a Cox-I, Cox-II inhibitor), [2] a disease-modifying anti-rheumatic drug and an immunodepressant, [3] a biological preparation, [4] an analgesic and an anti-inflammatory agent, [5] a therapeutic drug for bone disease, [6] p38MAP kinase inhibitor and/or TNF-α production inhibitor, [7] c-JUN N-terminal kinase (JNK) inhibitor, or the like.

[1] Examples of cyclooxygenase inhibitors (Cox-I, Cox-II inhibitors) include celecoxib, rofecoxib, salicylic acid derivatives such as aspirin, diclofenac, indomethacin, loxoprofen, and the like. The oral doses of these drugs are, for example, about 100–200 mg/day for celecoxib, about 10–30 mg/day for rofecoxib, 1000–4500 mg/day for salicylic acid derivatives such as aspirin, about 25–75 mg/day for diclofenac, about 50–150 mg/day for indomethacin, and about 60–180 mg/day for loxoprofen.

[2] Examples of disease-modifying anti-rheumatic drugs and immunodepressants include methotrexate, leflunomide, prograf, sulfasalazine, D-penicillamine, oral gold compounds, and the like. The oral doses of these drugs are, for example, about 2.5–7.5 mg/week for methotrexate, about 20–100 mg/day for leflunomide, about 1–5 mg/day for Prograf, about 500–2000 mg/day for sulfasalazine, about 100–600 mg/day for D-penicillamine, and about 3–6 mg/day for oral gold compounds.

[3] Examples of biological preparations include monoclonal antibodies (e.g., anti-TNF-α antibody, anti-IL-12 antibody, anti-IL-6 antibody, anti-ICAM-I antibody, anti-CD4 antibody, etc.), soluble receptors (e.g., soluble TNF-α receptor, etc.), and protein ligands (IL-1 receptor antagonist, etc.). The oral doses of these drugs are, for example, about 0.1–50 mg/kg/day, preferably 0.5–20 mg/kg/day.

[4] Examples of analgesics and anti-inflammatory agents include centrally acting analgesics (e.g., morphine, codeine, pentazocine, etc.), steroids (e.g., prednisolone, dexamethasone, betamethazone, etc.), and anti-inflammatory enzyme agents (e.g., bromelain, lysozyme, proctase, etc.). The oral doses of these drugs are, for example, about 1–1000 mg/day, preferably about 5–300 mg/day, for centrally acting analgesics, about 0.1–400 mg/day, preferably about 5–100 mg/day, for steroids, and about 1–100 mg/day, preferably about 5–40 mg/day, for anti-inflammatory enzyme agents.

[5] Examples of therapeutic drugs for bone diseases (e.g., bone fracture, refracture, osteoporosis, osteomalacia, Paget's disease of bone, ankylosing spondylitis, chronic rheumatoid arthritis, denerative gonarthritis, destruction of joint tissues in related diseases, etc.) include calcium preparations (e.g., calcium carbonate, etc.), calcitonin preparations, vitamin D preparations (e.g., α-calcidol, etc.), sex hormones (e.g., estrogen, estradiol, etc.), prostaglandin $A_1$, bisphosphonates, ipriflavons, fluorine compounds (e.g., sodium fluoride, etc.), vitamin $K_2$, bone morphogenic protein (BMP), fibroblast growth factor (FGF), platelet-derived growth factor (PDGF), transforming growth factor (TGF)-β, insulin-like growth factor-1 and -2 (IGF-1, -2), parathyroid hormone (PTH), and compounds described in European Patent Publications No. EP 376197 A1, EP 460488 A1, and EP 719782 A1 (e.g., (2R,4S)-(−)-N-[4-(diethoxyphosphorylmethyl)phenyl]-1,2,4,5-tetrahydro-4-methyl-7,8-methylenedioxy-5-oxo-3-benzothiepin-2-carboxamide, etc.).

[6] Examples of p38MAP kinase inhibitor and/or TNF-α inhibitor include:

i) a compound represented by the formula:

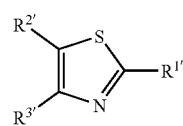

wherein $R^{1'}$ is hydrogen atom, an optionally substituted hydrocarbon group, an optionally substituted heterocyclic group, or an optionally substituted amino group or an acyl group; $R^{2'}$ is an optionally substituted pyridyl group; and $R^{3'}$ is an optionally substituted aromatic group, a salt thereof or a prodrug thereof;

ii) a compound represented by the formula:

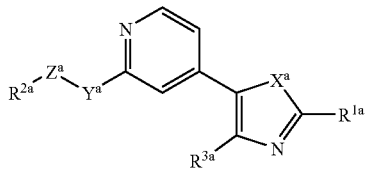

wherein $R^{1a}$ is hydrogen atom, an optionally substituted hydrocarbon group, an optionally substituted heterocyclic group, an optionally substituted amino group or an acyl group; $R^{2a}$ is an optionally substituted aromatic group; $R^{3a}$ is hydrogen atom, an optionally substituted pyridyl group or an optionally substituted aromatic hydrocarbon group; $X^a$ is oxygen atom or an optionally oxidized sulfur atom; $Y^a$ is a bond, oxygen atom, an optionally oxidized sulfur or $NR^{4a}$ (wherein $R^{4a}$ is hydrogen atom, an optionally substituted hydrocarbon group or an acyl); and $Z^a$ is a bond or an optionally substituted divalent straight chain hydrocarbon group, a salt thereof or a prodrug thereof; for example, N-[5-(2-benzoylamino-4-pyridyl)-4-(3,5-dimethylphenyl)-1,3-thiazol-2-yl]acetamide;
N-[5-(2-benzylamino-4-pyridyl)-4-(3,5-dimethylphenyl)-1,3-thiazol-2-yl]acetamide;
N-[4-[4-(4-methoxypheny)-2-methyl-1,3-thiazol-5-yl]-2-pyridyl]benzamide;
N-[4-[2-(4-fluoropheny)-4-(3-methylphenyl)-1,3-thiazol-5-yl]-2-pyridyl]phenylacetamide;
N-[4-[2-ethyl-4-(3-methylpheny)-1,3-thiazol-5-yl]-2-pyridyl]phenylacetamide;
N-[4-[4-(3-methylpheny)-2-propyl-1,3-thiazol-5-yl]-2-pyridyl]phenylacetamide;
N-[4-[2-butyl-4-(3-methylpheny)-1,3-thiazol-5-yl]-2-pyridyl]phenylacetamide;
N-[4-[4-(3-methylpheny)-2-(4-methylthiophenyl)-1,3-thiazol-5-yl]-2-pyridyl]phenylacetamide;
N-[4-[2-ethyl-4-(3-methylphenyl)-1,3-thiazol-5-yl]-2-pyridyl]benzamide;
N-[4-[2-ethyl-4-(3-methylphenyl)-1,3-thiazol-5-yl]-2-pyridyl]-3-phenylpropionamide;
N-[4-[2-ethyl-4-(3-methylphenyl)-1,3-thiazol-5-yl]-2-pyridyl]-3-(4-methoxyphenyl)propionamide;
N-[4-[2-ethyl-4-(3-methylphenyl)-1,3-thiazol-5-yl]-2-pyridyl]-3-phenylbutylamide;
N-[4-[4-(3-methylphenyl)-2-propyl-1,3-thiazol-5-yl]-2-pyridyl]benzaminde;
N-[4-[4-(3-methylphenyl)-2-propyl-1,3-thiazol-5-yl]-2-pyridyl]-3-phenylpropionaminde;
N-[4-[2-butyl-4-(3-methylphenyl)-1,3-thiazol-5-yl]-2-pyridyl]benzaminde;
N-[4-[2-butyl-4-(3-methylphenyl)-1,3-thiazol-5-yl]-2-pyridyl]-3-phenylpropionaminde;
N-[4-[2-(4-fluorophenyl)-4-(3-methylphenyl)-1,3-thiazol-5-yl]-2-pyridyl]benzaminde;
N-[4-[2-(4-fluorophenyl)-4-(3-methylphenyl)-1,3-thiazol-5-yl]-2-pyridyl]-3-phenylpropionaminde;
N-[4-[4-(3-methylphenyl)-2-(4-methylthiophenyl)-1,3-thiazol-5-yl]-2-pyridyl]benzaminde;
N-[4-[4-(3-methylphenyl)-2-(4-methylthiophenyl)-1,3-thiazol-5-yl]-2-pyridyl]-3-phenylpropionaminde;
N-benzyl-N-[4-[2-ethyl-4-(3-methylphenyl)-1,3-thiazol-5-yl]-2-pyridyl]amine;
N-[4-[2-ethyl-4-(3-methylphenyl)-1,3-thiazol-5-yl]-2-pyridyl]-N-(2-phenylethyl)amine;
N-[4-[2-ethyl-4-(3-methylphenyl)-1,3-thiazol-5-yl]-2-pyridyl]-N-(3-phenylpropyl)amine;
N-benzyl-N-[4-[4-(3-methylphenyl)-2-propyl-1,3-thiazol-5-yl]-2-pyridyl]amine;
N-[4-[4-(3-methylphenyl)-2-propyl-1,3-thiazol-5-yl]-2-pyridyl]-N-(2-phenylethyl)amine;
N-[4-[4-(3-methylphenyl)-2-propyl-1,3-thiazol-5-yl]-2-pyridyl]-N-(3-phenylpropyl)amine;
N-benzyl-N-[4-[2-butyl-4-(3-methylphenyl)-1,3-thiazol-5-yl]-2-pyridyl]amine;
N-[4-[2-butyl-4-(3-methylphenyl)-1,3-thiazol-5-yl]-2-pyridyl]-N-(2-phenylethyl)amine;
N-[4-[2-butyl-4-(3-methylphenyl)-1,3-thiazol-5-yl]-2-pyridyl]-N-(3-phenylpropyl)amine;
N-benzyl-N-[4-[4-(3-methylphenyl)-2-(4-methylthiophenyl)-1,3-thiazol-5-yl]-2-pyridyl]amine;
N-[4-[4-(3-methylphenyl)-2-(4-methylthiophenyl)-1,3-thiazol-5-yl]-2-pyridyl]-N-(2-phenylethyl)amine;
N-[4-[4-(3-methylphenyl)-2-(4-methylthiophenyl)-1,3-thiazol-5-yl]-2-pyridyl]-N-(3-phenylpropyl)amine;
N-[4-[4-(3-methylphenyl)-2-(4-methylsulfonyl-phenyl)-1,3-thiazol-5-yl]-2-pyridyl]benzamide;
N-[4-[4-(3-methylphenyl)-2-(4-methylsulfonyl-phenyl)-1,3-thiazol-5-yl]-2-pyridyl]phenylacetamide;
N-[4-[4-(3-methylphenyl)-2-(4-methylsulfonyl-phenyl)-1,3-thiazol-5-yl]-2-pyridyl]-3-phenylpropionamide;
N-benzyl-N-[4-[4-(3-methylphenyl)-2-(4-methylsulfonylphenyl)-1,3-thiazol-5-yl]-2-pyridyl]amine;
N-[4-[4-(3-methylphenyl)-2-(4-methylsulfonyl-phenyl)-1,3-thiazol-5-yl]-2-pyridyl]-N-(3-phenylpropyl)-amine;
N-[4-[4-(3-methylphenyl)-2-(4-methylsulfonyl-phenyl)-1,3-thiazol-5-yl]-2-pyridyl]-N-(2-phenylethyl)-amine;
N-(4-fluorobenzyl)-N-[4-[4-(3-methylphenyl)-2-(4-methylsulfonylphenyl)-1,3-thiazol-5-yl]-2-pyridyl]amine;
(S)-N-[4-(3-methylphenyl)-5-(2-(1-phenylethyl-amino)-4-pyridyl)-1,3-thiazol-2-yl]nicotinamide;
(R)-N-[4-(3-methylphenyl)-5-(2-(1-phenylethyl-amino)-4-pyridyl)-1,3-thiazol-2-yl]nicotinamide;
(S)-N-[4-(3-methylphenyl)-5-(2-(1-phenylethyl-amino)-4-pyridyl)-1,3-thiazol-2-yl]-2-methylnicotinamide;
(R)-N-[4-(3-methylphenyl)-5-(2-(1-phenylethyl-amino)-4-pyridyl)-1,3-thiazol-2-yl]-2-methylnicotinamide;
(S)-N-[4-(3-methylphenyl)-5-(2-(1-phenylethyl-amino)-4-pyridyl)-1,3-thiazol-2-yl]-2-chloronicotinamide;
(R)-N-[4-(3-methylphenyl)-5-(2-(1-phenylethyl-amino)-4-pyridyl)-1,3-thiazol-2-yl]-2-chloronicotinamide;
(S)-N-[4-(3-methylphenyl)-5-(2-(1-phenylethyl-amino)-4-pyridyl)-1,3-thiazol-2-yl]-2-methoxynicotinamide;
(R)-N-[4-(3-methylphenyl)-5-(2-(1-phenylethyl-amino)-4-pyridyl)-1,3-thiazol-2-yl]-2-methoxynicotinamide;
N-[5-(2-benzylamino-4-pyridyl)-4-(3-methylphenyl)-1,3-thiazol-2-yl]nicotinamide;
N-[5-(2-benzylamino-4-pyridyl)-4-(3-methylphenyl)-1,3-thiazol-2-yl]-2-methoxynicotinamide;
N-[5-(2-benzylamino-4-pyridyl)-4-(3-methylphenyl)-1,3-thiazol-2-yl]-2-chloronicotinamide;
N-[5-(2-benzylamino-4-pyridyl)-4-(3-methylphenyl)-1,3-thiazol-2-yl]-2-methylnicotinamide;
N-[5-(2-benzoylamino-4-pyridyl)-4-(3-methylphenyl)-1,3-thiazol-2-yl]nicotinamide;
N-[5-(2-benzoylamino-4-pyridyl)-4-(3-methylphenyl)-1,3-thiazol-2-yl]-2-methylnicotinamide;
N-[5-(2-benzoylamino-4-pyridyl)-4-(3-methylphenyl)-1,3-thiazol-2-yl]-2-chloronicotinamide;

N-[5-(2-benzoylamino-4-pyridyl)-4-(3-methylphenyl)-1,3-thiazol-2-yl]-2-methoxynicotinamide;

(S)-N-(1-phenylethyl)-4-[2-ethyl-4-(3-methylphenyl)-1,3-thiazol-5-yl]-2-pyridylamine;

(R)-N-(1-phenylethyl)-4-[2-ethyl-4-(3-methylphenyl)-1,3-thiazol-5-yl]-2-pyridylamine;

(S)-N-(1-phenylethyl)-4-[4-(3-methylphenyl)-2-propyl-1,3-thiazol-5-yl]-2-pyridylamine;

(R)-N-(1-phenylethyl)-4-[4-(3-methylphenyl)-2-propyl-1,3-thiazol-5-yl]-2-pyridylamine;

(S)-N-(1-phenylethyl)-4-[2-butyl-4-(3-methylphenyl)-1,3-thiazol-5-yl]-2-pyridylamine;

(R)-N-(1-phenylethyl)-4-[2-butyl-4-(3-methylphenyl)-1,3-thiazol-5-yl]-2-pyridylamine;

(S)-N-(1-phenylethyl)-4-[4-(3-methylphenyl)-2-(4-methylthiophenyl)-1,3-thiazol-5-yl]-2-pyridylamine;

(R)-N-(1-phenylethyl)-4-[4-(3-methylphenyl)-2-(4-methylthiophenyl)-1,3-thiazol-5-yl]-2-pyridylamine;

(S)-N-(1-phenylethyl)-4-[4-(3-methylphenyl)-2-(4-methylsulfophenyl)-1,3-thiazol-5-yl]-2-pyridylamine;

(R)-N-(1-phenylethyl)-4-[4-(3-methylphenyl)-2-(4-methylsulfophenyl)-1,3-thiazol-5-yl]-2-pyridylamine;

(S)-N-(1-phenylethyl)-4-[2-(4-fluorophenyl)-4-(3-methylphenyl)-1,3-thiazol-5-yl]-2-pyridylamine;

(R)-N-(1-phenylethyl)-4-[2-(4-fluorophenyl)-4-(3-methylphenyl)-1,3-thiazol-5-yl]-2-pyridylamine;

or a salt thereof;

iii) a compound represented by the formula:

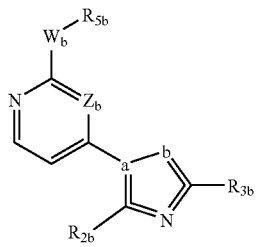

wherein a is N or C; b is CH when a is N, or O when a is C; = is a bond or a double bond depending upon whether the azole ring being imidazole ring or oxazole ring; $Z_b$ is N or CH; $W_b$ is —$NR_{6b}$—$Y_b$— ($R_{6b}$ is H, $C_{1-4}$ alkyl, $C_{3-8}$ cycloalkyl, $C_{3-8}$ cycloalkyl-$C_{1-3}$ alkyl, $C_{6-18}$ aryl, $C_{3-18}$ heteroalkyl, $C_{7-19}$ aralkyl or $C_{4-19}$ heteroaralkyl; —$Y_b$— is $C_{1-4}$ alkylene or a bond), —O— or —S—; $R_{2b}$ is phenyl (optionally substituted with 1 or more substitutes selected from the group consisting of a halogen atom, trifluoromethyl, cyano, amide, thioamide, carboxylate, thiocarboxylate, $C_{1-4}$ alkoxy, amino, and mono- or di-$C_{1-4}$ alkylamino); $R_{3b}$ is H, a halogen atom, $C_{1-10}$ alkyl, $C_{1-4}$ alkenyl, $C_{3-10}$ cycloalkyl, $C_{3-18}$ heterocycloalkly, $C_{6-18}$ aryl, $C_{3-18}$ heteroaryl, or —CH=N—NH—C(NH)NH$_2$ (each of which may be substituted with 1 to 4 substituents selected from the group consisting of $C_{1-4}$ alkyl optionally substituted with hydroxyl, a halogen atom, $C_{1-4}$ alkyl substituted with halogen, hydroxyl, $C_{1-4}$ alkoxy, $C_{1-4}$ alklthio, carboxy, carbonyl optionally substituted with $C_{1-6}$ alkyl or $C_{1-6}$ alkoxy, amino, mono- or di-$C_{1-4}$ alkylamino, and 5- to 7-membered N-containing heterocyclic group (which may contain additional one or more hetero atoms)); and $R_{5b}$ is $C_{6-18}$ aryl, $C_{3-18}$ heteroaryl or $C_{3-12}$ cycloalkyl (each of which may be substituted 1 to 4 substituents selected from the group consisting of $C_{1-4}$ alkyl, $C_{1-4}$ alkyl substituted with halogen, hydroxyl, $C_{1-4}$ alkyl, $C_{1-4}$ alkylthio, amino, mono- or di-$C_{1-4}$ alkylamino and a 5- to 7-membered N-containing heterocyclic group (which may contain additional one or more hetero atoms)), a salt thereof or a prodrug thereof; and the like.

[7] As the JNK inhibitor, there are, for example, the compounds described in WO 00/35906, WO 00/35909, WO 00/35921, WO 00/64872 and WO 00/75118, and the like.

The present invention is further illustrated in more detail by the following Reference Examples, Examples, and Test Example, but they are not to be construed to restrict the present invention.

In the following description, Me represents methyl, Et represents ethyl, Ph represents phenyl, and Cbz represents benzyloxycarbonyl, respectively.

TEST EXAMPLE 1

Effect on Adjuvant Arthritis in Rats

The test compound was suspended in 0.5% methyl cellulose and administered orally once daily for 14 days to male Lewis rats (7-week old, Japan Clea), which had been sensitized by the intradermal injection of 0.05 ml Freund's complete adjuvant (0.5% suspension of killed *Mycobacterium tuberculosis* in liquid paraffin) into the right hind footpad. Immediately before the sensitization (Day 0) and on 14 days after the administration (Day 14), the volume of the edema on the left footpad was measured by using a plethysmometer (manufactured by Ugo Basile Company, Italy) and the suppression rate (%) of footpad swelling relative to the unsensitized rats was calculated according to the following equation.

Suppression rate of footpad swelling (%)={1−[(volume of footpad edema in the treatment group)−(volume of footpad edema in the unsensitized group)]/[(volume of footpad edema in the non-treatment group)−(volume of footpad edema in the unsensitized group)]}×100

The results were expressed by the mean±S.E. in each group (n=6) and tested by Dunnet's comparison with a significance level of 5%. As shown in Table 1, the compounds of the present invention exhibited efficacy in suppressing the footpad swelling.

TABLE 1

| Compound (Example No.) | Dose (mg/kg/day) | Suppression rate of footpad swelling (%) |
| --- | --- | --- |
| 13 | 3.13 | 77** |
| 22 | 3.13 | 88** |

**:p < 0.01 vs. control

REFERENCE EXAMPLE 1

A mixture of 4-oxothiane (2.0 g), 4-methoxybenzoylactonitrile (described in PCT International Application Publication No. WO99/65916) (3.0 g), sulfur (577 mg), morpholine (1.6 g) and ethanol (120 ml) was heated under reflux with stirring for 3 hours and then the solvent was evaporated under reduced pressure. To the residue was added ethyl acetate and the resulting solution was washed with 1 N hydrochloric acid and water, dried (MgSO$_4$), and then evaporated under reduced pressure to remove the solvent. The residue was subjected to column chromatography on silica gel, and 2-amino-4,5-dihydro-3-(4-methoxybenzoyl)-7H-thieno[2,3-c]thiopyran (3.6 g, 69%) was obtained from the eluates with ethyl acetate-hexane (3:1). It was recrystallized from THF-hexane. Colorless prisms. Melting point of 178–179° C.

According to the same manner, compounds in Reference Examples 2 to 9 described in Table 2 were synthesized.

TABLE 2

| Reference Example No. | Y | R | Melting point (° C.) | Recrystallization solvent |
|---|---|---|---|---|
| 1 | S | 4-MeO | 178–179 | THF-hexane |
| 2 | O | 4-PhCH₂O | 133–134 | THF-hexane |
| 3 | H₂C=C | 4-MeO | 153–154 | Ethyl acetate-hexane |
| 4[a)] | Me₂C=C | 4-MeO | Oil | |
| 5 | (dioxolane) | 4-MeO | 161–162 | THF-hexane |
| 6 | Me₂C | 4-MeO | 154–155 | THF-hexane |
| 7[b)] | PhCH₂O—CH | 4-MeO | Oil | |
| 8 | EtO₂C—CH | 4-MeO | 102–103 | Ethyl acetate-hexane |
| 9[c)] | PhCH₂O₂C—CH | 4-MeO | Oil | |

[a)] $^1$H NMR (CDCl$_3$) δ: 1.68 (3H, s), 1.69 (3H, s), 1.97 (2H, t, J = 6.0 Hz), 3.20 (2H, t, J = 6.0 Hz), 3.30 (2H, s), 3.86 (3H, s), 6.40 (2H, br s), 6.90 (2H, d, J = 8.8 Hz), 7.51 (2H, d, J = 8.8 Hz);
[b)] $^1$H NMR (CDCl$_3$) δ: 1.60–2.30 (4H, m), 2.56–2.70 (1H, m), 2.82–3.00 (1H, m), 3.80–3.90 (4H, m), 4.58 (2H, s), 6.29 (2H, s), 6.78–6.92 (2H, m), 7.30–7.36 (5H, m), 7.48–7.53 (2H, m);
[c)] $^1$H NMR (CDCl$_3$) δ: 1.55–1.74 (1H, m), 1.88–2.12 (3H, m), 2.70–2.89 (3H, m), 3.85 (3H, s), 5.14 (2H, s), 6.30 (2H, br s), 6.89 (2H, d, J = 8.8 Hz), 7.34 (5H, s), 7.48 (2H, d, J = 8.8 Hz).

REFERENCE EXAMPLE 10

According to the process described in Tetrahedron, 47, 1991, 3259, a solution of sodium amide (18.5 g) in THF (100 ml) was added to a solution of 1,4-cyclohexanedione monoethylene ketal (18.5 g) in THF (100 ml) under a nitrogen atmosphere while keeping the temperature of the solution at 10–20° C. After stirring at 20° C. for 30 minutes, methyl iodide (41.3 g) was added and the stirring was continued at room temperature for 1 hour. The reaction solution was mixed with a saturated aqueous solution of ammonium chloride (100 ml) and extracted with diethyl ether. The diethyl ether layer was washed with water, dried (MgSO$_4$), and then evaporated under reduced pressure to remove the solvent. The residue was subjected to column chromatography on silica gel and an oily mixture (mixture ratio of 1:1, 15.1 g) of 4,4-ethylenedioxy-2-methyl-1-cyclohexanone and 4,4-ethylenedioxy-2,2-dimethyl-1-cyclohexanone was obtained from the eluates with ethyl acetate-hexane (4:1). To a solution of this mixture (2.0 g) in ethanol (20 ml) was added sodium borohydride (440 mg) under ice cooling. After stirring at room temperature for 2 hours, acetic acid (0.2 ml) was added, and the mixture was evaporated under reduced pressure to remove the solvent. To the residue was added ethyl acetate and the resulting solution was washed with water, dried (MgSO$_4$), and then evaporated under reduced pressure to remove the solvent. The residue was subjected to column chromatography on silica gel to obtain 4-hydoxy-3-methyl-1-cyclohexanone ethylene ketal (140 mg, $^1$H NMR (CDCl$_3$) δ: 1.02 (3H, d, J=6.6 Hz), 1.20–2.00 (8H, m), 3.15–3.30 (1H, m), 3.94 (4H, br s)) and 4-hydoxy-3,3-dimethyl-1-cyclohexanone ethylene ketal (470 mg, $^1$H NMR (CDCl$_3$) δ: 1.00 (3H, s), 1.01 (3H, s), 1.35–1.90 (7H, m), 3.38–3.46 (1H, m), 3.90–4.00 (4H, m)) from the eluates with ethyl acetate-hexane (6:1) as oily substances, respectively.

REFERENCE EXAMPLE 11

To a solution of the compound obtained in Reference Example 10, 4-hydoxy-3,3-dimethyl-1-cyclohexanone ethylene ketal, (372 mg) in THF-DMF (5:1; 8 ml) was added sodium hydride (60% in oil, 160 mg) under ice cooling. After stirring at the same temperature for 10 minutes, benzyl bromide (518 mg) and tetrabutylammonium iodide (369 mg) were added and the stirring was continued at room temperature for 11 hour. The reaction mixture was poured into water and extracted with ethyl acetate. The ethyl acetate layer was washed with water, dried (MgSO$_4$), and then evaporated under reduced pressure to remove the solvent. The residue was subjected to column chromatography on silica gel to obtain 4-benzyloxy-3,3-dimethyl-1-cyclohexanone ethylene ketal (360 mg, 65%) as an oily substance from the eluates with hexane-diethyl ether (4:1). $^1$H NMR (CDCl$_3$) δ: 1.01 (3H, s), 1.03 (3H, s), 1.20–1.90 (6H, m), 3.07–3.12 (1H, m), 3.90–3.93 (4H, m), 4.42 (1H, d, J=12.2 Hz), 4.64 (1H, d, J=12.2 Hz), 7.25–7.40 (5H, m).

REFERENCE EXAMPLE 12

To a solution of the compound obtained in Reference Example 11 (360 mg) in THF (5 ml) was added 1 N aqueous hydrochloric acid (2.5 ml) at room temperature and the resulting solution was stirred at 50° C. for 2 hours. The reaction mixture was poured into water and extracted with ethyl acetate. The ethyl acetate layer was washed with water, dried (MgSO$_4$), and then evaporated under reduced pressure to remove the solvent. The residue was subjected to column chromatography on silica gel to obtain 4-benzyloxy-3,3-dimethyl-1-cyclohexanone (250 mg, 82%) as an oily substance from the eluates with hexane-diethyl ether (4:1). $^1$H NMR (CDCl$_3$) δ: 0.95 (3H, s), 1.06 (3H, s), 2.00–2.30 (4H, m), 2.45–2.60 (2H, m), 3.32–3.37 (1H, m), 4.52 (1H, d, J=11.6 Hz), 4.71 (1H, d, J=11.6 Hz), 7.26–7.40 (5H, m).

REFERENCE EXAMPLE 13

A mixture of the compound obtained in Reference Example 12 (258 mg), 4-methoxybenzoylacetonitrile (195 mg), sulfur (40 mg), morpholine (106 mg), and ethanol (5 ml) was heated under reflux with stirring for 6 hours, then poured into water, and extracted with ethyl acetate. The ethyl acetate layer was washed with a saturated aqueous solution of ammonium chloride and water, dried (MgSO$_4$), and then evaporated under reduced pressure to remove the solvent. The residue was subjected to column chromatography on silica gel to obtain 6-benzyloxy-2-amino-3-(4-methoxybenzoyl)-5,5-dimethyl-4,5,6,7-tetrahydro-benzo[b]thiophene (170 mg, 36%) as an oily substance from the eluates with ethyl acetate-hexane (4:1). $^1$H NMR (CDCl$_3$) δ: 0.83–0.84 (6H, m), 1.74 (1H, d, J=16.4 Hz), 1.96 (1H, d, J=16.4 Hz), 2.58 (1H, dd, J=16.4, 6.6 Hz), 2.83 (1H, dd, J=16.4, 5.2 Hz), 3.38 (1H, dd, J=6.6, 5.2 Hz), 3.87 (3H, s), 4.49 (1H, d, J=12.0 Hz), 4.67 (1H, d, J=12.0 Hz), 6.16 (2H, br s), 6.87–6.93 (2H, m), 7.25–7.40 (5H, m), 7.50–7.56 (2H, m).

REFERENCE EXAMPLE 14

Aluminum chloride (85 mg) was added to a mixture of the compound obtained in Reference Example 13 (130 mg), 1,3-dichloroacetone (80 mg), and THF (10 ml) at room temperature and then the resulting mixture was heated under reflux with stirring for 15 minutes. The reaction mixture was poured into water and extracted with ethyl acetate. The ethyl acetate layer was washed with water, dried ($MgSO_4$), and then evaporated under reduced pressure to remove the solvent. The residue was subjected to column chromatography on silica gel to obtain 7-benzyloxy-3-chloro-2-chloromethyl-4,5,6,7-tetrahydro-6,6-dimethyl-(4-methoxyphenyl)[1]benzothieno[2,3-b]pyridine (25 mg, 16%) as an oily substance from the eluates with diethyl ether-hexane (1:8). $^1$H NMR ($CDCl_3$) δ: 0.78 (3H, s), 0.81 (3H, s), 1.59 (1H, d, J=17.0 Hz), 1.83 (1H, d, J=17.0 Hz), 2.92 (1H, dd, J=17.6, 6.0 Hz), 3.09 (1H, dd, J=17.6, 4.8 Hz), 3.37 (1H, dd, J=6.0, 4.8 Hz), 3.90 (3H, s), 4.48 (1H, d, J=12.0 Hz), 4.66 (1H, d, J=12.0 Hz), 4.94 (2H, s), 6.98–7.05 (2H, m), 7.10–7.22 (2H, m), 7.26–7.34 (5H, m).

REFERENCE EXAMPLE 15

Aluminum chloride (1.7 g) was added to a mixed solution of the compound obtained in Reference Example 1 (2.0 g), 1,3-dichloroacetone (1.6 g), and THF (120 ml) at room temperature and then the resulting mixture was heated under reflux with stirring for 3 hours. The reaction mixture was poured into a mixture of toluene (150 ml) and water (75 ml) with stirring and the stirring was continued for 2 hours. The organic layer was separated, dried ($MgSO_4$), and then evaporated under reduced pressure to remove the solvent to obtain 3-chloro-2-chloromethyl-(4-methoxyphenyl)-5,8-dihydro-8H-thiopyrano[4',3':4,5]-thieno[2,3-b]pyridine (2.1 g, 81%). It was recrystallized from ethyl acetate-hexane. Colorless prisms. Melting point of 153–154° C.

According to the same manner, compounds of Reference Examples 16 to 24 described in Table 3 were synthesized.

TABLE 3

| Reference Example No. | Y | R | Melting point (° C.) | Recrystallization solvent |
|---|---|---|---|---|
| 15 | S | 4-MeO | 153–154 | Ethyl acetate-hexane |
| 16 | S | 4-PhCH$_2$O | 136–137 | Ethyl acetate |
| 17 | O | 4-MeO | 186–187 | Ethyl acetate-hexane |
| 18 | H$_2$C=C | 4-MeO | 148–149 | Isopropyl ether |
| 19 | Me$_2$C=C | 4-MeO | 187–188 | THF-hexane |
| 20 | (1,3-dioxolane) | 4-MeO | 219–229 | THF-hexane |
| 21 | Me$_2$C | 4-MeO | 212–213 | Ethyl acetate-hexane |
| 22 | PhCH$_2$O—CH | 4-MeO | 121–122 | Ethylacetate-hexane |
| 23 | EtO$_2$C—CH | 4-MeO | 113–114 | Ethyl acetate-hexane |
| 24 | PhCH$_2$O$_2$C—CH | 4-MeO | 108–109 | Ethyl acetate-hexane |

REFERENCE EXAMPLE 25

4-Methoxybenzoylacetonitrile

To a solution of methyl 4-methoxybenzoate (7.2 kg) in dimethyl sulfoxide (21.6 L) were added sodium methoxide (3.046 kg) and acetonitrile (2.135 kg) and the mixture was stirred at 110° C. for 2 hours. Then, water (10.83 L) was added dropwise thereto at 15° C. or lower and further acetonitrile (14.4 L) was added to the mixture. Then, 6 N HCl was added thereto to adjust to pH 7.9 and the mixture was extracted with ethyl acetate (72 L). The aqueous layer was further extracted with ethyl acetate (36.32 L). The organic layers were combined and concentrated until the content became 17.39 kg. Methanol (17.84 L) was added thereto and water (17.84 L) was added dropwise. Then, the mixture was stirred at 5° C. for 1 hours and crystals deposited were filtered off and washed with methanol-water (1:1) to obtain the titled compound '6.40 kg, 82.7 g). $^1$H-NMR ($CDCl_3$)δ: 3.90 (3H, s), 4.03 (2H, s), 6.98 (2H, d, J=11.25 Hz), 7.50 (2H, d, J=11.25 Hz).

REFERENCE EXAMPLE 26

2-Amino-4,5-dihydro-3-(4-metholybenzoyl)-7H-thieno[2,3-c]thiopyrane

To a mixture of 4-methoxybenzoylacetonitrile (6.283 kg), 4-oxothiane (5.00 kg), sulfur (1.157 kg) and ethanol (62.83 L) was added dropwise morpholine 3.433 kg) with stirring. After stirring at 60° C. for 5.5 hours, the mixture was cooled to 5° C. and stirred for one hour, Crystals deposited were filtered off, washed with cold ethanol (19.18 L) to obtain the titled compound as yellow crystals (9.557 kg, 88.9%). $^1$H-NMR ($CDCl_3$)δ: 2.31 (2H, t, J=5.4 Hz), 2.61 (2H, t, J=5.4 Hz), 3.65 (2H, s), 3.86 (3H, s), 6.91 (2H, br s), 7.01 (2H, d, J=9.6 Hz), 7.55 (2H, d, J=9.6 Hz).

REFERENCE EXAMPLE 27

3-Chloro-2-chloromethyl-5,8-dihydro-4-(4-methoxyphenyl)-6H-thiopyrano[4',3':4,5]thieno[2,3-b]pyridine To a mixture of 2-amino-4,5-dihydro-3-(4-methoxybenzoyl)-7H-thieno[2,3-c]thiopyrane (9.557 kg), 1,3-dicholoroacetone (4.172 kg) in tetrahydrofuran (48.79 L) was added aluminum chloride (5.424 kg) divided in 4 portions. Then, the mixture was stirred under reflux for 4.5 hours and toluene (38.74 L) was added at 10° C. or lower, followed by dropwise addition of water (47.79 L). After addition of toluene (56.83 L), the mixture was stirred and the organic layer was separated, washed with water, saturated aqueous sodium bicarbonate solution and then water. The solvent was distilled off until the content became 34.61 kg. Methanol (57.34 L) was added dropwise thereto at about 25° C. The mixture was stirred at 5° C. for 1 hour and crystals deposited were filtered off to obtain the titled compound (11.055 kg, 88.3%). $^1$H (CDCl$_3$) δ: 2.18 (2H, t, J=5.7 Hz), 2.68 (2H, t, J=5.7 Hz), 3.90 (5H, s), 4.94 (2H, s), 7.01 (2H, d, J=8.7 Hz), 7.16 (2H, d, J=8.7 Hz).

EXAMPLE 1

Sodium hydride (60% in oil, 360 mg) was added to a solution of benzimidazole (1.1 g) in DMF (40 ml) under ice cooling. After stirring at room temperature for 15 minutes, the compound obtained in Reference Example 15 (3.0 g) was added and then the resulting mixture was stirred at 80° C. for 3 hours. The reaction mixture was poured into water and extracted with ethyl acetate. The ethyl acetate layer was washed with water, dried (MgSO$_4$), and then evaporated under reduced pressure to remove the solvent. The residue was subjected to column chromatography on silica gel to obtain 2-[(1H-benzimidazol-1-yl)methyl]-3-chloro-4-(4-methoxyphenyl)-5,8-dihydro-6H-thiopyrano-[4',3':4,5]thieno[2,3-b]pyridine (1.4 g, 38%) from the eluates with ethyl acetate. It was recrystallized from ethyl acetate-hexane. Colorless crystals. Melting point 201–203° C.

EXAMPLE 2

A mixture of the compound obtained in Reference Example 15 (3.0 g), 2,4-thiazolidinedione (1.8 g), potassium carbonate (2.1 g), and DMF (60 ml) was stirred at 80° C. for 2 hours. The reaction mixture was poured into water and extracted with ethyl acetate. The ethyl acetate layer was washed with water, dried (MgSO$_4$), and then evaporated under reduced pressure to remove the solvent. The residue was subjected to column chromatography on silica gel to obtain 3-{[3-chloro-4-(4-methoxyphenyl)-5,8dihydro-6H-thiopyrano[4',3':4,5]thieno[2,3-b]pyridin-2-yl}methyl-1,3-thiazolidine-2,4-dione (2.9 g, 80%) from the eluates with ethyl acetate-hexane (1:1). It was recrystallized from ethyl acetate-hexane. Colorless prisms. Melting point 208–209° C.

According to the same manner, compounds of Examples 3 to 6, 8 to 17, 35, 36, and 39 described in Table 4 to Table 7 were synthesized.

TABLE 4

| Example No. | Y | R$^1$ | R$^2$ | Melting point (° C.) | Recrystallization solvent |
|---|---|---|---|---|---|
| 1 | S | benzimidazolyl | 4-MeO | 201–203 | Ethyl acetate-hexane |
| 2 | S | thiazolidine-2,4-dione | 4-MeO | 208–209 | Ethyl acetate-hexane |

TABLE 4-continued

[Structure: Y-containing bicyclic thieno-pyridine fused with saturated ring bearing Y; pyridine bears CH2-R1, Cl, and phenyl-R2 substituents]

| Example No. | Y | R¹ | R² | Melting point (° C.) | Recrystallization solvent |
|---|---|---|---|---|---|
| 3 | S | [2-oxo-1,3-oxazolidin-3-yl, 4-oxo] | 4-MeO | 212–213 | Ethyl acetate-hexane |
| 4 | S | [2,4-dioxoimidazolidin-3-yl (NH)] | 4-MeO | 260–262 | Ethyl acetate-hexane |
| 5 | S | [succinimido] | 4-MeO | 239–240 | THF-hexane |
| 6 | S | [phthalimido] | 4-MeO | 234–236 | Ethyl acetate-hexane |
| 7 | S | [1,2,4-triazol-1-yl] | 4-MeO | 198–200 | Ethyl acetate-hexane |
| 8 | S | [succinimido] | 4-PhCH₂O | 246–248 | Ethyl acetate-hexane |
| 9 | S | [2-oxo-1,3-thiazolidin-3-yl, 4-oxo] | 4-PhCH₂O | 225–226 | Ethyl acetate-hexane |

TABLE 4-continued

[Structure: fused thiophene-pyridine with Y-CH2-CH2 ring, S, N, CH2-R¹, Cl, and phenyl-R² substituents]

| Example No. | Y | R¹ | R² | Melting point (° C.) | Recrystallization solvent |
|---|---|---|---|---|---|
| 10 | O | [N-methylsuccinimide group] | 4-MeO | 268–269 | Ethyl acetate-hexane |

TABLE 5

[Same core structure as above]

| Example No. | Y | R¹ | R² | Melting point (° C.) | Recrystallization solvent |
|---|---|---|---|---|---|
| 11 | H₂C=C | [succinimide] | 4-MeO | 187–188 | Ethyl acetate-hexane |
| 12[a)] | Me₂C=C | [succinimide] | 4-MeO | Amorphous solid | |
| 13[b)] | [1,3-dioxolane-C] | [succinimide] | 4-MeO | Amorphous solid | |
| 14 | [1,3-dioxolane-C] | [thiazolidine-2,4-dione] | 4-MeO | 191–192 | Ethyl acetate-hexane |
| 15 | Me₂C | [succinimide] | 4-MeO | 212–213 | Ethyl acetate-hexane |
| 16 | Me₂C | [thiazolidine-2,4-dione] | 4-MeO | 182–184 | Ethyl acetate-hexane |

TABLE 5-continued

| Example No. | Y | R¹ | R² | Melting point (°C.) | Recrystallization solvent |
|---|---|---|---|---|---|
| 17 | Me₂C | (N-methyl oxazolidine-2,4-dione) | 4-MeO | 162–164 | Ethyl acetate-hexane |
| 18 | (O)S | (N-methyl benzimidazole) | 4-MeO | 233–235 | THF-hexane |
| 19 | (O)S | (N-methyl thiazolidine-2,4-dione) | 4-MeO | 252–254 | Ethyl acetate-hexane |
| 20 | (O)S | (N-methyl oxazolidine-2,4-dione) | 4-MeO | 199–201 | Ethyl acetate-hexane | a)¹H NMR (200 MHz, CDCl₃) δ: 1.88 (2H, m), 2.22 (2H, t, J = 6.2 Hz), 2.91 (4H, s), 3.55 (2H, s), 3.90 (3H, s), 4.82 (1H, s), 4.87 (1H, s), 5.02 (2H, s), 6.99 (2H, d, J = 8.8 Hz), 7.14 (2H, d, J = 8.8 Hz).

b)¹H NMR (200 MHz, CDCl₃) δ: 1.70 (2H, t, J = 6.2 Hz), 2.02 (2H, t, J = 6.2 Hz), 2.91 (4H, s), 3.01 (2H, s), 3.90 (3H, s), 3.91–4.03 (4H, m), 5.01 (2H, s), 7.00 (2H, d, J = 8.8 Hz), 7.16 (2H, d, J = 8.8 Hz).

TABLE 6

| Example No. | Y | R¹ | R² | Melting point (°C.) | Recrystallization solvent |
|---|---|---|---|---|---|
| 21 | (O)S | (N-methyl imidazolidine-2,4-dione) | 4-MeO | 251–253 | Ethyl acetate-hexane |

TABLE 6-continued

| Example No. | Y | R¹ | R² | Melting point (° C.) | Recrystallization solvent |
|---|---|---|---|---|---|
| 22 | (O)S | *N-succinimidyl* | 4-MeO | 268–269 | THF-hexane |
| 23 | (O)S | *N-phthalimidyl* | 4-MeO | 275–277 | Ethyl acetate-hexane |
| 24 | (O)S | *1,2,4-triazol-1-yl* | 4-MeO | 184–185 | THF-hexane |
| 25 | (O)S | *N-succinimidyl* | 4-PhCh₂O | 269–271 | Ethyl acetate-hexane |
| 26 | (O)S | *thiazolidine-2,4-dion-3-yl* | 4-PhCH₂O | 268–270 | Ethyl acetate-hexane |
| 27 | (O)₂S | *N-succinimidyl* | 4-MeO | >300 | THF-hexane |
| 28 | (O)₂S | *thiazolidine-2,4-dion-3-yl* | 4-MeO | 234–235 | THF-hexane |

TABLE 6-continued

[Structure: tricyclic thieno-pyridine with Y, R¹ (CH₂-), Cl, and phenyl-R² substituents]

| Example No. | Y | R¹ | R² | Melting point (° C.) | Recrystallization solvent |
|---|---|---|---|---|---|
| 29 | (O)₂S | [N-linked succinimide] | 4-PhCH₂O | 296–298 | Ethyl acetate-hexane |
| 30 | (O)S | [N-linked succinimide] | 4-HO | 274–276 | Methanol-ethyl acetate-hexane |

TABLE 7

| Reference Example No. | Y | R¹ | R² | Melting point (° C.) | Recrystallization solvent |
|---|---|---|---|---|---|
| 31 | (O)S | [N-linked thiazolidine-2,4-dione] | 4-HO | 206–209 | Ethyl acetate-hexane |
| 32 | (O)₂S | [N-linked succinimide] | 4-HO | >300 | Ethyl acetate-hexane |
| 33 | OC | [N-linked succinimide] | 4-MeO | 257–259 | Ethyl acetate-hexane |
| 34 | OC | [N-linked thiazolidine-2,4-dione] | 4-MeO | 203–204 | Ethyl acetate-hexane |

TABLE 7-continued

| Reference Example No. | Y | R¹ | R² | Melting point (° C.) | Recrystallization solvent |
|---|---|---|---|---|---|
| 35 | EtOOC—CH | succinimido | 4-MeO | 180–181 | Ethyl acetate-hexane |
| 36 | PhCH$_2$O$_2$—C—CH | succinimido | 4-MeO | 149–150 | Ethyl acetate-hexane |
| 37 | HOOC-CH | succinimido | 4-MeO | 258–259 | THF-hexane |
| 38 | morpholino-NOC—CH | succinimido | 4-MeO | 170–171 | Chloroform-hexane |
| 39 | PhCH$_2$O—CH | succinimido | 4-MeO | 169–171 | Ethyl acetate-hexane |
| 40 | HO—CH | succinimido | 4-MeO | 218–220 | Ethyl acetate-hexane |

EXAMPLE 7

Sodium hydride (60% in oil, 480 mg) was added to a solution of 1H-1,2,4-triazole (840 mg) in DMF (50 ml) at room temperature and the resulting mixture was stirred at room temperature for 15 minutes. The compound obtained in Reference Example 15 (4.0 g) was added and then the resulting mixture was stirred at 80° C. for 2 hours. The reaction mixture was poured into water and extracted with ethyl acetate. The ethyl acetate layer was washed with water, dried (MgSO$_4$), and then evaporated under reduced pressure to remove the solvent. The residue was subjected to column chromatography on silica gel to obtain 3-chloro-4-(4-methoxyphenyl)-2-(1H-1,2,4-triazol-1-ylmethyl)-5,8-dihydro-6H-thiopyrano[4',3':4,5]thieno[2,3-b]pyridine (3.0 g, 69%) from the eluates with ethyl acetate. It was recrystallized from ethyl acetate-hexane. Yellow crystals. Melting point 198–200° C.

EXAMPLE 18

To a solution of the compound obtained in Example 1 (800 mg) in methylene chloride (20 ml) was added m-chloroperbenzoic acid (70%, 400 mg) under ice cooling and then the resulting mixture was stirred at the same temperature for 1 hour. The reaction mixture was poured into water and extracted with methylene chloride. The methylene chloride layer was washed with a saturated aqueous solution of sodium hydrogen carbonate and water, dried (MgSO$_4$), and then evaporated under reduced pressure to remove the solvent. The residue was subjected to column chromatography on silica gel to obtain 2-[(1H-benzimidazol-1-yl)methyl]-3-chloro-4-(4-methoxyphenyl)-7-oxido-5,8-dihydro-6H-thiopyrano[4',3':4,5]thieno[2,3-b]pyridine (530 mg, 64%) from the eluates with ethyl acetate-methanol (20:1). It was recrystallized from THF-hexane. Colorless prisms. Melting point 233–235° C.

According to the same manner, compounds of Examples 19 to 26 described in Table 5 and Table 6 were synthesized.

EXAMPLE 27

To a solution of the compound obtained in Example 5 (500 mg) in methylene chloride (20 ml) was added m-chloroperbenzoic acid (70%, 609 mg) under ice cooling and then the resulting mixture was stirred at room temperature for 1 hour. The reaction solution was poured into water and extracted with methylene chloride. The methylene chloride layer was washed with a saturated, aqueous solution of sodium hydrogen carbonate and water, dried ($MgSO_4$), and then evaporated under reduced pressure to remove the solvent. The residue was subjected to column chromatography on silica gel to obtain 1-{[3-chloro-4-(4-methoxyphenyl)-7,7-dioxido-5,8-dihydro-6H-thiopyrano[4',3':4,5]thieno[2,3-b]pyridin-2-yl]methyl}-2,5-pyrrolidinedione (295 mg, 55%) from the eluates with ethyl acetate-hexane (1:1). It was recrystallized from THF-hexane. Colorless prisms. Melting point 300° C. or higher.

According to the same manner, compounds of Examples 28 to 29 described in Table 6 were synthesized.

EXAMPLE 30

To a solution of the compound obtained in Example 25 (300 mg) in methylene chloride (20 ml) was added a solution of titanium tetrachloride (620 mg) in methylene chloride (10 ml) under ice cooling and then the resulting mixture was stirred at the same temperature for 8 hours. The reaction mixture was poured into water and extracted with methylene chloride. The methylene chloride layer was washed with a saturated aqueous solution of sodium hydrogen carbonate and water, dried ($MgSO_4$), and then evaporated under reduced pressure to remove the solvent. The residue was subjected to column chromatography on silica gel to obtain 1-{[3-chloro-4-(4-hydroxyphenyl)-7-oxido-5,8-dihydro-6H-thiopyrano[4',3':4,5]thieno[2,3-b]pyridin-2-yl]methyl}-2,5-pyrrolidinedione (130 mg, 52%) from the eluates with ethyl acetate-methanol (9:1). It was recrystallized from methanol-ethyl acetate-hexane. Colorless prisms. Melting point 274–276° C.

According to the same manner, compounds of Examples 31 and 32 described in Table 7 were synthesized.

EXAMPLE 33

A mixture of the compound obtained in Example 13 (2.4 g), 10% aqueous hydrochloric acid (10 ml), and dioxane (25 ml) was stirred at 60° C. for 2 hours and then evaporated under reduced pressure to remove the solvent. The residue was diluted with methylene chloride and the methylene chloride solution was washed with water, dried ($MgSO_4$), and then evaporated under reduced pressure to remove the solvent. The residue was subjected to column chromatography on silica gel to obtain 1-{[3-chloro-4-(4-methoxyphenyl)-7-oxo-5,6,7,8-tetrahydro[1]benzothieno[2,3-b]pyridin-2-yl]methyl}-2,5-pyrrolidinedione (1.8 g, 86%) from the eluates with chloroform-ethyl acetate (4:1). It was recrystallized from ethyl acetate-hexane. Colorless prisms. Melting point 257–258° C.

EXAMPLE 34

According to the same manner as that described in Example 33, 3-{[chloro-4-(4-methoxyphenyl)-7-oxo-5,6,7,8-tetrahydro[1]benzothieno[2,3-b]pyridin-2-yl]methyl}-1,3-thiazolidine-2,4-dione was obtained except that the compound obtained in Example 14 is used. It was recrystallized from ethyl acetate-hexane. Colorless prisms. Melting point 203–204° C.

EXAMPLE 37

To a mixture of the compound obtained in Example 36 (3.4 g), 10% palladium carbon (containing 50% water, 3.0 g), THF (30 ml), and acetic acid (60 ml) was added formic acid (6 ml) with stirring at room temperature and then the stirring was continued at the same temperature for 3 hours. After the catalyst was separated by filtration, the filtrate was evaporated under reduced pressure. To the residue was added diethyl ether-methanol (10:1, 50 ml) and the resulting mixture was stirred at room temperature for 30 minutes. The precipitated crystals were collected by filtration and washed with diethyl ether-methanol (10:1) to obtain 3-chloro-2-[(2,5-dioxopyrrolidin-1-yl)methyl]-5,6,7,8-tetrahydro-4-(4-methoxyphenyl)[1]benzothieno[2,3-b]pyridine-7-carboxylic acid (2.6 g, 92%). It was recrystallized from THF-hexane. Colorless prisms. Melting point 258–259° C.

EXAMPLE 38

A mixture of the compound obtained in Example 37 (500 mg), morpholine (99 mg), N,N-dimethylaminopyridine (13 mg), 1-(3-dimethylaminopropyl)-3-ethylcarbodiimide hydrochloride (197 mg), and DMF (10 ml) was stirred at room temperature for 10 hours. The reaction mixture was poured into water and extracted with ethyl acetate. The ethyl acetate layer was washed with water, dried ($MgSO_4$), and then evaporated under reduced pressure to remove the solvent. The residue was subjected to column chromatography on silica gel to obtain 1-{[3-chloro-4-(4-methoxyphenyl)-7-[(4-morpholinyl)carbonyl]-5,6,7,8-tetrahydro[1]benzothieno[2,3-b]pyridin-2-yl]methyl}-2,5-pyrrolidinedione (2.6 g, 92%) from the eluates with ethyl acetate. It was recrystallized from chloroform-hexane. Colorless prisms. Melting point 170–171° C.

EXAMPLE 40

To a mixture of the compound obtained in Example 39 (1.2 g), 10% palladium carbon (containing 50% water, 1.2 g), and acetic acid (70 ml) was added formic acid (10 ml) with stirring at room temperature and then the stirring was continued at the same temperature for 2 hours. After the catalyst was separated by filtration, the filtrate was evaporated under reduced pressure. To the residue was added ethyl acetate and the resulting solution was washed with a 5% aqueous ammonia solution and water, dried ($MgSO_4$), and then evaporated under reduced pressure to remove the solvent. The residue was subjected to column chromatography on silica gel to obtain 1-{[3-chloro-7-hydroxy-4-(4-methoxyphenyl)-5,6,7,8-tetrahydro[1]-benzothieno[2,3-b]pyridin-2-yl]methyl}-2,5-pyrrolidinedione (1.8 g, 86%) from the eluates with ethyl acetate-hexane (2:1). It was recrystallized from ethyl acetate-hexane. Colorless prisms. Melting point 218–220° C.

EXAMPLE 41

To a solution of the compound obtained in Example 33 (500 mg) and methyl iodide (470 mg) in DMF (15 ml) was added DBU (420 mg) under ice cooling and then the resulting mixture was stirred at the same temperature for 2 hours. The reaction mixture was poured into a saturated aqueous solution of ammonium chloride (30 ml) and extracted with ethyl acetate. The ethyl acetate layer was washed with water, dried (MgSO$_4$), and then evaporated under reduced pressure to remove the solvent. The residue was subjected to column chromatography on silica gel to obtain 1-{[3-chloro-4-(4-methoxyphenyl)-8,8-dimethyl-7-oxo-5,6,7,8-tetrahydro[1]benzothieno[2,3-b]pyridin-2-yl]methyl}-2,5-pyrrolidinedione:

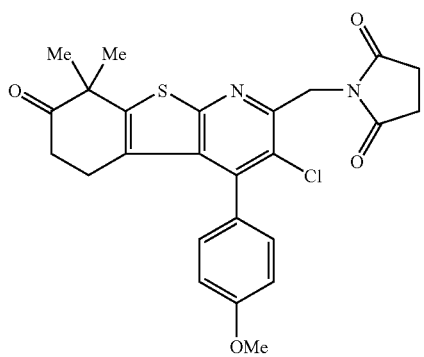

(291 mg, 55%) from the eluates with ethyl acetate-hexane (3:1). It was recrystallized from ethyl acetate-hexane. Colorless prisms. Melting point 245–246° C.

EXAMPLE 42

According to the same manner as that described in Example 41, 3-{[3-chloro-4-(4-methoxyphenyl)-8,8-dimethyl-7-oxo-5,6,7,8-tetrahydro[1]benzothieno[2,3-b]pyridin-2-yl]methyl}-1,3-thiazolidine-2,4-dione:

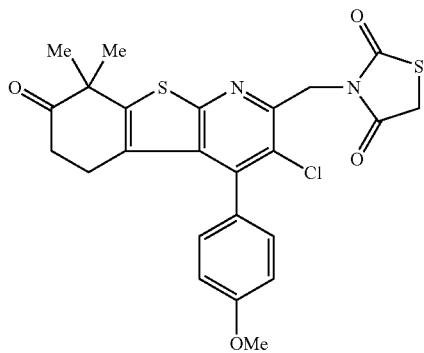

was obtained except that the compound obtained in Example 34 was used. It was recrystallized from ethyl acetate-hexane. Colorless prisms. Melting point 211–212° C.

EXAMPLE 43

A mixture of the compound obtained in Reference Example 14 (512 mg), succinimide (198 mg), potassium carbonate (276 mg), and DMF (5 ml) was stirred at 80° C. for 1 hour, then was poured into water, and extracted with ethyl acetate. The ethyl acetate layer was washed with water, dried (MgSO$_4$), and then evaporated under reduced pressure to remove the solvent. The residue was subjected to column chromatography on silica gel to obtain 1-{[7-(benzyloxy)-3-chloro-4-(4-methoxyphenyl)-6,6-dimethyl-5,6,7,8-tetrahydro-[1]benzothieno[2,3-b]pyridin-2-yl]methyl}-2,5-pyrrolidinedione:

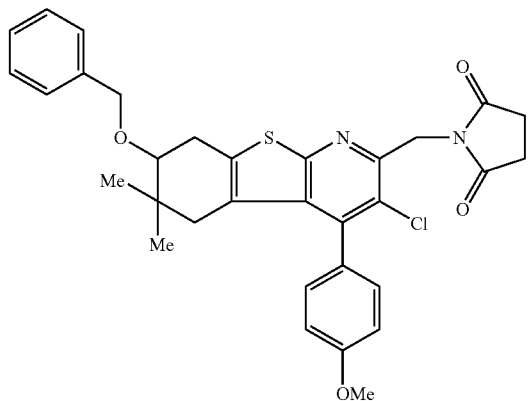

(554 mg, 96%) from the eluates with ethyl acetate-hexane (1:2). It was recrystallized from ethyl acetate-hexane. Colorless prisms. Melting point 221–223° C.

EXAMPLE 44

To a mixture of the compound obtained in Example 43 (480 mg), 10% palladium carbon (containing 50% water, 480 mg), and THF (20 ml) was added formic acid (10 ml) with stirring at room temperature. After the stirring was continued at room temperature for 5 hours, the catalyst was separated by filtration and the filtrate was evaporated under reduced pressure. The residue was dissolved in ethyl acetate-THF (5:1) and the resulting mixture was washed with a saturated aqueous solution of sodium hydrogen carbonate and water, dried (MgSO$_4$), and then evaporated under reduced pressure to remove the solvent. The residue was subjected to column chromatography on silica gel to obtain 1-{[3-chloro-7-hydroxy-4-(4-methoxyphenyl)-6,6-dimethyl-5,6,7,8-tetrahydro[1]benzothieno[2,3-b]pyridin-2-yl]methyl}-2,5-pyrrolidinedione:

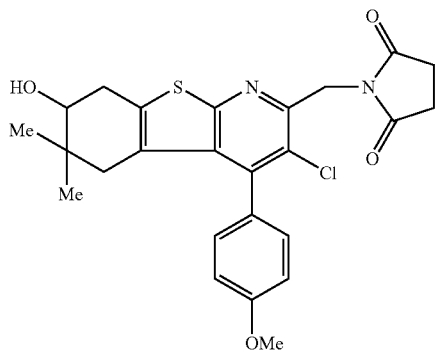

(221 mg, 55%) as a colorless powder from the eluates with ethyl acetate-hexane (1:1). Melting point 227–229° C.

EXAMPLE 45

A solution of dimethyl sulfoxide (30 mg) in methylene chloride (1 ml) was added to a solution of oxalyl chloride (37 mg) in methylene chloride (4 ml) at −78° C. under a nitrogen atmosphere. After stirring at the same temperature for 1 hour, a solution of the compound obtained in Example 13 (70 mg) in methylene chloride (4 ml) was added thereto and then the stirring was continued at −78° C. for 1 hour. The reaction temperature was raised to at −30° C. and, after stirring at 30 minutes, triethylamine (150 μl) was added thereto and then the solution temperature was slowly raised to at 0° C. The reaction mixture was poured into water and extracted with ethyl acetate. The ethyl acetate layer was washed with water, dried (MgSO$_4$), and then evaporated under reduced pressure to remove the solvent. The residue was subjected to column chromatography on silica gel to obtain 1-{[3-chloro-4-(4-methoxyphenyl)-6,6-dimethyl-7-oxo-5,6,7,8-tetrahydro [1]benzothieno[2,3-b]pyridin-2-yl]methyl}-2,5-pyrrolidinedione:

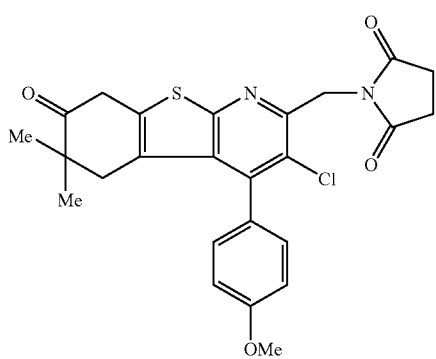

(30 mg, 62%) from the eluates with ethyl acetate-hexane (1:2). It was recrystallized from ethanol-hexane. Colorless prisms. Melting point 222–224° C.

EXAMPLE 46

A solution of 400 mg of the compound obtained in Example 22 in 350 ml of 2-propanol and 100 ml of hexane was fractionated by high performance liquid chromatography (HPLC) [column: CHIRALCEL OD 50 mmφ×500 mm (manufactured by Daicel Kagaku Kogyo Kabushiki Kaisha), temperature: 20° C., mobile phase: hexane/2-propanol=6/4, flow rate: 100 ml/minute, detection wavelength: 254 nm, and 1 shot: about 40 mg]. The fractions were concentrated and then dissolved in 50 ml of ethanol. The resulting solution was filtered through a 0.45-μm filter and then concentrated to dryness. To the residue was added hexane and the resulting mixture was again concentrated to dryness to obtain a white powder.

There were obtained 153 mg (optical purity of 99.4% ee) of an enantiomer having a shorter retention time whose optical rotation was toward (+)-direction of the optical rotation, (R)-1-{[3-chloro-4-(4-methoxyphenyl)-7-oxido-5,8-dihydro-6H-thiopyrano[4',3':4,5]thieno[2,3-b]pyridin-2-yl]methyl}-2,5-pyrrolidinedione, and 152 mg (optical purity of 99.8% ee) of an enantiomer having a longer retention time whose optical rotation was toward (−)-direction, (S)-1-{[3-chloro-4-(4-methoxyphenyl)-7-oxido-5,8-dihydro-6H-thiopyrano[4',3':4,5]thieno[2,3-b]pyridin-2-yl]methyl}-2,5-pyrrolidinedione. The determination of the optical purity was carried out by HPLC using a chiral column (column: CHIRALPAK AD 4.6 mmφ×250 mm (manufactured by Daicel Kagaku Kogyo Kabushiki Kaisha), temperature: about 20° C., mobile phase: hexane/ethanol=4/6, flow rate: 0.5 ml/minute, and detection wavelength: 254 nm).

EXAMPLE 47

A solution of 1.1 g of the compound obtained in Example 22 in 500 ml of ethanol and 500 ml of 2-propanol was concentrated to make the liquid volume about ½. The resulting concentrate was fractionated by high performance liquid chromatography (HPLC) [column: CHIRALPAK AD 50 mmφ×500 mm (manufactured by Daicel Kagaku Kogyo Kabushiki Kaisha), temperature: 20° C., mobile phase: hexane/ethanol=4/6, flow rate: 70 ml/minute, detection wavelength: 254 nm, and 1 shot: about 0.8 g]. The fractions were concentrated and then dissolved in ethanol. The resulting solution was filtered through a 0.45-μm filter and then concentrated to dryness. To the residue was added hexane and the resulting mixture was again concentrated to dryness to obtain a white powder.

According to the same operation, there were obtained from 3.1 g of the racemate 1.39 g (optical purity of >99.9% ee) of an enantiomer having a shorter retention time whose optical rotation was toward (+)-direction, (R)-1-{[3-chloro-4-(4-methoxyphenyl)-7-oxido-5,8-dihydro-6H-thiopyrano[4',3':4,5]thieno[2,3-b]pyridin-2-yl]methyl}-2,5-pyrrolidinedione, and 1.47 g (optical purity of 99.4% ee) of an enantiomer having a longer retention time whose optical rotation was toward (−)-direction, (S)-1-{[3-chloro-4-(4-methoxyphenyl)-7-oxido-5,8-dihydro-6H-thiopyrano-[4',3':4,5]thieno[2,3-b]pyridin-2-yl]methyl}-2,5-pyrrolidinedione.

EXAMPLE 48

A solution of 980 mg of the compound obtained in Example 19 in 700 ml of 2-propanol and 300 ml of ethanol was fractionated by high performance liquid chromatography (HPLC) [column: CHIRALCEL OD 50 mmφ×500 mm (manufactured by Daicel Kagaku Kogyo Kabushiki Kaisha), temperature: 20° C., mobile phase: hexane/2-propanol=6/4, flow rate: 100 ml/minute, detection wavelength: 254 nm, and 1 shot: about 40 mg]. The fractions were concentrated and then dissolved in ethanol. The resulting solution was filtered through a 0.45-μm filter and then concentrated to dryness. To the residue was added hexane and the resulting mixture was again concentrated to dryness to obtain a white powder.

There were obtained 188 mg (optical purity of 99.4% ee) of an enantiomer having a shorter retention time whose optical rotation was toward (+)-direction, (R)-3-{[3-chloro-4-(4-methoxyphenyl)-7-oxido-5,8-dihydro-6H-thiopyrano[4',3':4,5]thieno[2,3-b]pyridin-2-yl]methyl}-1,3-thiazoldine-2,4-dione, and 153 mg (optical purity of 99.0% ee) of an enantiomer having a longer retention time whose optical rotation was toward (−)-direction, (S)-3-{[3-chloro-4-(4-methoxyphenyl)-7-oxido-5,8-dihydro-6H-thiopyrano[4',3':4,5]thieno[2,3-b]pyridin-2-yl]methyl}-1,3-thiazoldine-2,4-dione.

EXAMPLE 49

A solution of 1.0 g of the compound obtained in Example 19 in 900 ml of ethanol and 100 ml of acetonitrile was concentrated to make the liquid volume about ½. The resulting concentrate was fractionated by HPLC [column: CHIRALPAK AD 50 mmφ×500 mm (manufactured by Daicel Kagaku Kogyo Kabushiki Kaisha), temperature: 20° C., mobile phase: hexane/ethanol=4/6, flow rate: 100 ml/minute, detection wavelength: 254 nm, and 1 shot: about 1.2 g]. The fractions were concentrated and then dissolved in ethanol. The resulting solution was filtered through a 0.45-μm filter and then concentrated to dryness. To the residue was added hexane and the resulting mixture was again concentrated to dryness to obtain a white powder.

According to the same operation, there were obtained from 2.5 g of the racemate 1.21 g (optical purity of >99.9% ee) of an enantiomer having a shorter retention time whose optical rotation was toward (+)-direction, (R)-3-{[3-chloro-4-(4-methoxyphenyl)-7-oxido-5,8-dihydro-6H-thiopyrano[4',3':4,5]thieno[2,3-b]pyridin-2-yl]methyl}-1,3-thiazoldine-2,4-dione, and 1.14 g (optical purity of 99.8% ee) of an enantiomer having a longer retention time whose optical rotation was toward (−)-direction, (S)-3-{[3-chloro-4-(4-methoxyphenyl)-7-oxido-5,8-dihydro-6H-thiopyrano[4',3':4,5]thieno[2,3-b]pyridin-2-yl]methyl}-1,3-thiazoldine-2,4-dione.

EXAMPLE 50

A mixture of 10 mg of the compound obtained in Example 47, (R)-1-{[3-chloro-4-(4-methoxyphenyl)-7-oxido-5,8-dihydro-6H-thiopyrano[4',3':4,5]thieno[2,3-b]pyridin-2-yl]methyl}-2,5-pyrrolidinedione, 90 mg of lactose, and 70 mg of microcrystalline cellulose was granulated with a solution of 1.4 mg of hydroxypropyl cellulose in 70 μl of water. The granules were encapsulated into a gelatin capsule.

EXAMPLE 51

A mixture of 10 mg of the compound obtained in Example 47, (S)-1-{[3-chloro-4-(4-methoxyphenyl)-7-oxido-5,8-dihydro-6H-thiopyrano[4',3':4,5]thieno[2,3-b]pyridin-2-yl]methyl}-2,5-pyrrolidinedione, 90 mg of lactose, and 70 mg of microcrystalline cellulose was granulated with a solution of 1.4 mg of hydroxypropyl cellulose in 70 μl of water. The granules were encapsulated into a gelatin capsule.

EXAMPLE 52

A mixture of 10 mg of the compound obtained in Example 49, (R)-3-{[3-chloro-4-(4-methoxyphenyl)-7-oxido-5,8-dihydro-6H-thiopyrano[4',3':4,5]thieno[2,3-b]pyridin-2-yl]methyl}-1,3-thiazoldine-2,4-dione, 90 mg of lactose, and 70 mg of microcrystalline cellulose was granulated with a solution of 1.4 mg of hydroxypropyl cellulose in 70 μl of water. The granules were encapsulated into a gelatin capsule.

EXAMPLE 53

A mixture of 10 mg of the compound obtained in Example 49, (S)-3-{[3-chloro-4-(4-methoxyphenyl)-7-oxido-5,8-dihydro-6H-thiopyrano[4',3':4,5]thieno[2,3-b]pyridin-2-yl]methyl}-1,3-thiazoldine-2,4-dione, 90 mg of lactose, and 70 mg of microcrystalline cellulose was granulated with a solution of 1.4 mg of hydroxypropyl cellulose in 70 μl of water. The granules were encapsulated into a gelatin capsule.

EXAMPLE 54

A mixture of 10 mg of the compound obtained in Example 47, (R)-1-{[3-chloro-4-(4-methoxyphenyl)-7-oxido-5,8-dihydro-6H-thiopyrano[4',3':4,5]thieno[2,3-b]pyridin-2-yl]methyl}-2,5-pyrrolidinedione, 35 mg of lactose, 150 mg of corn starch, and 20 mg of microcrystalline cellulose was granulated with a solution of 1.4 mg of hydroxypropyl cellulose in 70 μl of water. To the granules were added 10 mg of microcrystalline cellulose and 2.5 mg of magnesium stearate, followed by mixing. The resulting mixture was subjected to compression molding to prepare a tablet.

EXAMPLE 55

A mixture of 10 mg of the compound obtained in Example 47, (S)-1-{[3-chloro-4-(4-methoxyphenyl)-7-oxido-5,8-dihydro-6H-thiopyrano[4',3':4,5]thieno[2,3-b]pyridin-2-yl]methyl}-2,5-pyrrolidinedione, 35 mg of lactose, 150 mg of corn starch, and 20 mg of microcrystalline cellulose was granulated with a solution of 1.4 mg of hydroxypropyl cellulose in 70 μl of water. To the granules were added 10 mg of microcrystalline cellulose and 2.5 mg of magnesium stearate, followed by mixing. The resulting mixture was subjected to compression molding to prepare a tablet.

EXAMPLE 56

A mixture of 10 mg of the compound obtained in Example 49, (R)-3-{[3-chloro-4-(4-methoxyphenyl)-7-oxido-5,8-dihydro-6H-thiopyrano[4',3':4,5]thieno[2,3-b]pyridin-2-yl]methyl}-1,3-thiazoldine-2,4-dione, 35 mg of lactose, 150 mg of corn starch, and 20 mg of microcrystalline cellulose was granulated with a solution of 1.4 mg of hydroxypropyl cellulose in 70 μl of water. To the granules were added 10 mg of microcrystalline cellulose and 2.5 mg of magnesium stearate, followed by mixing. The resulting mixture was subjected to compression molding to prepare a tablet.

EXAMPLE 57

A mixture of 10 mg of the compound obtained in Example 49, (S)-3-{[3-chloro-4-(4-methoxyphenyl)-7-oxido-5,8-dihydro-6H-thiopyrano[4',3':4,5]thieno[2,3-b]pyridin-2-yl]methyl}-1,3-thiazoldine-2,4-dione, 35 mg of lactose, 150 mg of corn starch, and 20 mg of microcrystalline cellulose was granulated with a solution of 1.4 mg of hydroxypropyl cellulose in 70 μl of water. To the granules were added 10 mg of microcrystalline cellulose and 2.5 mg of magnesium stearate, followed by mixing. The resulting mixture was subjected to compression molding to prepare a tablet.

EXAMPLE 58

To a mixture of the compound obtained in Example 23 (4.5 g), ethanol (100 ml), and THF (100 ml) was added hydrazine hydrate (20 ml) at room temperature. This mixture was stirred at 70° C. for 2 hours and then evaporated under reduced pressure. The residue was diluted with chloroform and the resulting solution was washed with water, dried (MgSO$_4$), and then evaporated under reduced pressure to remove the solvent to obtain 2-aminomethyl-3-chloro-4-(4-methoxyphenyl)-7-oxido-5,8-dihydro-6H-thiopyrano[4',3':4,5]thieno[2,3-b]pyridine:

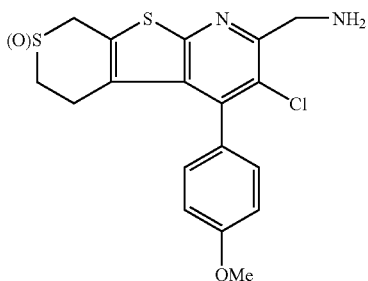

(3.0 g, 89%). It was recrystallized from ethyl acetate-hexane. Colorless prisms. Melting point 300° C. or higher.

EXAMPLE 59

To a mixture of the compound obtained in Example 33 (1.5 g), N-fluorobis(benzenesulfon)imide (2.6 g), and DMF (45 ml) was added DBU (2.0 g) under ice cooling and then the resulting mixture was stirred for 3 hours. The reaction mixture was poured into a saturated aqueous solution of ammonium chloride (150 ml) and extracted with ethyl acetate. The ethyl acetate layer was washed with water, dried (MgSO₄), and then evaporated under reduced pressure to remove the solvent. The residue was subjected to column chromatography on silica gel and to obtain 1-{[3-chloro-8-fluoro-7-hydroxy-4-(4-methoxyphenyl)-[1]benzothieno[2,3-b]pyridin-2-yl]methyl}-2,5-pyrrolidinedione:

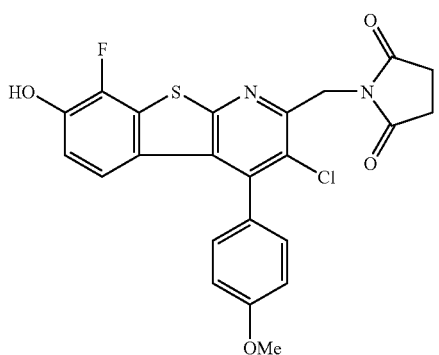

(750 mg, 48%) from the eluates with chloroform-hexane-ethyl acetate (2:2:1). It was recrystallized from THF-hexane. Colorless prisms. Melting point 294–295° C.

EXAMPLE 60

To a solution of the compound obtained in Example 59 (250 mg) in DMF (5 ml) was added sodium hydride (60% in oil, 25 mg) under ice cooling. After stirring at room temperature for 10 minutes, iodomethane (150 mg) was added thereto and then the stirring was continued for 30 minutes. The reaction mixture was poured into water and extracted with ethyl acetate. The ethyl acetate layer was washed with water, dried (MgSO₄), and then evaporated under reduced pressure to remove the solvent to obtain 1-{[3-chloro-8-fluoro-7-methoxy-4-(4-methoxyphenyl)[1]-benzothieno[2,3-b]pyridin-2-yl]methyl}-2,5-pyrrolidinedione (190 mg, 74%). It was recrystallized from THF-hexane. Colorless prisms. Melting point 215–216° C.

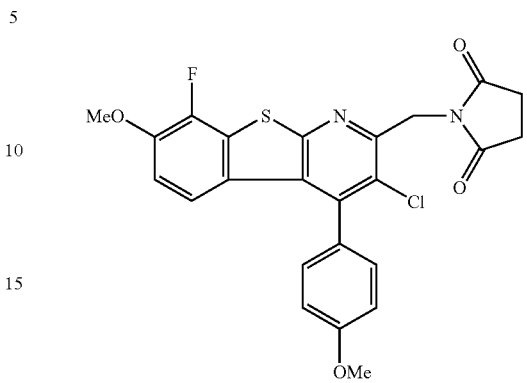

EXAMPLE 61

To a mixture of the compound obtained in Example 45 (200 mg), iodomethane (176 mg), and DMF (6 ml) was added DBU (158 mg) under ice cooling. The reaction solution was stirred at 0° C. for 20 minutes, then poured into a saturated aqueous solution of ammonium chloride, and extracted with ethyl acetate-THF (5:1). The extract was washed with water, dried (MgSO₄), and then evaporated under reduced pressure to remove the solvent. The residue was subjected to column chromatography on silica gel to obtain 1-{[3-chloro-4-(4-methoxyphenyl)-6,6,8,8-tetramethyl-7-oxo-5,6,7,8-tetrahydro[1]benzothieno[2,3-b]pyridin-2-yl]methyl}-2,5-pyrrolidinedione:

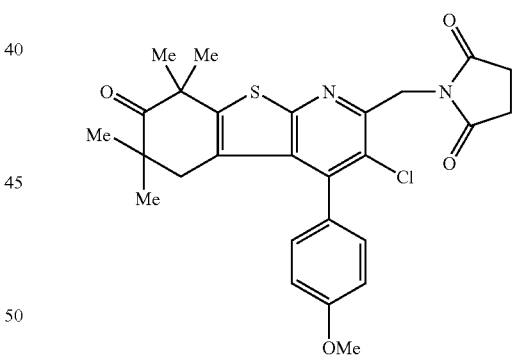

(140 mg, 66%) from the eluates with ethyl acetate-hexane. A colorless powder. Melting point 214–216° C.

EXAMPLE 62

To a mixture of the compound obtained in Example 45 (220 mg), N-fluorobis(benzenesulfon)imide (391 mg), and DMF (6 ml) was added DBU (158 mg) under ice cooling. The reaction mixture was stirred at 0° C. for 30 minutes and then poured into a saturated aqueous solution of ammonium chloride and extracted with ethyl acetate-THF (5:1). The extract was washed with water, dried (MgSO₄), and then evaporated under reduced pressure to remove the solvent.

The residue was subjected to column chromatography on silica gel to obtain 1-{[3-chloro-8,8-difluoro-4-(4-methoxyphenyl)-6,6-dimethyl-7-oxo-5,6,7,8-tetrahydro-[1]benzothieno[2,3-b]pyridin-2-yl]methyl}-2,5-pyrrolidinedione:

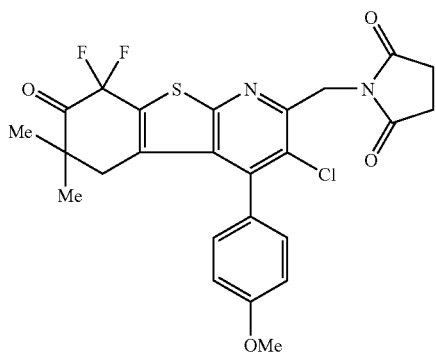

(85 mg) from the eluates with ethyl acetate-hexane-methanol (1:2:0.1). It was recrystallized from ethanol-isopropyl ether. Colorless prisms. Melting point of 200–202° C.

EXAMPLE 63

A mixture of the compound obtained in Example 33 (2.0 g), hydroxylamine hydrochloride (673 mg), water (5 ml), methanol (5 ml), and THF (40 ml) was heat under reflux for 2 hours and then evaporated under reduced pressure to remove the solvent. The residue was dissolved in methylene chloride and the resulting solution was washed with a saturated, aqueous solution of sodium hydrogen carbonate and water, dried (MgSO$_4$), and then evaporated under reduced pressure to remove the solvent. The residue was subjected to column chromatography on silica gel to obtain (Z)-1-{[3-chloro-7-(hydroxyimino)-4-(4-methoxyphenyl)-5,6,7,8-tetrahydro[1]benzothieno[2,3-b]pyridin-2-yl]methyl}-2,5-pyrrolidinedione:

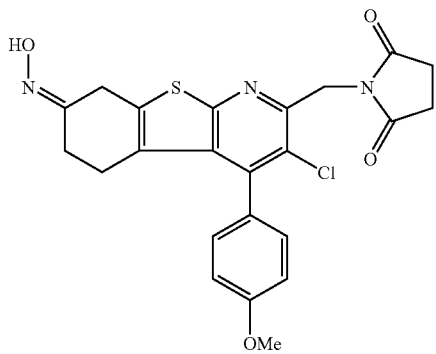

(810 mg, 39%) from the eluates with ethyl acetate-chloroform (1:1) as a less polar portion. It was recrystallized from THF-hexane. Colorless prisms. Melting point 248–249° C.

In addition, (E)-1-{[3-chloro-7-(hydroxyimino)-4-(4-methoxyphenyl)-5,6,7,8-tetrahydro[1]benzothieno[2,3-b]pyridin-2-yl]methyl}-2,5-pyrrolidinedone:

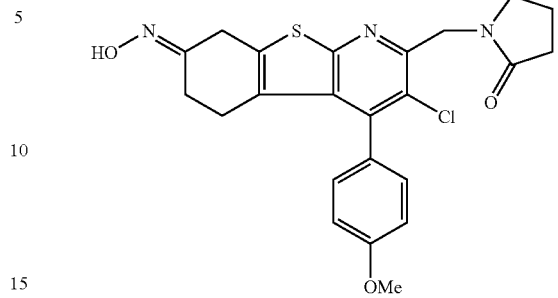

(226 mg, 11%) was obtained from a more polar portion. It was recrystallized from THF-hexane. Colorless prisms. Melting point 250–251° C.

EXAMPLE 64

To a mixture of the compound obtained in Example 32 (150 mg), triethylamine (41 mg), methylene chloride (4 ml) and DMF (0.4 ml) was added acetyl chloride (27 mg) under ice-cooling. The reaction mixture was stirred at room temperature for 30 minutes, poured into water and then extracted with ethyl acetate. The ethyl acetate layer was washed with water, and dried (MgSO$_4$). The solvent was distilled off under reduce pressure to obtain 4-{3-chloro-2-[(2,5-dioxo-1-pyrrolidinyl)methyl]-7,7-dioxido-5,8-dihydro-6H-thiopyrano[4',3':4,5]thieno[2,3-b]pyridin-4-yl}phenylacetate (75 mg, 46%). It was recrystallized from acetone-hexane. Colorless prisms. Melting point 272–273° C.

According to the same manner, compounds of Examples 65 to 72 shown in Table 8 were synthesized.

TABLE 8

| Example No. | R | Melting point (° C.) | Recrystallization solvent |
|---|---|---|---|
| 64 | COMe | 272–273 | acetone-hexane |
| 65 | COEt | 268–269 | acetone-hexane |
| 66 | CO$^t$Bu | 305–306 | ethyl acetate-hexane |
| 67 | CO(CH$_2$)$_{14}$Me | 160–161 | acetone-hexane |
| 68 | COCH$_2$OMe | 207–208 | ethyl acetate-hexane |
| 69 | COCH$_2$Cl | 167–168 | acetone |

TABLE 8-continued

[Structure: thiopyrano-thieno-pyridine core with SO2, Cl, and N-succinimidylmethyl substituents, 4-phenyl-OR group]

| Example No. | R | Melting point (° C.) | Recrystallization solvent |
|---|---|---|---|
| 70 | CO—C6H4—CF3 | 281–282 | THF-hexane |
| 71 | CO—C6H3(CF3)2 | 178–179 | ethyl acetate-hexane |
| 72 | CO—C6F5 | 156–157 | acetone-hexane |
| 73 | COCH2NMe2 • HCl | 199–200 | ethanol-hexane |
| 74 | P(O)Me2 | 253–254 | THF-hexane |
| 75 | P(O)(cyc.Hex)2 | 167–168 | ethyl acetate-hexane |
| 76 | P(O)(OEt)2 | 204–205 | ethyl acetate-hexane |
| 77 | P(O)(OPh)2 | 200–201 | THF-hexane |
| 78 | P(O)(OCH2CH2CH2Me)2 | amorphous solids | IR (KBr): 1775, 1713, 1329, 1279 cm$^{-2}$ |
| 79 | P(O)(OCH2CHMe2)2 | amorphous solids | IR (KBr): 1775, 1713, 1331, 1275 cm$^{-2}$ |
| 80 | P(O)(OCH2CH2CH2CH2Me)2 | amorphous solids | IR (KBr): 1775, 1711, 1324, 1277 cm$^{-2}$ |
| 81 | CONHCH2CH2Me | 164–165 | THF-hexane |
| 82 | CONHCH2CH2CH2Me | 150–152 | ethyl acetate-hexane |
| 83 | CONH(cyc.Hex) | 260–261 | THF-hexane |
| 84 | CONHCH2COOEt | 202–203 | ethyl acetate-hexane |
| 85 | SO2CHMe2 | 288–289 | THF-hexane |
| 86 | SO2CH2CHMe2 | 215–216 | acetone-hexane |
| 87 | CO—N(morpholino) | 327–328 | DMSO-water |
| 88 | CONMe2 | 290–291 | chloroform-hexane |

EXAMPLE 73

A mixture of the compound obtained in Example 32 (462 mg), dimethylglycine (300 mg), 1-ethyl-3-(3-dimethylaminopropyl)carbodiimide hydrochloride (WSC, 556 mg) and pyridine (8 ml) was stirred at room temperature for 10 hours and then the solvent was removed under reduced pressure. The residue was diluted with ethyl acetate (10 ml) and the mixture was washed with water and dried (MgSO4). The solvent was removed under reduced pressure and the residue (210 mg) was dissolved in chloroform (2 ml). To the solution was added 4 N hydrochloric acid-ethyl acetate solution (0.09 ml) with stirring under ice-cooling and the mixture was further stirred for 10 minutes. The reaction mixture was concentrated under reduced pressure to obtain crystals of 4-{3-chloro-2-[(2,5-dioxo-1-pyrrolidinyl)-methyl]-7,7-dioxido-5,8-dihydro-6H-thiopyrano[4',3':4,5]-thieno[2,3-b]pyridin-4-yl}phenyl (dimethylamino)acetate hydrochloride. It was recrystallized from ethanol-hexane. Colorless crystals. Melting point 199–200° C.

EXAMPLE 74

To a mixture of the compound obtained in Example 32 (100 mg), triethylamine (70 mg) and methylene chloride (3 ml) was added dimethylphosphinic chloride (97%, 73 mg) under ice-cooling. The reaction mixture was stirred at room temperature for 2 hours, poured into water, and extracted with ethyl acetate. The ethyl acetate layer was washed with water and dried (MgSO4) and the solvent was distilled off under reduced pressure. The residue was subjected to silica gel column chromatography to obtain 4-{3-chloro-2-{(2,5-dioxo-1-pyrrolidinyl)methyl]-7,7-dioxido-5,8-dhydro-6H-thiopyrano[4',3':4,5]thieno[2,3-b]pyridin-4-yl}phenyldimethylphosphinate (67 mg, 58%) from the fraction eluted with ethyl acetate-methanol (10:1). It was recrystallized from THF-hexane. Colorless prisms. Melting point 253–254° C.

According to the same manner, the compound of Example 75 shown in Table 8 was synthesized.

EXAMPLE 76

To a mixture of the compound obtained in Example 32 (300 mg), THF (6 ml) and DMF (0.5 ml) was added sodium hydride (60% in oil, 37 mg) under ice-cooling and then the mixture was stirred for 15 minutes. Diethylphosphoryl chloride (217 mg) was added thereto and the stirring was continued for additional 3 hours under ice-cooling. The reaction mixture was poured into water and extracted with ethyl acetate. The ethyl acetate layer was washed with water and dried (MgSO4) and the solvent was distilled off under reduced pressure. The residue was subjected to silica gel column chromatography to obtain 4-{3-chloro-2-[(2,5-dioxo-1-pyrrolidinyl)methyl]-7,7-dioxido-5,8-dihydro-6H-thiopyrano[4',3':4,5]thieno[2,3-b]pyridin-4-yl}phenyldiethylphosphate (200 mg, 52%) from the fraction eluted with ethyl acetate-hexane (4:1). It was recrystallized from ethyl acetate-hexane. Colorless prisms. Melting point 204–205° C.

According to the same manner, the compounds of Examples 77 to 80 shown in Table 8 were synthesized.

EXAMPLE 81

To a mixture of the compound obtained in Example 32 (300 mg), triethylamine (127 mg) and methylene chloride (6 ml) was added propylisocyanate (80 mg) under ice-cooling.

The reaction mixture was stirred at room temperature for 10 hours, poured into water, and then extracted with ethyl acetate. The ethyl acetate layer was washed with water, dried (MgSO$_4$) and the solvent was distilled off under reduced pressure. The residue was subjected to silica gel column chromatography to obtain 4-{3-chloro-2-[(2,5-dioxo-1-pyrrolidinyl)methyl]-7,7-dioxido-5,8-dihydro-6H-thiopyrano[4',3':4,5]thieno[2,3-b]pyridin-4-yl}phenyl-propylcarbamate (220 mg. 62%) from the fraction eluted with ethyl acetate-hexane (2:1). It was recrystallized from THF-hexane. Colorless prisms. Melting point 164–165° C.

According to the same manner, the compounds of Examples 82 to 84 shown in Table 8 were synthesized.

EXAMPLE 85

To a mixture of the compound obtained in Example 32 (250 mg), triethylamine (106 mg) and methylene chloride (5 ml) was added isopropylsulfonyl chloride (112 mg) under ice-cooling. The reaction mixture was stirred at room temperature for 3 hours, poured into water and extracted with ethyl acetate. The ethyl acetate layer was washed with water and dried (MgSO$_4$) and the solvent was distilled off under reduced pressure. The residue was subjected to silica gel column chromatography to 4-{3-chloro-2-[(2,5-dioxo-1-pyrrolidinyl)methyl]-7,7-dioxido-5,8-dihydro-6H-thiopyrano[4',3':4,5]thieno[2,3-b]pyridin-4-yl}phenyl 2-propane sulfonate (200 mg, 66%) from the fraction eluted with ethyl acetate-hexane (2:1). It was recrystallized from THF-hexane. Colorless prisms. Melting point 288–289° C.

According to the same manner, the compound of Example 86 shown in Table 8 was synthesized.

EXAMPLE 87

To a solution of the compound obtained in Example 32 (300 mg) in pyridine (5 ml) was added 4-morphonylcarbonyl chloride (188 mg) at room temperature. The reaction mixture was stirred to 10 hours and then crystals of 4-{3-chloro-2-[(2,5-dioxo-1-pyrrolidinyl)methyl]-7,7-dioxido-5,8-dihydro-6H-thiopyrano[4',3':4,5]thieno[2,3-b]pyridin-4-yl}phenyl morpholine carboxylate deposited was filtered off and washed with water. It was recrystallized from DNSO-water (152 mg, 41%). Pale yellow prisms. Melting point 327–328° C.

EXAMPLE 88

To a solution of the compound obtained in Example 32 (200 mg) in pyridine (4 ml) was added dimethylcarbamoyl chloride (113 mg) at room temperature. The reaction mixture was stirred for 10 hours, poured into water and extracted with ethyl acetate. The ethyl acetate layer was washed with water and dried (MgSO$_4$) and the solvent was distilled off under reduced pressure. The residue was subjected to silica gel column chromatography to obtain 4-{3-chloro-2-[2,5-dioxo-1-pyrrolidinyl)methyl]-7,7-dioxido-5,8-dihydro-6H-thiopyrano[4',3':4,5]thieno[2,3-b]pyridin-4-yl}phenyl dimethylcarbamate (180 mg, 79%) from the fraction eluted with ethyl acetate-hexane (2:1). It was recrystallized from chloroform-hexane. Colorless prisms. Melting point 290–291° C.

EXAMPLE 89

To a mixture of the compound obtained in Example 32 (500 mg), triethylamine (138 mg) and methylene chloride (10 ml) was added methyl chlorocarbonate (109 mg) under ice-cooling. The reaction mixture was stirred at room temperature for 1 hour, poured into water and then extracted with ethyl acetate. The ethyl acetate layer was washed with water and dried (MgSO$_4$) and the solvent was distilled off under reduced pressure to obtain 4-{3-chloro-2-[2,5-dioxo-1-pyrrolidinyl)methyl]-7,7-dioxido-5,8-dihydro-6H-thiopyrano[4',3':4,5]thieno[2,3-b]pyridin-4-yl}phenyl methylcarbonate (480 mg, 86%). It was recrystallized from ethyl acetate-hexane. Colorless prisms. Melting point 275–276° C.

According to the same manner, compounds of Examples 90 to 101, 103, 104, 107 and 108 shown in Table 9 were synthesized.

TABLE 9

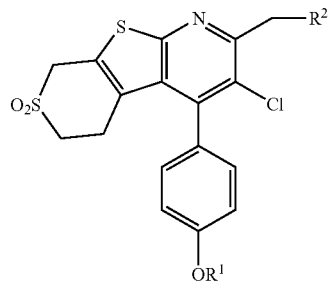

| Example No. | R$^1$ | R$^{2a)}$ | Melting point (° C.) | Recrystallization solvent |
|---|---|---|---|---|
| 89 | COOMe | suc | 275–276 | ethyl acetate-hexane |
| 90 | COOEt | suc | 231–232 | ethyl acetate-hexane |
| 91 | COOCH$_2$CH$_2$Me | suc | 156–157 | ethyl acetate-hexane |
| 92 | COO(CH$_2$)$_3$Me | suc | 173–174 | acetone-hexane |
| 93 | COOCHMe$_2$ | suc | 239–240 | ethyl acetate-hexane |
| 94 | COOCH$_2$CHMe$_2$ | suc | 237–238 | ethyl acetate-hexane |
| 95 | COO(CH$_2$)$_4$Me | suc | 143–144 | THF-hexane |
| 96 | COO(CH$_2$)$_5$Me | suc | amorphous solids | IR (KBr): 1765, 1707 cm$^{-1}$ |
| 97 | COO(CH$_2$)$_7$Me | suc | amorphous solids | IR (KBr): 1759, 1707 cm$^{-1}$ |
| 98 | COOCH$_2$Ph | suc | 160–161 | ethyl acetate-hexane |
| 99 | COO(CH$_2$)$_2$OMe | suc | 137–138 | THF-hexane |
| 100 | COOCH$_2$CH=CH$_2$ | suc | 209–210 | THF-hexane |
| 101 | COOCH$_2$CMe$_3$ | suc | 284–285 | THF-hexane |
| 102 | H | thia | 219–220 | acetonitrile-hexane |
| 103 | COO(CH$_2$)$_3$Me | thia | 163–164 | ethyl acetate-hexane |
| 104 | COOCH$_2$CHMe$_2$ | thia | 155–156 | ethyl acetate-hexane |
| 105 | Me | pht | 298–299 | THF-hexane |
| 106 | H | pht | 342–343 | methyl ethyl ketone-hexane |
| 107 | COO(CH$_2$)$_3$Me | pht | 172–173 | ethyl acetate-hexane |
| 108 | COOCH$_2$CHMe$_2$ | pht | 175–176 | ethyl acetate-hexane | a)

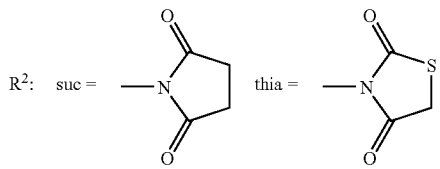

TABLE 9-continued

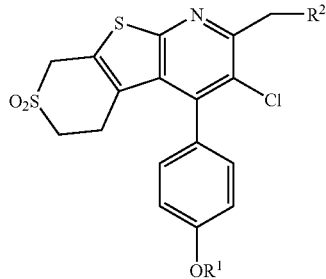

| Example No. | R[1] | R[2a)] | Melting point (° C.) | Recrystallization solvent |
|---|---|---|---|---| pht = (phthalimido group structure)

TABLE 10

(structure with (O)$_m$S—, Cl, OR substituents and pyrrolidinedione group)

| Example No. | R | m | Melting point (° C.) | Recrystallization solvent |
|---|---|---|---|---|
| 109 | CH$_2$OCH$_2$Ph | 2 | 122–123 | ethyl acetate-hexane |
| 110 | CH$_2$COOEt | 2 | 215–216 | ethyl acetate-hexane |
| 111 | H | 0 | 302–303 | ethyl acetate-hexane |
| 112 | CH$_2$COO$^t$Bu | 0 | 191–192 | ethyl acetate-hexane |
| 113 | CH$_2$COO$^t$Bu | 1 | 175–176 | ethyl acetate-hexane |
| 114 | CH$_2$COO$^t$Bu | 2 | 204–205 | ethyl acetate-hexane |
| 115 | CH$_2$COOH | 1 | 205–206 | methanol-diethyl ether |
| 116 | CH$_2$COOH | 2 | 260–261 | acetone-hexane |
| 117 | CH$_2$CONHCH$_2$Ph | 1 | 220–221 | THF-hexane |

EXAMPLE 102

A mixture of the compound obtained in Example 28 (2.2 g), DL-methionine (1.9 g) and methanesulfonic acid (20 ml) was stirred at 100° C. for 2 hours. The reaction mixture was ice-cooled and 15% aqueous ammonia solution (100 ml) was slowly added thereto under ice-cooling. After stirring for additional 30 minutes, 3-{[3-chloro-4-(4-hydroxyphenyl)-7,7-dioxido-5,8-dihydro-6H-thiopyrano-[4',3':4,5]thieno[2,3-b]pyridin-2-yl]methyl}thiazolidine-2,4-dione deposited was filtered off and washed with water. After drying, it was recrystallized from acetonitrile-diethyl ether (920 mg, 44%). Colorless prisms. Melting point 219–220° C.

According to the same manner, the compounds of Example 106 and Example 111 shown in Table 9 and Table 10 were synthesized.

EXAMPLE 105

To a solution of the compound obtained in Example 6 (2.8 g) in methylene chloride (60 ml) was added m-chloroperbenzoic acid (70%, 3.0 g) under ice-cooling and the mixture was stirred at room temperature for 1 hour. The reaction mixture was washed with an aqueous saturated sodium bicarbonate solution and then water, and dried (MgSO4) and the solvent was distilled off under reduced pressure to obtain crystals of 2-{[3-chloro-4-(4-methoxyphenyl)-7,7-dioxido-5,8-dihydro-6H-thiopyrano-[4',3':4,5]thieno[2,3-b]pyridin-2-yl]methyl}-1H-isoindole-1,3 (2H)-dione (2.0 g, 69%). It was recrystallized from THF-hexane. Colorless prisms. Melting point 298–299° C.

EXAMPLE 109

To a solution of the compound obtained in Example 32 (100 mg) in DMF (3 ml) was added sodium hydride (60% in oil, 11 mg) under ice-cooling and the mixture was stirred for 10 minutes. After addition of benzyl chloromethyl ether (65 mg) thereto, the mixture was stirred at 70° C. for 1 hour. The reaction mixture was poured into water and extracted with ethyl acetate. The ethyl acetate layer was washed with water and dried (MgSO$_4$) and the solvent was distilled off under reduced pressure. The residue was subjected to silica gel column chromatography to obtain 1-[(4-{4-[benzyloxy)methoxy]phenyl}-3-chloro-7,7-dioxido-5,8-dihydro-6H-thiopyrano[4',3':4,5]thieno[2,3-b]pyridin-2-yl)methyl]-2,5-pyrrolidinedione from the fraction eluted with ethyl acetate-hexane (3:2). It was recrystallized from ethyl acetate-hexane (35 mg, 28%). Colorless prisms. Melting point 122–123° C.

EXAMPLE 110

To a solution of the compound obtained in Example 32 (100 mg) in DMF (3 ml) was added sodium hydride (60% in oil, 11 mg) under ice-cooling and the mixture was stirred for 15 minutes. After addition of ethyl bromoacetate (70 mg) thereto, the mixture was further stirred at room temperature for 30 minutes. The reaction mixture was poured into water and extracted with ethyl acetate. The ethyl acetate layer was washed with water and dried (MgSO$_4$) and the solvent was distilled off under reduced pressure. The residue was subjected to silica gel column chromatography to obtain ethyl (4-{3-chloro-2-[(2,5-dioxo-1-pyrrolidinyl)methyl]-7,7-dioxid0-5,8-dihydro-6H-thiopyrano[4',3':4,5]thieno[2,3-b]pyridin-4-yl}phenoxy)acetate from the fraction eluted with ethyl acetate-hexane (3:2). It was recrystallized from ethyl acetate-hexane (30 mg, 25%). Colorless prisms. Melting point 215–216° C.

EXAMPLE 112

To a solution of the compound obtained in Example 111 (5.0 g) in DMF (50 ml) was added sodium hydride (60% in oil, 539 mg) under ice-cooling and the mixture was stirred for 15 minutes. After addition of tert-butyl bromoacetate (70 mg) thereto, the mixture was further stirred for 1.5 hours. The reaction mixture was poured into water and extracted with ethyl acetate. The ethyl acetate layer was washed with water and dried (MgSO$_4$) and the solvent was distilled off under reduced pressure. The residue was subjected to silica gel column chromatography to obtain tert-butyl (4-{3-chloro-2-[(2,5-dioxo-1-pyrrolidinyl)methyl]-5,8-dihydro-6H-thiopyrano[4',3':4,5]-thieno[2,3-b]pyridin-4-yl}phenoxy)acetate from the fraction eluted with ethyl acetate-hexane-chloroform (1:5:5). It was recrystallized from ethyl acetate-hexane (3.3 g, 53%). Colorless prisms. Melting point 191–192° C.

EXAMPLE 113

To a solution of the compound obtained in Example 112 (2.7 g) in methylene chloride (50 ml) was added m-chloroperbenzoic acid (70%, 1.2 g) under ice-cooling and the mixture was stirred at room temperature for 1 hour. The reaction mixture was washed with an aqueous saturated sodium bicarbonate solution and then water and dried (MgSO$_4$) and the solvent was distilled off under reduced pressure. The residue was subjected to silica gel column chromatography to obtain tert-butyl (4-{3-chloro-2-[(2,5-dioxo-1-pyrrolidinyl)methyl]-7-oxido-5,8-dihydro-6H-thiopyrano[4',3':4,5]thieno[2,3-b]pyridin-4-yl}phenoxy)-acetate from the fraction eluted with ethyl acetate. It was recrystallized from ethyl acetate-hexane (2.2 g, 79%). Colorless prisms. Melting point 175–176° C.

EXAMPLE 114

To a solution of the compound obtained in Example 112 (300 mg) in methylene chloride (6 ml) was added m-chloroperbenzoic acid (70%, 278 mg) under ice-cooling and the mixture was stirred at room temperature for 1 hour. The reaction mixture was washed with an aqueous saturated sodium bicarbonate solution and then water and dried (MgSO$_4$) and the solvent was distilled off under reduced pressure. The residue was subjected to silica gel column chromatography to obtain tert-butyl (4-{3-chloro-2-[(2,5-dioxo-1-pyrrolidinyl)methyl]-7,7-dioxido-5,8-dihydro-6H-thiopyrano[4',3':4,5]thieno[2,3-b]pyridin-4-yl}phenoxy)acetate from the fraction eluted with ethyl acetate-hexane (3:2). It was recrystallized from ethyl acetate-hexane (235 mg, 74%). Colorless prisms. Melting point 204–205° C.

EXAMPLE 115

A solution of the compound obtained in Example 113 (600 mg) in formic acid (7 ml) was stirred at room temperature for 6 hours and then concentrated under reduced pressure. The residue was diluted with methylene chloride and washed with water and dried (MgSO$_4$) and the solvent was distilled off under reduced pressure. The residue was subjected to silica gel column chromatography to obtain (4-{3-chloro-2-[(2,5-dioxo-1-pyrrolidinyl)methyl]-7-oxido-5,8-dihydro-6H-thiopyrano[4',3':4,5]thieno[2,3-b]pyridin-4-yl}phenoxy)acetic acid from the fraction eluted with chloroform-ethyl acetate (7:1) and then chloroform-methanol (10:1) (476 mg, 88%). It was recrystallized from methanol-hexane. Colorless prisms. Melting point 205–206° C.

EXAMPLE 116

A mixture of the compound obtained in Example 114 (200 mg), 10% aqueous hydrochloric acid (3 ml) and dioxane (5 ml) was stirred at 80° C. for 30 minutes. The reaction mixture was cooled to room temperature and poured into water. The mixture was extracted with ethyl acetate. The ethyl acetate layer was washed with water and dried (MgSO$_4$) and the solvent was distilled off under reduced pressure to obtain (4-{3-chloro-2-[(2,5-dioxo-1-pyrrolidinyl)methyl]-7,7-dioxido-5,8-dihydro-6H-thiopyrano-[4',3':4,5]-thieno[2,3-b]pyridin-4-yl}phenoxy)acetic acid (130 mg, 72%). It was recrystallized from acetone-hexane. Colorless prisms. Melting point 260–261° C.

EXAMPLE 117

A mixture of the compound obtained in Example 115 (104 mg), benzylamine (24 mg), 1-ethyl-3-(3-dimethylaminopropyl)carbodiimide hydrochloride (WSC, 42 mg), 1-hydroxy-1H-benzimidazole monohydrate (HOBt, 34 mg) and DMF (3 ml) was stirred at room temperature for 10 hours. The reaction mixture was poured into water. The mixture was extracted with ethyl acetate. The ethyl acetate layer was washed with water and dried (MgSO$_4$) and the solvent was distilled off under reduced pressure. The residue was subjected to silica gel column chromatography to obtain N-benzyl-2-(4-{3-chloro-2-[(2,5-dioxo-1-pyrrolidinyl)methyl]-7-oxido-5,8-dihydro-6H-thiopyrano[4',3':4,5]thieno[2,3-b]pyridin-4-yl}phenoxy)acetamide from the fraction eluted with ethyl acetate-methanol (6:1) (70 mg, 57%). It was recrystallized from THF-hexane. Colorless prisms. Melting point 220–221° C.

EXAMPLE 118

2-{[3-Chloro-4-(4-methoxyphenyl)-5,8-dihydro-6H-thiopyrano-[4',3':4,5]thieno[2,3-b]pyridin-2-yl]methyl}-1H-isoindole-1,3(2H)-dione To a mixture of phthalimide potassium (6.2 kg) and dimethylformamide (110.74 L) was added 3-chloro-2-chloromethyl-5,8-dihydro-4-(4-methoxyphenyl)-6H-thiopyrano-[4',3':4,5]thieno[2,3-b]pyridine (11.055 kg) obtained in Reference Example 27 and the mixture was stirred at 60 to 65° C. for 1 hour. After cooling to 25° C., water (36.91 L) was added dropwise thereto and the mixture was stirred at the same temperature for 1 hour. The crystals deposited was filtered off and washed with water (29.14 L) to obtain the titled compound (14.057 kg, 99.4%). $^1$H-NMR (CDCl$_3$) δ: 2.14 (2H, t, J=5.7 Hz), 2.64 (2H, t, J=5.7 Hz), 3.80 (2H, s), 3.89 (3H, s), 5.20 (2H, s), 6.98–7.13 (2H, s), 6.98–7.13 (3H, m), 7.75–7.78 (2H, m), 7.79–7.794 (2H, m).

EXAMPLE 119

2-{[3-Chloro-4-(4-methoxyphenyl)-7-oxido-5,8-dihydro-6H-thiopyrano[4',3':4,5]thieno[2,3-b]pyridin-2-yl]methyl}-1H-isoindole-1,3(2H)-dione To N-methylpyrrolidone (140.56 L) was added 2-{[3-chloro-4-(4-methoxyphenyl)-5,8-dihydro-6H-thiopyrano-[4',3':4,5]thieno[2,3-b]pyridin-2-yl]methyl}-1H-isoindole-1,3(2H)-dione (14.056 kg) and the mixture was dissolved by heating at about 40° C. Then, vanadium (IV) oxyacetylacetone (49.09 g) was added thereto and the 30% hydrogen peroxide was added dropwise, while maintaining at 20 to 23° C. The mixture was stirred at the same temperature for 1 hour and then cooled to 3° C., followed by adding dropwise 0.5 N sodium thiosulfate (5 L) and then water (281.14 L). The mixture was stirred for 1 hour under ice-cooling. The crystals deposited was filtered off, dried and dissolved in N-methylpyrrolidone (135.65 L). Active carbon (678 g) was added and the mixture was stirred at room temperature for 30 minutes. The active carbon was filtered off and washed with N-methylpyrrolidone (13.565 L). The filtrate and washings were combined and to the mixture was added dropwise isopropyl ether (298.43 L). The crystals deposited were filtered off, washed with isopropyl ether (67.83 L×2) to obtain the titled compound (9.56 kg, 64.3%). $^1$H-NMR (CDCl$_3$)δ: 2.01–2.19 (1H, m), 2.54–2.73 (2H, m), 3.00–3.07 (1H, m), 3.89 (3H, s), 3.95 (1H, d, J=16.9 Hz), 4.05 (1H, d, J=16.9 Hz), 5.20 (2H, s), 6.99–7.03 (2H, m), 7.16–7.20 (2H, m), 7.76–7.80 (2H, m), 7.91–7.95 (2H, m)

EXAMPLE 120

2-(Amonomethyl)-3-chloro-4-(4-methoxyphenyl)-7-oxido-5,8-dihydro-6H-thiopyrano[4',3':4,5]thieno[2,3-b]pyridine To a mixture of 2-{[3-chloro-4-(4-methoxyphenyl)-7-oxido-5,8-dihydro-6H-thiopyrano[4',3':4,5]thieno[2,3-b]pyridin-2-yl]methyl}-1H-isoindole-1,3(2H)-dione (8.94 kg) and diethylene glycol dimethyl ether (44.7 L) was added dropwise hydrazine hydrate (100%, 8.56 kg) and stirred at 60° C. for 5.5 hours. Water (44.7 L) was added dropwise and the mixture was cooled to room temperature. Isopropyl ether (32.4 kg) was added and the mixture was stirred for 1 hours. The deposited crystals were filtered off and washed with water (17.88 L) and isopropyl ether (8.94 kg) to obtain the titled compound (9.56 kg, 64.3%). $^1$H-NMR (CDCl$_3$)δ: 2.13–2.19 (1H, m), 2.54–2.73 (2H, m), 3.00–3.09 (1H, m), 3.89 (3H, s), 4.05 (1H, d, J=16.9 Hz), 4.09 (1H, d, J=16.9 Hz), 4.20 (2H, s), 6.98–7.03 (2H, m), 7.16–7.19 (2H, m).

EXAMPLE 121

(S)-2-(Aminomethyl)-3-chloro-4-(4-methoxyphenyl)-7-oxido-5,8-dihydro-6H-thiopyrano[4',3':4,5]thieno[2,3-b]pyridine To methanol heated to 60° C. (63 L) was added 2-(aminomethyl)-3-chloro-4-(4-methoxyphenyl)-7-oxido-5,8-dihydro-6H-thiopyrano[4',3':4,5]thieno[2,3-b]pyridine (6.5 kg) and the mixture was stirred for 5 minutes, followed by addition of (R)-(−)-hydrogenphosphate-1,1'-bihaphthyl-2,2'-diyl (3.455 kg). The mixture was stirred at 60° C. for 10 minutes, slowly cooled to 25° C. After stirring for 1 hours, crystals were filtered off and washed with methanol (13L). Methanol-ethanol (1:3, 63 L) was heated to 75° C. and the resultant crystals were added thereto. The mixture was slowly cooled to 25° C. and stirred for 1 hours. Crystals deposited were filtered off and washed with methanol-ethanol (1:1, 13 L). The crystals were dissolved in tetrahydrofuran-water (3:1, 121.4 L) and active carbon (242 g) was added thereto. The mixture was stirred at room temperature for 15 minutes and the active carbon was filtered off. The tetrahydrofuran layer was distilled off under reduced pressure and the resultant aqueous layer was stirred at 25° C. to deposit crystals. The crystals were filtered off to obtain a diastereomer salt of (S)-2-(aminomethyl)-3-chloro-4-(4-methoxyphenyl)-7-oxido-5,8-dihydro-6H-thiopyrano[4',3':4,5]thieno[2,3-b]pyridine with (R)-(−)-hydrogenphosphate-1,1'-binaphthyl-2,2'-diyl (4.618 kg, 37.7%). $^1$H-NMR (DMSO-d$_6$)δ: 1.98–2.04 (1H, m), 2.35–2.43 (1H, m), 2.71–2.81 (1H, m), 3.01–3.06 (1H, m), 3.83 (3H, s), 3.18 (1H, d, J=17.1 Hz), 4.26 (1H, d, J=17.1 Hz), 4.35 (2H, s), 0.07–7.43 (12H, m), 7.96–8.10 (4H, m), 8.64 (3H, bs).

This diastereomer salt (1.538 kg) was added to a mixture of dimethyl sulfoxide (8.1 L), water (7.8 L), dichloromethane (16.2 L) and a 25% aqueous ammonium solution (324 ml) and the mixture was stirred. After dissolution of crystals, the dichloromethane layer was separated. The aqueous layer was further extracted with dichloromethane. The extracts were combined and washed with 1% saline (16.2 L×2) and concentrated so that the weight of the content became 2.98 kg. To the residue was added dropwise isopropyl ether (3.26 L) with stirring and the mixture was allowed to stand overnight. The resultant crystals were filtered off to obtain the titled compound. $^1$H-NMR (CDCl$_3$) δ: 2.14–2.22 (1H, m), 2.60–2.77 (2H, m), 3.07–3.13 (1H, m), 3.91 (3H, s), 4.06 (1H, d, J=15 Hz), 4.14 (1H, d, J=15 Hz), 4.23 (2H, s), 7.01–7.06 (2H, m), 7.17–7.21 (2H, m).

EXAMPLE 122

1-{[3-Chloro-4-(4-methoxyphenyl)-5,8-dihydro-6H-thiopyrano[4',3':4,5]thieno[2,3-b]pyridin-2-yl]methyl}-2,5-pyrrolidinedione To dimethyl sulfoxide (2450 ml) was added 28% sodium methoxide (97.4 g), followed by addition of succinimide (178.9 g). The mixture was stirred at about 20° C. for 30 minutes and then 3-chloro-2-chloromethyl-5,8-dihydro-4-(4-methoxyphenyl)-6H-thiopyrano[4',3':4,5]thieno-[2,3-b]pyridine (490 g) was added thereto. The mixture was stirred at room temperature for 2.5 hours and then a mixture of methanol (1225 ml) and water (490 g) was added dropwise thereto. The mixture was stirred at 10° C. or lower and crystals deposited were filtered off to the titled compound (546 g, 96.3%).

EXAMPLE 123

1-{[3-Chloro-4-(4-methoxyphenyl)-7-oxido-5,8-dihydro-6H-thiopyrano[4',3':4,5]thieno[2,3-b]pyridin-2-yl]methyl}-2,5-pyrrolidinedione A mixture of 1-{[3-chloro-4-(4-methoxyphenyl)-5,8-dihydro-6H-thiopyrano[4',3':4,5]thieno[2,3-b]pyridin-2-yl]methyl}-2,5-pyrrolidinedione (239.6 g) and dimethylformamide (1.8 L) was cooled to −7° C. and vanadium (IV) oxyacetylacetone (691 mg) was added thereto. 30% Hydrogen peroxide (59.2 g) was added dropwise and the mixture was stirred at 2° C. or lower for 8 hours. 0.5N Sodium thiosulfate (100 ml) and water (3 L) were added dropwise at 5 to 7° C. and the mixture was stirred at 15 to 20° C. for 1 hour. Crystals deposited were filtered off to obtain the titled compound (242 g, 97.5%). $^1$H-NMR (CDCl$_3$)δ: 2.13–2.20 (1H, m), 2.54–2.73 (2H, m), 3.02–3.09 (1H, m), 3.90 (3H, s), 4.00 (1H, d, J=16.9 Hz), 4.10 (1H, d, J=16.9 Hz), 5.00 (1H, d, J=17.2 Hz), 5.06 (1H, d, J=17.2 Hz), 7.01 (2H, d, J=8.1 Hz), 7.16 (2H, d, J=8.1 Hz).

EXAMPLE 124

(S)-1-{[-3-Chloro-4-(4-methoxyphenyl)-7-oxido-5,8-dihydro-6H-thiopyrano[4',3':4,5]thieno[2,3-b]pyridin-2-yl]methyl}-2,5-pyrrolidinedione To a solution of succinic anhydride (303.25 g) in DMF (3.5.L) was added (S)-2-(aminomethyl)-3-chloro-4-(4-methoxyphenyl)-7-oxido-5,8-dihydro-6H-thiopyrano-[4',3': 4,5]thieno[2,3-b]pyridine (1134 g) and the mixture was stirred for 1 hour. To the mixture was slowly added carbonyldiimidazole (935.5 g), and stirred at room temperature for 22 hours and further at 36 to 38° C. for 5 hours. The reaction mixture was added dropwise to water (20 L). After stirring for 2.5 hours, crystals deposited were filtered off and washed with water (1277 g, 86.4%). This product was dissolved in a mixture of acetonitrile (8.7 L) and water (2.9 L) and treated with active carbon. Water (45 L) was added and crystals were filtered off. The crystals were suspended in acetone (2.9 L), stirred at 48 to 52° C. for 1 hour and cooled to room temperature. Crystals were filtered off to obtain the titled compound (997 g). Melting point 217–218.5° C. (decomp.) $[\alpha]_D^{20}$ −123.63 (c=0.00490, CHCl$_3$).

Elemental analysis for $C_{22}H_{19}ClN_2O_4S_2$ Calcd: C, 55.63; H, 4.03; N, 5.90. Found: C, 55.58; H, 4.18; N, 5.94. $^1$H-NMR (CDCl$_3$) δ: 2.13–2.20 (1H, m), 2.54–2.73 (2H, m), 2.91 (4H, s), 3.02–3.09 (1H, m), 3.90 (3H, s), 4.00 (1H, d, J=16.9 Hz), 4.10 (1H, d, J=16.9 Hz), 5.00 (1H, d, J=17.2 Hz), 5.06 (1H, d, J=17.2 Hz), 7.01 (2H, d, J=8.1 Hz), 7.16 (2H, d, J=8.1 Hz).

As described hereinabove, since compounds (I) or salts thereof of the present invention have excellent anti-inflammatory activity, they are useful as anti-inflammatory drugs, particularly as remedies for arthritis. Further, they are useful in the prevention and treatment of bone destruction, osteoporosis, and the like, which accompany arthritis, because they have excellent suppressing effects on bone resorption. Furthermore, they are useful in the prevention and treatment of diseases associated with immune reactions including autoimmune disease because they have excellent suppressing effects on immune cytokine production. They are also useful as prophylactic and therapeutic drugs of rejection reaction after organ transplantation. Moreover, compounds (I) or salts thereof of the present invention are low in toxicity and stable against the metabolism in the living body so that they exert the medical efficacy for a long period of time and can be advantageously used as medicaments.

What is claimed is:

1. A compound represented by the formula (I):

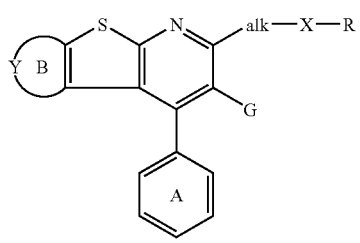

wherein G represents a halogen atom, hydroxyl group, an optionally substituted amino group, an optionally substituted lower alkyl group or an optionally substituted alkoxy group; alk represents an optionally substituted lower alkylene group; X represents oxygen atom, an optionally oxidized sulfur atom, or —(CH$_2$)q—, wherein q represents an integer of 0 to 5; R represents an optionally substituted amino group or an optionally substituted heterocyclic group; ring B represents an optionally substituted Y-containing 5- to 8-membered ring whose ring constituent atoms contain no nitrogen atom; Y represents oxygen atom, an optionally oxidized sulfur atom,

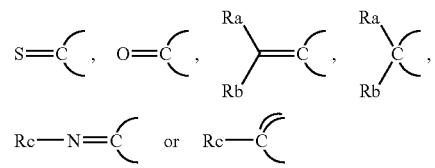

wherein Ra and Rb are the same or different and, respectively, represent hydrogen atom, a halogen atom, an optionally substituted hydrocarbon group, an optionally substituted acyl group, an optionally substituted carbamoyl group, an optionally substituted thiocarbamoyl group, an optionally substituted sulfonyl group, an optionally substituted sulfinyl group, an optionally substituted hydroxyl group, an optionally substituted thiol group, an optionally esterified carboxyl group, or an optionally substituted heterocyclic group, or Ra and Rb may be combined to form a 5- to 7-membered ring; and Rc represents hydrogen atom, a halogen atom, an optionally substituted hydrocarbon group, an optionally substituted acyl group, an optionally substituted carbamoyl group, an optionally substituted thiocarbamoyl group, an optionally substituted sulfonyl group, an optionally substituted sulfinyl group, an optionally substituted hydroxyl group, an optionally substituted thiol group, an optionally esterified carboxyl group, or an optionally substituted heterocyclic group; and ring A represents an optionally substituted benzene ring, or a salt thereof.

2. The compound according to claim 1, wherein alk is methylene.

3. The compound according to claim 1, wherein G is a halogen atom.

4. The compound according to claim 1, wherein G is chlorine atom.

5. The compound according to claim 1, wherein X is —(CH$_2$)q—, wherein q represents an integer of 0 to 5.

6. The compound according to claim 1, wherein X is a bond.

7. The compound according to claim 1, wherein the optionally substituted amino group represented by R is —N(R$^1$)(R$^2$) wherein R$^1$ and R$^2$, which may be the same or different, respectively, represent hydrogen atom, an optionally substituted hydrocarbon group, or an optionally substituted acyl, sulfonyl, sulfinyl, or heterocyclic group, or R$^1$ and R$^2$ may be combined each other to form an optionally substituted nitrogen-containing 5- to 7-membered heterocyclic group.

8. The compound according to claim 7, wherein R$^1$ and R$^2$ are combined each other to form a nitrogen-containing optionally substituted 5- to 7-membered heterocyclic group.

9. The compound according to claim 7, wherein R$^1$ and R$^2$ are acyl groups.

10. The compound according to claim 1, wherein R is an optionally substituted nitrogen-containing heterocyclic group.

11. The compound according to claim 1, wherein the substituent on the optionally substituted heterocyclic group represented by R is oxo group.

12. The compound according to claim 1, wherein R is

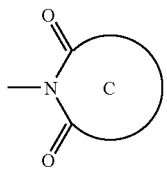

wherein ring C represents a 5- to 7-membered heterocyclic group optionally containing one or more hetero atoms selected from nitrogen, sulfur and oxygen atoms, in addition to the nitrogen atom.

13. The compound according to claim 1, wherein ring B is an optionally substituted 6-membered ring containing Y.

14. The compound according to claim 1, wherein the substituents on ring B are one to four substituents selected from a $C_{1-6}$ alkyl group and a halogen atom.

15. The compound according to claim 1, wherein ring B is a ring represented by the formula:

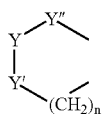

wherein Y' and Y" represent carbon atom, sulfur atom or oxygen atom, respectively; n represents an integer of 0 to 4; and Y is as defined in claim 1.

16. The compound according to claim 1, wherein Y is an optionally oxidized sulfur atom or

17. The compound according to claim 1, wherein ring A is benzene ring which may be substituted with one to four substituents selected from a halogen atom, nitro group, an optionally substituted alkyl group, an optionally substituted hydroxyl, an optionally substituted thiol group, an optionally substituted amino group, an optionally substituted acyl group, an optionally esterified carboxyl group, and an optionally substituted aromatic ring group.

18. The compound according to claim 1, wherein the substituent on ring A is a $C_{1-6}$ alkoxy group or hydroxyl group.

19. The compound according to claim 1, wherein the compound represented by formula (I) is:
- 1-{[3-chloro-4-(4-methoxyphenyl)-7-oxo-5,6,7,8-tetrahydro[1]benzothieno[2,3-b]pyridin-2-yl]methly}-2,5-pyrrolidinedione ethylene ketal;
- 3-{[3-chloro-4-(4-methoxyphenyl)-7-oxido-5,8-dihydro-6H-thiopyrano[4',3':4,5]thieno[2,3-b]pyridin-2-yl]methyl}-1,3-thiazolidine-2,4-dione or an optically active compound thereof or a salt thereof;
- 3-{[3-chloro-4-(4-methoxyphenyl)-7-oxido-5,8-dihydro-6H-thiopyrano[4',3':4,5]thieno[2,3-b]pyridin-2-yl]methyl}-1,3-oxazolidine-2,4-dione or an optically active compound thereof or a salt thereof;
- 1-{[3-chloro-4-(4-methoxyphenyl)-7-oxido-5,8-dihydro-6H-thiopyrano[4',3':4,5]thieno[2,3-b]pyridin-2-yl]methyl}-2,5-pyrrolidinedione or an optically active compound thereof or a salt thereof;
- 1-{[3-chloro-4-(4-methoxyphenyl)-7-oxo-5,6,7,8-tetrahydro[1]benzothieno[2,3-b]pyridin-2-yl]methyl}-2,5-pyrrolidinedione or a salt thereof;
- 1-{[3-chloro-4-(4-methoxyphenyl)-7-oxo-5,6,7,8-tetrahydro[1]benzothieno[2,3-b]pyridin-2-yl]methyl}-2,5-pyrrolidinedione or a salt thereof;
- 3-{[3-chloro-4-(4-methoxyphenyl)-8,8-dimethyl-7-oxo-5,6,7,8-tetrahydro[1]benzothieno[2,3-b]pyridin-2-yl]methyl}-1,3-thiazolidine-2,4-dione or a salt thereof;
- 1-{[3-chloro-4-(4-methoxyphenyl)-6,6-dimethyl-7-oxo-5,6,7,8-tetrahydro[1]benzothieno[2,3-b]pyridin-2-yl]methyl}-2,5-pyrrolidinedione or a salt thereof; or
- 2-aminomethyl-3-chloro-4-(4-methoxyphenyl)-7-oxido-5,8-dihydro-6H-thiopyrano[4',3':4,5]thieno[2,3-b]pyridine or an optically active compound thereof or a salt thereof.

20. The compound according to claim 1, wherein the compound represented by formula (I) is:
- 1-{[3-chloro-4-(4-methoxyphenyl)-7-oxo-5,6,7,8-tetrahydro[1]benzothieno[2,3-b]pyridin-2-yl]methyl}-2,5-pyrrolidinedione or a salt thereof;
- 1-{[3-chloro-4-(4-methoxyphenyl)-8,8-dimethyl-7-oxo-5,6,7,8-tetrahydro[1]benzothieno[2,3-b]pyridin-2-yl]methyl}-2,5-pyrrolidinedione or a salt thereof;
- 3-{[3-chloro-4-(4-methoxyphenyl)-8,8-dimethyl-7-oxo-5,6,7,8-tetrahydro[1]benzothieno[2,3-b]pyridin-2-yl]methyl}-1,3-thiazolidine-2,4-dione or a salt thereof; or
- 1-{[3-chloro-4-(4-methoxyphenyl)-6,6-dimethyl-7-oxo-5,6,7,8-tetrahydro[1]benzothieno[2,3-b]pyridin-2-yl]methyl}-2,5-pyrrolidinedione or a salt thereof.

21. The compound according to claim 1, wherein the compound represented by formula (I) is:
- 1-{[3-chloro-4-(4-hydroxyphenyl)-7,7-dioxido-5,8-dihydro-6H-thiopyrano[4',3':4,5]thieno[2,3-b]pyridin-2-yl]methyl}-2,5-pyrrolidinedione or a salt thereof;
- 4-{3-chloro-2-[2,5-dioxo-1-pyrrolidinyl)methyl]-7,7-oxido-5,8-dihydro-6H-thiopyrano[4',3':4,5]thieno[2,3-b]pyridin-4-yl]phenyl} diIsobutyl phosphate or a salt thereof; or butyl 4-{3-chloro-2-[(2,5-dioxo-1-pyrrolidinyl)methyl]-7,7-dioxido-5,8-dihydro-6H-thiopyrano[4',3':4,5]thieno[2,3-b]pyridin-4-yl}phenyl carbonate or a salt thereof.

22. A prodrug of the compound according to claim 1.

23. A process for producing a compound represented by the formula (I):

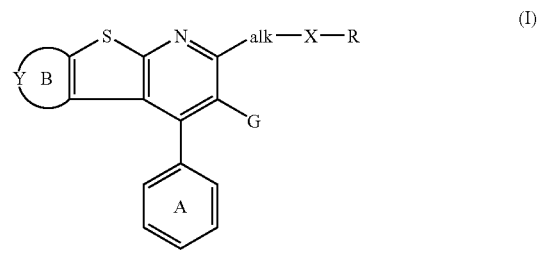

wherein G represents a halogen atom, hydroxyl group, an optionally substituted amino group, an optionally substituted lower ailcyl group or an optionally substituted alkoxy group;

alk represents an optionally substituted lower alkylene group; X represents oxygen atom, an optionally oxidized sulfur atom, or —(CH$_2$)$_q$—, wherein q represents an integer of 0 to 5; R represents an optionally substituted amino group or an optionally substituted heterocyclic group; ring B represents an optionally substituted Y-containing 5- to 8-membered ring whose ring constituent atoms contain no nitrogen atom; Y represents oxygen atom, an optionally oxidized sulfur atom,

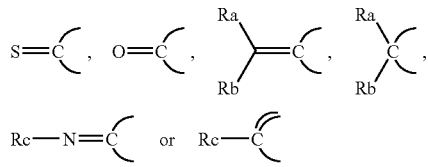

wherein Ra and Rb are the same or different and, respectively, represent hydrogen atom, a halogen atom, an optionally substituted hydrocarbon group, an optionally substituted acyl group, an optionally substituted carbamoyl group, an optionally substituted thiocarbamoyl group, an optionally substituted sulfonyl group, an optionally substituted sulfinyl group, an optionally substituted hydroxyl group, an optionally substituted thiol group, an optionally esterified carboxyl group, or an optionally substituted heterocyclic group, or Ra and Rb may be combined to form a 5- to 7-membered ring; and Rc represents hydrogen atom, a halogen atom, an optionally substituted hydrocarbon group, an optionally substituted acyl group, an optionally substituted carbamoyl group, an optionally substituted thiocarbamoyl group, an optionally substituted sulfonyl group, an optionally substituted sulfinyl group, an optionally substituted hydroxyl group, an optionally substituted thiol group, an optionally esterified carboxyl group, or an optionally substituted heterocyclic group; and ring A represents an optionally substituted benzene ring, or a salt thereof which comprises reacting a compound represented by the formula (II-1):

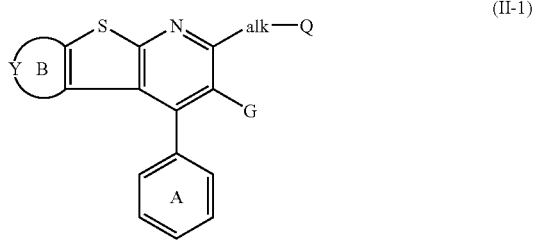

wherein Q represents a leaving group; and the other symbols are as defined above, or a salt thereof, with a compound represented by the formula (III):

wherein R is as defined above; and X$^1$ represents oxygen atom, or an optionally oxidized sulfur atom, or a salt thereof to obtain a compound represented by the formula (I-1):

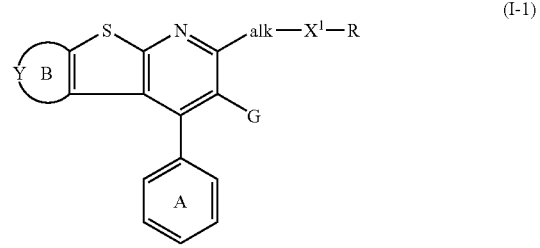

wherein each symbol is as defined above, or a salt thereof; or reacting a compound represented by the formula (II-2):

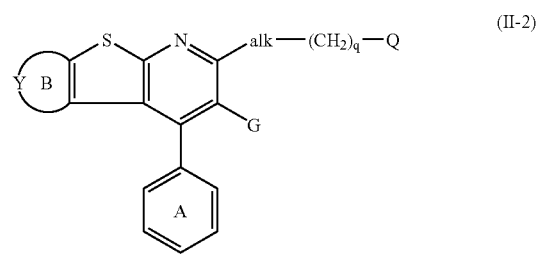

wherein each symbol is as defined above, or a salt thereof, with a compound represented by the formula (IV):

wherein R$^1$ and R$^2$, which may be the same or different, respectively, represent an optionally substituted hydrocarbon group, an optionally substituted acyl group, an optionally substituted sulfonyl group, or an optionally substituted heterocyclic group, or R$^1$ and R$^2$ may be combined to form an optionally substituted nitrogen-containing 5- to 7-membered ring, or a salt thereof to obtain a compound represented by the formula (I-2):

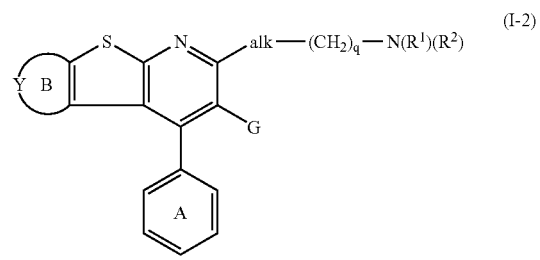

wherein each symbol is as defined above, or a salt thereof; or subjecting a compound represented by the formula (I-3):

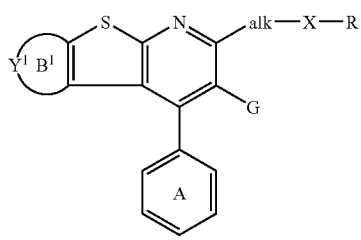

(I-3)

wherein ring $B^1$ represents an optionally substituted $Y^1$-containing 5- to 8-membered ring whose ring constituent atoms contain no nitrogen atom; $Y^1$ represents sulfur atom or

and the other symbols are as defined above, or a salt thereof to oxidation to obtain a compound represented by the formula (I-4):

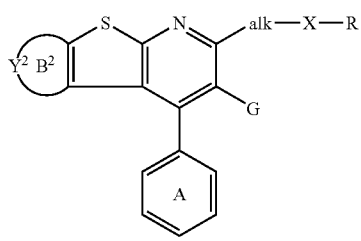

(I-4)

wherein ring $B^2$ represents an optionally substituted $Y^2$-containing 5- to 8-membered ring whose constituent ring atoms contain no nitrogen atom; $Y^2$ represents an oxidized sulfur atom or

and the other symbols are as defined above, or a salt thereof; or reacting a compound represented by the formula (II-3):

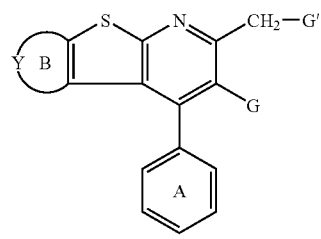

(II-3)

wherein G' represents a halogen atom; and the other symbols are as defined above, or a salt thereof, with

in a solvent to obtain a compound represented by formula (VI):

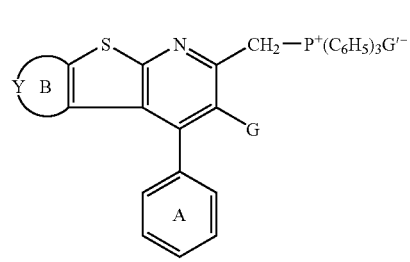

(VI)

wherein each symbol is as defined above, then reacting the compound represented by the formula (VI) with a compound represented by the formula (VII):

$$Z^1\text{-}(CH_2)_q\text{CHO} \quad (VII)$$

wherein $Z^1$ represents an optionally substituted heterocyclic group; and q' represents an integer of 0 to 4, or a salt thereof to obtain a compound represented by formula (VIII):

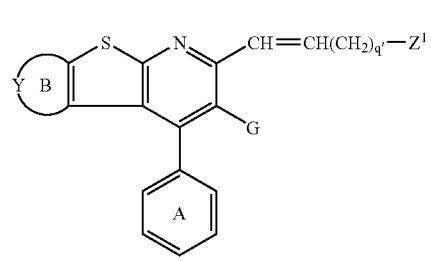

(VIII)

wherein each symbol is as defined above, or a salt thereof, and further subjecting the compound represented by formula (VIII) or a salt thereof to reduction to obtain a compound represented by the formula (I-5):

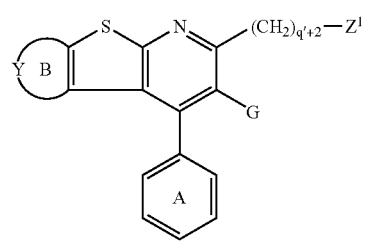

(I-5)

wherein each symbol is as defined above, or a salt thereof; or reacting a compound represented by the formula (II-1):

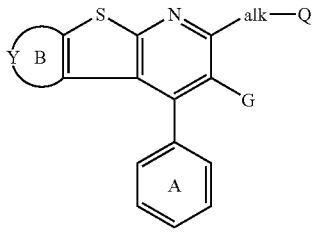
(II-1)

wherein each symbol is as defined above, or a salt thereof, with a compound represented by formula (XII):

R—H    (XII)

wherein R is as defined above, or a salt thereof to obtain a compound represented by the formula (I-9):

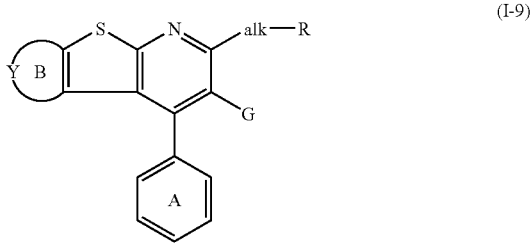
(I-9)

wherein each symbols is as defined above, or a salt thereof.

24. A pharmaceutical composition comprising a compound represented by the formula (I):

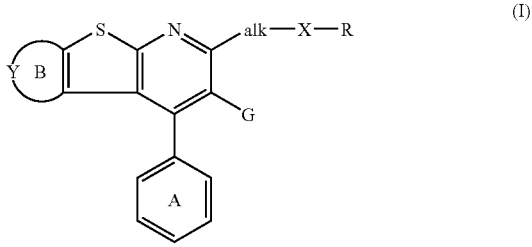
(I)

wherein G represents a halogen atom, hydroxyl group, an optionally substituted amino group, an optionally substituted lower alkyl group or an optionally substituted alkoxy group; alk represents an optionally substituted lower alkylene group; X represents oxygen atom, an optionally oxidized sulfur atom, or —$(CH_2)_q$—, wherein q represents an integer of 0 to 5; R represents an optionally substituted amino group or an optionally substituted heterocyclic group; ring B represents an optionally substituted Y-containing 5- to 8-membered ring whose ring constituent atoms contain no nitrogen atom; Y represents oxygen atom, an optionally oxidized sulfur atom,

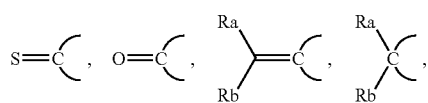

-continued

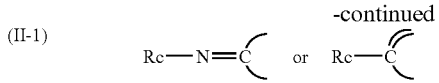

wherein Ra and Rb are the same or different and, respectively, represent hydrogen atom, a halogen atom, an optionally substituted hydrocarbon group, an optionally substituted acyl group, an optionally substituted carbamoyl group, an optionally substituted thiocarbamoyl group, an optionally substituted sulfonyl group, an optionally substituted sulfinyl group, an optionally substituted hydroxyl group, an optionally substituted thiol group, an optionally esterified carboxyl group, or an optionally substituted heterocyclic group, or Ra and Rb may be combined to form a 5- to 7-membered ring; and Rc represents hydrogen atom, a halogen atom, an optionally substituted hydrocarbon group, an optionally substituted acyl group, an optionally substituted carbamoyl group, an optionally substituted thiocarbamoyl group, an optionally substituted sulfonyl group, an optionally substituted sulfinyl group, an optionally substituted hydroxyl group, an optionally substituted thiol group, an optionally esterified carboxyl group, or an optionally substituted heterocyclic group; and ring A represents an optionally substituted benzene ring, a prodrug thereof, or a pharmaceutically acceptable salt thereof, and a pharmaceutically acceptable carrier, excipient or diluent.

25. A method for making a pharmaceutical composition for treating inflammatory diseases comprising combining a compound represented by the formula (I):

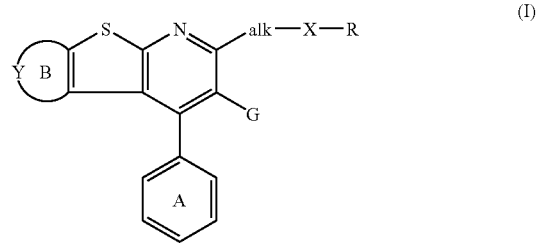
(I)

wherein G represents a halogen atom, hydroxyl group, an optionally substituted amino group, an optionally substituted lower alkyl group or an optionally substituted alkoxy group; alk represents an optionally substituted lower alkylene group; X represents oxygen atom, an optionally oxidized sulfur atom, or —$(CH_2)_q$—, wherein q represents an integer of 0 to 5; R represents an optionally substituted amino group or an optionally substituted heterocyclic group; ring B represents an optionally substituted Y-containing 5- to 8-membered ring whose ring constituent atoms contain no nitrogen atom; Y represents oxygen atom, an optionally oxidized sulfur atom,

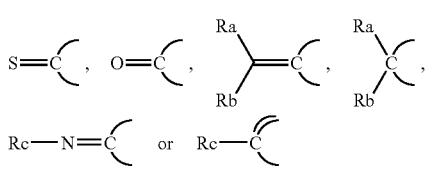

wherein Ra and Rb are the same or different and, respectively, represent hydrogen atom, a halogen atom, an optionally substituted hydrocarbon group, an optionally substituted acyl group, an optionally substituted carbamoyl group, an optionally substituted thiocarbamoyl group, an optionally substituted sulfonyl group, an optionally substituted sulfinyl group, an optionally substituted hydroxyl group, an optionally substituted thiol group, an optionally esterified carboxyl group, or an optionally substituted heterocyclic group, or Ra and Rb may be combined to form a 5- to 7-membered ring; and Rc represents hydrogen atom, a halogen atom, an optionally substituted hydrocarbon group, an optionally substituted acyl group, an optionally substituted carbamoyl group, an optionally substituted thiocarbamoyl group, an optionally substituted sulfonyl group, an optionally substituted sulfinyl group, an optionally substituted hydroxyl group, an optionally substituted thiol group, an optionally esterified carboxyl group, or an optionally substituted heterocyclic group; and ring A represents an optionally substituted benzene ring, a prodrug thereof, or a pharmaceutically acceptable salt thereof, with a pharmaceutically acceptable carrier, excipient or diluent.

* * * * *